(12) United States Patent
Wang et al.

(10) Patent No.: US 11,613,745 B2
(45) Date of Patent: Mar. 28, 2023

(54) RECOMBINANT OXALATE DECARBOXYLASE EXPRESSED IN FILAMENTOUS FUNGI

(71) Applicant: Wuhan Kangfude Biotechnology Co., Ltd., Wuhan (CN)

(72) Inventors: Wei Wang, Wuhan (CN); Xiaofeng Wang, Wuhan (CN); Yanhong Liu, Wuhan (CN); He Huang, Wuhan (CN); Huoqing Chen, Wuhan (CN); Xianqiao Chen, Wuhan (CN)

(73) Assignee: WUHAN KANGFUDE BIOTECHNOLOGY CO., LTD., Wuhan (CN)

( * ) Notice: Subject to any disclaimer, the term of this patent is extended or adjusted under 35 U.S.C. 154(b) by 53 days.

(21) Appl. No.: 16/978,763

(22) PCT Filed: Sep. 21, 2018

(86) PCT No.: PCT/CN2018/107053
§ 371 (c)(1),
(2) Date: Sep. 7, 2020

(87) PCT Pub. No.: WO2019/169855
PCT Pub. Date: Sep. 12, 2019

(65) Prior Publication Data
US 2021/0002625 A1   Jan. 7, 2021

(30) Foreign Application Priority Data
Mar. 5, 2018   (CN) .......................... 201810177819.3

(51) Int. Cl.
C12N 9/88       (2006.01)
C12N 1/14       (2006.01)
C12N 15/80      (2006.01)

(52) U.S. Cl.
CPC ................ *C12N 9/88* (2013.01); *C12N 1/14* (2013.01); *C12N 15/80* (2013.01); *C12Y 401/01002* (2013.01)

(58) Field of Classification Search
CPC . C12N 9/88; C12N 1/14; C12N 15/80; C12Y 401/01002
See application file for complete search history.

(56) References Cited

U.S. PATENT DOCUMENTS

| | | | |
|---|---|---|---|
| 7,307,158 B2 | 12/2007 | Suzuki | |
| 8,518,669 B2 | 8/2013 | Koyama et al. | |
| 2013/0216515 A1* | 8/2013 | Sidhu .................. | A61K 9/1682 435/232 |

FOREIGN PATENT DOCUMENTS

| | | |
|---|---|---|
| CN | 1656220 A | 8/2005 |
| CN | 101063119 A | 10/2007 |
| CN | 101918551 A | 12/2010 |
| CN | 102533707 A | 7/2012 |
| CN | 102939382 A | 2/2013 |
| CN | 106434603 A | 2/2017 |
| CN | 106939315 A | 7/2017 |
| CN | 106939315 B * | 11/2017 |
| WO | 2008105911 A2 | 9/2008 |
| WO | 2013102674 A2 | 7/2013 |
| WO | 2016161455 A2 | 10/2016 |

OTHER PUBLICATIONS

Li et al. Achieving efficient protein expression in Trichoderma reesei by using strong constitutive promoters. Microbial Cell Factories 2012, 11:84: p. 1-10.*
GenBank:PBK67661.1, oxalate decarboxylase [Armillaria solidipes], 2017.
GenBank:GAA90334.1, oxalate decarboxylase [Aspergillus kawachii IFO 4308], 2015.
NCBI Reference Sequence: XP_007331359.1, hypothetical protein AGABI1DRAFT_114840[*Agaricus bisporus* var. burnettii JB 137-S8], 2014.
GenBank:AAF13275.1, oxalate decarboxylase [Flammulina velutipes], 2000.
GenBank:KDR78673.1, hypothetical protein GALMADRAFT_244166[Galerina marginata CBS 339.88], 2014.
GenBank:AAQ67425.1, oxalate decarboxylase [Trametes versicolor], 2003.
GenBank:PCH42527.1, hypothetical protein WOLCODRAFT_177553 [Wolfiporia cocos MD-104 SS10], 2017.
GenBank:GAQ40670.1, oxalate decarboxylase [Aspergillus niger], 2015.
NCBI Reference Sequence:XM_001396897.2, Aspergillus niger CBS 513.88 oxalate decarboxylase, mRNA, 2011.

(Continued)

*Primary Examiner* — Iqbal H Chowdhury
(74) *Attorney, Agent, or Firm* — Novick, Kim & Lee, PLLC; Allen Xue

(57) ABSTRACT

The present invention relates to a recombinant OxDC expressed in a filamentous fungal host cell, methods for constructing a recombinant filamentous fungal host cell, methods for producing recombinant OxDC and the application thereof. The recombinant filamentous fungal host cell comprises one or more copies of OxDC expression cassette integrated in its genome; the expression cassette comprises a promoter, a signal peptide coding sequence, an OxDC coding sequence and a transcription terminator. The host cell can be constructed by random integration or site-specific integration. In addition, the present invention also optimizes the medium formulation for different recombinant filamentous fungal host cells. In the production of the recombinant OxDC, the final yield and enzyme activity were greatly improved. The invention effectively solves the problem that the production of OxDC in the prior art cannot be industrialized on a large scale.

8 Claims, 19 Drawing Sheets

Specification includes a Sequence Listing.

(56) References Cited

OTHER PUBLICATIONS

Xu Yan, Fermentation Conditions for Producing Xylanase by Aspergilus Niger IME-216 and Overexpression of Xylanase Gene in *Saccharomyces cerevisiae*, China Master's Theses Full-text Database, Dec. 31, 2011, pp. 1-83.
Meenu Kesarwani, et al., Oxalate Decarboxylase from Collybia velutipes, The Journal of Biological Chemistry, 2000, pp. 7230-7238, vol. 275, No. 10.
Mohammad Azam, et al., A Secretion Signal is Present in the Collybia velutipes Oxalate Decarboxylase Gene, Biochemical and Biophysical Research Communications, 2001, pp. 807-812, vol. 289.
Long Hao, et al., Isolation of Trichoderma reesei pyrG Negative Mutant by UV Mutagenesis and its Application in Transformation, Chem. Res. Chinese Universities, 2008, pp. 565-569, vol. 24(5).
Gerhard Weidner, et al., Development of a homologous transformation system for the human pathogenic fungus Aspergillus fumigatus based on the pyrG gene encoding orotidine 5'-monophosphate decarboxylase, Current Genetics, 1998, pp. 378-385, 33.
Jeffrey L. Smith, et al., Sequence of the cloned pyr4 gene of Trichoderma reesei and its use as a homologous selectable marker for transformation, Current Genetics, 1991, pp. 27-33, 19.
Gynheung An, et al., Binary vectors, Plant Molecular Biology Manual A3, 1988, pp. 1-19.
Song Gao, et al., A method for amplification of unknown flanking sequences based on touchdown PCR and suppression-PCR, Analytical Biochemistry, 2016.
Matthias G. Steiger, et al., Transformation System for Hypocrea jecorina (Trichoderma reesei) That Favors Homologous Integration and Employs Reusable Bidirectionally Selectable Markers, Applied and Environmental Microbiology, Jan. 2011, pp. 114-121, vol. 77 No. 1.
Craig B. Langman, et al., A Double-Blind, Placebo Controlled, Randomized Phase 1 Cross-Over Study with ALLN-177, an Orally Administered Oxalate Degrading Enzyme, American Journal of Nephrology, 2016, pp. 150-158, vol. 44.
Diego Martinez, et al., Genome sequencing and analysis of the biomass-degrading fungus Trichoderma reesei (syn. Hypocrea jecorina), Nature Biotechnology, Retrieved from: https://mycocosm.jgi.doe.gov/Trire2/Trire2.home.html, 2008, pp. 553-1193, vol. 26 No. 10.
Dias, B.B.A. et al.; "Expression of an oxalate decarboxylase gene from *Flammulina* sp. in transgenic lettuce (*Lactuca sativa*) plants and resistance to Sclerotinia sclerotiorum"; Plant Pathology; vol. 55; 2006; pp. 187-193.
Silva, Leonardo F. Da et al.; "Expression of an Oxalate Decarboxylase Impairs the Necrotic Effect Induced by Nep1-like Protein (NLP) of Moniliophthora perniciosa in Transgenic Tobacco"; MPMI; vol. 24, No. 7; 2011; pp. 839-848.
Chakraborty, Niranjan et al.; "Reduction of Oxalate Levels in Tomato Fruit and Consequent Metabolic Remodeling Following Overexpression of a Fungal Oxalate Decarboxylase1[W]"; Plant Physiology; vol. 162; May 2013; pp. 364-378.
Meynial-Sallers, Isabelle et al.; "In vitro glycosylation of proteins : an enzymatic approach"; Journal of Biotechnology; vol. 46; 1996; pp. 1-14.
Liu, Darrell Teh-Yung; "Glycoprotein pharmaceuticals : scientific and regulatory considerations, and the US Orphan Drug Act"; Feature; vol. 10; Apr. 1992; pp. 114-120.
Andersen, Dana C et al.; "The effect of cell-culture conditions on the oligosaccharide structures of secreted glycoproteins"; Current Opinion in Biology; vol. 5; 1994; ISSN 0958-1669; pp. 546-549.

\* cited by examiner

RECOMBINANT OXALATE DECARBOXYLASE EXPRESSED IN FILAMENTOUS FUNGI

CROSS REFERENCE TO THE RELATED APPLICATIONS

This application is the national phase entry of International Application No. PCT/CN2018/107053, filed on Sep. 21, 2018, which is based upon and claims priority to Chinese Patent Application No. 201810177819.3, filed on Mar. 5, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJHZ010_Sequence list_US_20200902.txt, dated Sep. 2, 2020 and is 77,042 bytes in size.

TECHNICAL FIELD

The present invention relates to the field of genetic engineering technology, specifically to a recombinant oxalate decarboxylase, a recombinant filamentous fungal host cell efficiently expressing oxalate decarboxylase, and a production method of the recombinant oxalate decarboxylase and uses thereof.

BACKGROUND

Oxalic acid, also named as ethanedioic acid, is a metabolite produced by biological organisms and exists widely as oxalate in plants, fungi, and bacteria. Many human and other mammalian foods, such as, e.g., spinach, strawberries, beet, cocoa, taro, sweet potato, rhubarb and tea contain high amounts of oxalate. Due to the lack of oxalate-degrading enzymes, oxalate is a terminal metabolite that cannot be eliminated by enzyme degradation in humans and other mammals. Oxalate derived from both exogenous dietary absorption and endogenous synthesis is excreted by the kidneys into the urine. Excess intake of oxalate derived from foods can easily lead to increased levels of oxalate in the urine and plasma and form insoluble calcium oxalate when combined with calcium. Calcium oxalate is the major constituent of calcium oxalate (CaOx) kidney stones. In addition, many other diseases have also been associated with excess oxalate, such as hyperoxaluria, cardiac conductance disorders, Crohn's disease and other enteric disease states. Therefore, it could reduce the risk of oxalate-related diseases including urinary calculi by reducing the absorption of oxalate via degradation of the dietary oxalate in vitro or in vivo.

In recent years, the study of enzymic degradation of oxalate to prevent CaOx stone and the other related diseases has been become a research focus. At present, there are three oxalate-degrading enzymes known in organisms: oxalate decarboxylase (hereinafter also referred to as "OxDC"), oxalate oxidase and oxalyl CoA decarboxylase. OxDC, a enzyme coordinating two essential manganese ions per subunit, catalyzes the decomposition of oxalate into carbon dioxide and formate and is mainly found in plants, bacteria, and fungi, such as, e.g., *Aspergillus niger, Coniothyriu mminitans, Flammulina velutipes, Trametes versicolor, Agaricusbisporus, Postia placenta, Bacillus subtilis, Agrobacterium tumefaciens*. However, the yield of OxDC in the above natural resources is very low, which leads to the high production cost and high market price and made it difficult to be widely and effectively commercialized.

Therefore, recombinant expression of OxDC is an inevitable choice to reduce the production cost so that it can be utilized commercially. At present, although the recombinant expression of OxDC derived from bacteria has been achieved in prokaryotic cells, such as OxDC derived from the YvrK gene of *Bacillus subtilis*. However, this OxDC derived from bacteria is unstable and inactive at low pH (lower than pH 3.0), while the pH in human stomach is often lower than 3.0. Moreover, OxDC from bacteria is easily digested by pepsin and loses its activity. Therefore, the scope, field and effectiveness of the application are significantly limited. In order to improve the performance of OxDC derived from bacteria, Allena Pharmaceutical Company prepared protein crystals from OxDC (PCT/US2007/075091) and crosslinked them with glutaraldehyde to improve their stability, and then made these crystals into oral medicament to degrade oxalate in the gastrointestinal tract. Clinical trials have shown that in patients with severe hyperoxaluria, oral high doses of the enzyme can only reduce urinary acid by 14% (Craig B. Langman, Am J Nephrol 2016; 44:150-158). Oxthera Company prepared another formulation, which mixed oxalic acid decarboxylase with acid-insoluble polymer, and was spray-dried to form a microparticle (Oxazyme, Oxthera Company). Clinical trials were paused at phase II, which suggested that Oxazyme had no effect on reducing urinary oxalate.

OxDCs derived from fungi can remain stable and resistant to pepsin at low pH, so it is very suitable for oral enzyme formulation to degrade oxalic acid. In spite of massive research efforts, the recombinant expression of OxDCs derived from fungi were not effective neither in prokaryotic expression system nor in eukaryotic expression system from the current public reports. The OxDC from *Flammulina velutipes* was the most studied. Meenu et al. (Meenu Kesarwani, et al. OxDC from *Collybia velutipes*, THE JOURNAL OF BIOLOGICAL CHEMISTRY, 2000) have expressed it by transgenic tobacco and tomato. The results showed that the enzyme activity could be observed, but the expression level was very low. At the same time, prokaryotic expression was also carried out, but the enzyme activity was not detected. Mohammad (Mohammad Azam, et al., A secretion signal is present in the *Collybia velutipes* OxDC gene, doi:10.1006; bbrc.2001.6049) expressed it in *Saccharomyces cerevisiae* and *Schizoderma cerevisiae*. The enzyme activity was not detected in *Saccharomyces cerevisiae*.

Although the enzyme activity was detected in *Schizogonia cerevisiae*, the expression level was very low and could not be used commercially.

SUMMARY

In order to solve the technical problems that OxDCs derived from fungi can not be recombinantly and effectively expressed in the art, a large number of experiments and efforts have been made in the early stage of the invention, including the use of different expression systems and the adoption of various biological methods. In the prokaryotic expression system, OxDC was tried to be recombinantly expressed in various prokaryotic cells, including *Escherichia coli, Bacillus subtilis, Bacillus licheniformis, Bacillus pumilus, Lactobacillus* and so on. And a lot of optimization work of expression elements and strategies had also been carried out. But no effective recombinant expression was achieved. In the eukaryotic expression system, OxDC was tried to be expressed in transiently or stably transformed tobacco and pea plants, suspension cultured tobacco cells, insect cells, *Saccharomyces cerevisiae* cells and *Pichia pastoris* cells. The result was that the enzyme activity was not detected, or the expression level was very low, and there was no possibility of industrial production. After a long and hard exploration and study, the inventors finally obtained high efficiency recombinant expression in filamentous fungi by combining and optimizing all the steps and links.

One objective of the invention is to provide a recombinant OxDC, which is recombinantly expressed in a filamentous fungal host cell. The form and degree of glycosylation modification of the recombinant OxDC is different from the OxDC expressed by the original host cell, and the recombinant OxDC expressed in the filamentous fungus host cell has the unique form and degree of glycosylation modification.

Recombinant OxDC maintains full or partial enzyme activity at pH 1.5-7.0. It can maintain not less than 10% relative enzyme activity at pH 1.5-2.5, and not less than 50% at pH 2.5-4.5, and not less than 25% at pH 4.5-7.0. Relative enzyme activity is defined as the percent activity observed as compared to maximum activity (set to 100%).

Optionally or preferably, the optimum pH of the recombinant OxDC is 2.5-3.5.

Optionally or preferably, the recombinant OxDC coding gene is derived from eukaryote, including but not limited to *Agrocybe aegerita, Agrocybe Cylindracea, Flammulina velutipes, Coriolus versicolor, Postia placenta, Aspergillus luchuensis, Agaricusbisporus* or *Tricholoma Lobayensc Heim* and so on.

Optionally or preferably, the recombinant OxDC comprises an amino acid sequence which has at least 60% identity, such as at least 65% identity, at least 70% identity, at least 75% identity, at least 80% identity, at least 85% identity, at least 90% identity, at least 95% identity to the amino acids 20 to 470 of SEQ ID NO: 1 or 5, or amino acids 25 to 472 of SEQ ID NO: 2, or amino acids 20 to 455 of SEQ ID NO: 3, or amino acids 21 to 447 of SEQ ID NO: 4, or amino acids 21 to 455 of SEQ ID NO: 6, or amino acids 25 to 440 of SEQ ID NO: 7, or amino acids 24 to 472 of SEQ ID NO: 8.

Preferably, the recombinant OxDC consists of the amino acids 20 to 470 of SEQ ID NO: 1 or 5, or amino acids 25 to 472 of SEQ ID NO: 2, or amino acids 20 to 455 of SEQ ID NO: 3, or amino acids 21 to 447 of SEQ ID NO: 4, or amino acids 21 to 455 of SEQ ID NO: 6, or amino acids 25 to 440 of SEQ ID NO: 7, or amino acids 24 to 472 of SEQ ID NO: 8.

The other objective of the invention is to provide a new and efficient method for recombinant expression of OxDC. The expression level and the total enzyme activity are much better than the previous methods, and reached the practical application value.

In order to achieve the above purpose, the first aspect of the present invention provides a recombinant filamentous fungal host cell, the chromosome DNA of the recombinant filamentous host cell containing a gene sequence encoding any of the above mentioned recombinant OxDC.

In particular, it comprises one or more copies of OxDC expression cassette integrated in its genome, which comprising a promoter, a signal peptide coding sequence, OxDC coding sequence and a transcription terminator.

After a lot of research, inventors have found that OxDC can be efficiently expressed and secreted out of the filamentous fungal host cells. OxDC expressed in the filamentous fungal host cells can undergo various post-translational modifications such as glycosylation modification, and the recombinant OxDC is similar to the OxDC prepared by natural host cells. Recombinant OxDC can be effectively secreted into the culture by adding a secreting signal peptide coding sequence to 5'-end of the coding sequence of OxDC. It is beneficial to the subsequent separation and purification and to reduce the production cost.

The signal peptide coding sequence refers to a signal peptide coding region that can direct the encoded OxDC into a specific cell region or secretory pathway. It can be obtained from but not limited to the genes for OxDC, *Trichoderma reesei* cellobiohydrolase I, *Trichoderma reesei* cellobiohydrolase II, *Trichoderma reesei* endoglucanase I, *Trichoderma reesei* endoglucanase II, *Aspergillus niger* neutral amylase, *Aspergillus niger* glucoamylase, *Aspergillus oryzae* TAKA amylase, *Humicola insolen* scelluase, *Humicolainsolens* endoglucanaseV, *Humicola lanuginosa* lipase, *Rhizomucor miehei* aspartic proteinase. Any signal peptide coding region capable of directing OxDC to the secretion pathway of the host cells of filamentous fungi can be used in the present invention. In some embodiments, the preferred signal peptide coding sequence is the signal sequence of *Trichoderma reesei* cellobiohydrolase I.

The promoter relates to a regulatory sequence associated with RNA polymerase binding to initiate OxDC gene transcription. The promoter may be any polynucleotide that has transcriptional activity in the host cell, and may be from genes that encode proteins either homologous or heterologous to the host cell. The promoter may be an inducible promoter or a constitutive promoter.

In the present invention, examples of promoters for directing transcription of OxDC expression cassette in the filamentous host cellare promoters obtained from, but are not limited to, genes for SV40, hCMV, CaMV 35S, *Aspergillus nidulans* acetamidase, *Aspergillus oryzae* alkaline protease, *Aspergillus oryzae* triose phosphate isomerase, *Aspergillus oryzae* TAKA amylase, *Aspergillus niger* neutral alpha-amylase, *Aspergillus niger* acid stable alpha-amylase, *Aspergillus niger* or *Aspergillus awarori* glucoamylase (glaA), *Rhizomucor miehei* lipase, *Trichoderma reesei* pyruvate decarboxylase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, or *Trichoderma reesei* beta-xylosidase, etc; And mutant, truncated, and hybrid promoters thereof.

In some preferable embodiments, the promoter is derived from the gene of *Trichoderma reesei* cellobiohydrolase I (CBHI), and in some preferable embodiments, the promoter is derived from the gene of *Trichoderma reesei* pyruvate decarboxylase gene (Ppdc).

The terminator is a sequence that can be recognized by a filamentous host cell to terminate transcription. Any terminator active in the host cell may be used in the present invention. In the present invention, examples of terminators for directing transcriptional termination of OxDC expression cassette in the filamentous host cell are terminators obtained from, but are not limited to, genes for *Aspergillus nidulans* acetamidase, *Aspergillus oryzae* alkaline protease, *Aspergillus oryzae* triose phosphate isomerase, *Aspergillus*

*oryzae* TAKA amylase, *Aspergillus niger* neutral alpha-amylase, *Aspergillus niger* acid stable alpha-amylase, *Aspergillus niger* or *Aspergillus awamori* glucoamylase (glaA), *Rhizomucormiehei* lipase, *Trichoderma reesei* pyruvate decarboxylase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, or *Trichoderma reesei* beta-xylosidase, etc.

In some preferable embodiments, the terminator is derived from the gene of *Trichoderma reesei* cellobiohydrolase I (CBHI), and in some preferable embodiments, the terminator is derived from the gene of *Trichoderma reesei* pyruvate decarboxylase gene (Ppdc).

Optionally or preferably, wherein the filamentous fungal host cell may be an *Aspergillus, Coriolus, Mucor, Phlebia, Acremonium, Cryptococcus, Fusarium, Humicola, Myceliophthora, Aureobasidium, Trametes, Pleurotus, Neurospora, Penicillium, Paecilomyces, Phanerochaete, Bjerkandera, Ceriporiopsis, Thielavia, Chrysosporium, Schizophyllum, Coprinus, Magnaporthe, Neocallimastix, Tolypocladium, Talaromyces, Thermoascus* or *Trichoderma* host cell, etc.

Optionally or preferably, wherein the filamentous fungal host cell may be an *Aspergillus niger, Aspergillus nidulans, Aspergillus oryzae* or *Aspergillus awamori* host cell of *Aspergillus* genus.

Optionally or preferably, wherein the filamentous fungal host cell may be a *Trichoderma harzianum, Trichoderma koningii, Trichoderma reesei, Trichoderma longibrachiatum* or *Trichoderma viride* host cell of *Trichoderma* genus.

More preferably, the filamentous fungal host cell may be a *Trichoderma reesei* host cell including, but not limited to, ATCC NO: 56765, ATCC NO: 13631, ATCC NO: 26921, ATCC NO: 56764, ATCC NO: 56767 and NRRL NO: 15709. In some embodiments, the filamentous fungal host cell may be a *Trichoderma reesei* strain Rut-C30 cell. In some embodiments, the filamentous fungal host cell can be variants of *Trichoderma reesei* strain Rut-C30, including genetic modifications that knock out many natural genes of the *Trichoderma reesei* host cell. These genes include pyr4, which encodes orotidine 5'-phosphate decarboxylase, and mus53, which is involved in the process of non-homologous recombination. The strain that knock out the pyr4 is a uridine auxotrophic strain. The selectable marker based on pyr4 mutant has been proved to be very effective and has been successfully applied in a variety of eukaryotic microorganisms. Knockout of the genes involved in the process of non-homologous recombination can significantly reduce the frequency of non-homologous recombination of *Trichoderma reesei* host cells and help to improve the screening of homologous recombination.

Optionally or preferably, at least 10% of the sequence encoding OxDC is optimized according to the codon preference of the filamentous fungal host cell. The optimized sequence encodes or at least partially encodes OxDC protein. The partial coding refers to deleting some amino acid sequences but also having the function of OxDC.

Optionally or preferably, the polynucleotides are selected from the polynucleotides of SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16; or are at least 50% identical with any of the SEQ ID NOs: 9-16, and more preferably, at least 60% identity, at least 70% identity, at least 80% identity, or at least 90% identity.

Of course, as known by someone skilled in the art, it is necessary to first construct the recombinant expression vector to be used for the preparation of the recombinant filamentous fungal host cell. The recombinant expression vector not only contains the expression cassette encoding OxDC, but also contains the expression cassette encoding a selectable marker.

The selective marker refers to a marker gene that can provide a simple selection of transformed host cells. Examples of suitable selective markers include, but are not limited to, resistant genes such as hygromycin and bar gene (Bar gene encode phosphinothricin acetyltransferase). Auxotrophic marker markers such as acetamidase (amdS), ornithine carbamyltransferase (Arg B) and orotidine-5'-phosphate decarboxylase can also be used.

The 5' flanking and 3' flanking of the expression cassette encoding selective marker have two 350-500 bp direct repeat fragments, which facilitate the removal of the selective marker by spontaneous DNA homologous recombination under selection pressure. In one embodiment, the selection marker is the pyr4 gene encoding orotidine-5'-phosphate decarboxylase, which is a key enzyme in the biosynthesis of pyrimidine nucleotides. The mutation of pyr4 gene will lead to the inhibition of pyrimidine nucleotides synthesis. Therefore, uridine auxotrophic strains lacking the enzyme can only grow in the presence of uracil or uridine. When the pyr4 gene is successfully transformed into the pyr4 gene-deficient strain, the expression of the pyr4 gene enabled the recipient strain to synthesize uracil/uridine itself, and thus to grow in the independent of uracil/uridine, and play a positive screening role. On the other hand, 5-fluoroorticacidoic acid (5-FOA) is toxic for the fungus in the presence of the pyr4 gene product, so wild-type strains can not grow in the presence of 5-FOA, but pyr4 gene-deficient strains showing 5-FOA resistance, so 5-FOA-mediated counter-selection provide a easy selection of transformed cells (Jeffrey L. Smith et al. CurrGenett, 1991, 19:27-23).

The recombinant expression vector includes random integrative expression vector and site-specific integrative expression vector. For example, the expression cassette encoding OxDC can be randomly integrated into the genome of *Trichoderma reesei* by *Agrobacterium*-mediated transformation, and its integrated position and copy number are analyzed by Tail-PCR method. In one embodiment, the transformed strains with different integration sites and copy numbers can be obtained by two rounds of transformation and screening, and enzyme production levels are compared by flask fermentation. A series of engineering strains were screened and the copy numbers and integration sites in *Trichoderma reesei* genome were analyzed separately. The site-specific integrative expression vector contained the 5' and 3' flanking regions of the target genes. Through site-specific integration, we can also knockout genes while importing OxDC expression cassettes to specific sites. In one embodiment, several cellulase genes (CBH1, CBH2, EG1 and EG2), which account for the main part of extracellular secreted proteins of *Trichoderma reesei*, were selected as site-specific integration sites. These loci can be knocked out at the same time as the OxDC expression cassette is integrated. Recombinant strain comprising four copies of OxDC expression cassette was constructed in this way. Under the fermentation condition, the content of OxDC secreted by recombinant strain could reach 90% in the total extracellular protein.

In a second aspect, the invention relates to methods for constructing a recombinant fungal host cell (random integration method) comprising one or more copies of OxDC expression cassette integrated in its genome. The OxDC expression cassette comprises a promoter, a signal peptide coding sequence, OxDC coding sequence and a terminator, and the method comprises the following steps:

S1: constructing at least one integrative expression vector comprising an expression cassette encoding a selectable marker and an expression cassette encoding OxDC.

S2: screening for transformants comprising one or more copies of OxDC expression cassette integrated in its genome after transformed into the host cell.

Optionally or preferably, the filamentous fungal host cell described in step S2 is artificial auxotroph cell. The integrative expression vector can repair the deficiency when integrated into the genome of the filamentous fungal host cell.

Optionally or preferably, the integrative expression vector was randomly integrated into its genome by non-homologous recombination after transformed into the host cell.

Optionally or preferably, the site-specific integrative expression vector contained the 5' and 3' flanking regions of the target genes. Thus, the expression vector can be integrated into the specific locus by homologous recombination after transformed into the host cell. Preferably, integrated into genes encoding extracellular proteins; even more preferably, integrated into genes that encode extracellular proteases or extracellular glycoside hydrolases; and most preferably, integration into CBH1 (cellobiohydrolase 1), CBH2 (cellobiohydrolase II), EG1 (endoglucanase I) or EG2 (endoglucanase 11) genes.

In one embodiment (random integration method), the original strain is a strain of Trichoderma reesei, which has been genetically modified by deletion of the pyr4 gene. The deletion contains the following steps:

At least one random integrated expression vector was constructed and transformed into Agrobacterium tumefaciens AGL-1 competent cell by freeze-thaw method; selecting for transformants containing the expression vector; co-cultured with spores of Trichoderma reesei (pyr4$^-$); screening for transformants comprising one or more copies of OxDC expression cassette. That is the target host cell.

A third aspect of the invention provides a medium for the culture of host cells prepared by the above method (random integration method). Its composition is as follows: glucose 3-8 g/L, microcrystalline cellulose 10-25 g/L, corn pulp powder 5-15 g/L, $(NH_4)_2SO_4$ 0.5-5 g/L, $MgSO_4 \cdot 7H_2O$ 1.56 g/L, $CaCl_2$ 0.5 g/L, $KH_2PO_4$ 2-8 g/L, urea 0-1 g/L, wheat bran 0.2-2 g/L, trace element (1000×) 1 ml, $MnCl_2$ 0.5-5 mM, pH 3.0-4.5.

A fourth aspect of the invention provides another method for constructing a recombinant filamentous fungal host cell (site-specific integration method). In one embodiment, the method comprises the following steps:

(4) Construction of OxDC expression vector targeted to CBH1, CBH2, EG1 and EG2 loci separately.

(5) The above expression vectors were transformed into a strain of Trichoderma reesei (pyr4$^-$, mus53$^-$). OxDC expression cassette replaced CBH1, CBH2, EG1 and EG2 loci respectively. After integration into these sites, the target protein accounted for the majority of the extracellular secretory protein, and it was more simple and economical for the recovery of OxDC from the nutrient medium. The probability of site-specific integration after mus53 gene knockout is greatly increased, which is helpful to the screening of site-specific integration strain.

(6) Pyr4 and mus53 gene repair vectors were used to repair the mus53 and pyr4 genes of the strain obtained from step 2. The successful repair strain was the target host cell. With the repair of pyr4 gene, there is no need to add uracil or uridine to the culture medium during fermentation. The host cells can preserve the inherent metabolic balance and do not increase the cost of fermentation. Repair of mus53 gene can preserve the inherent stability of host cell and eliminate the genomic instability caused by mus53 gene deletion.

A fifth aspect of the invention provides another medium suitable for the culture of the host cell prepared by the above method (site-specific integration method). Its composition is as follows: glucose 3-6 g/L, lactose 30-40 g/L, corn pulp powder 7-10 g/L, $(NH_4)_2SO_4$ 0.5-1 g/L, $MgSO_4 \cdot 7H_2O$ 1.56 g/L, $CaCl_2$ 0.5 g/L, $KH_2PO_4$ 2-4 g/L, urea 0-1 g/L, wheat bran 10-20 g/L, trace element (1000×) 1 ml, $MnCl_2$ 0.5-5 mM, pH 3.0-4.0.

A sixth aspect of the invention provides a method for producing recombinant OxDC, which includes the construction of OxDC expression cassette comprising a promoter, a signal peptide coding sequence, OxDC coding sequence and a terminator. The filamentous fungal host cell was transformed with the expression vector. One or more OxDC expression cassettes were integrated into the host cell genome, the host cell was cultured to express OxDC, and the expression product was purified from the host cell culture medium.

A seventh aspect of the invention provides the application of recombinant OxDC or the OxDC expressed by the recombinant filamentous fungal host cell in the preparation of medicine and food.

Optionally or preferably, the medicine is used for the prevention and/or treatment of urinary calculi.

An eighth aspect of the invention provides a drug composition for preventing or treating a disease with excessive urine oxalic acid, including OxDC prepared by the method.

Compared with the prior art, the invention has the following beneficial effects:

The invention overcomes the technical problem that the OxDC derived from fungi cannot be effectively expressed. Recombinant OxDC expressed by filamentous host cells can undergo various post-translation modifications. The highly secreted OxDC has similar enzymatic properties to the OxDC prepared by natural host cells. The method of culturing the host cells is simple, the secretion of OxDC is large and the activity of OxDC is high. Two fermentation media of the invention are respectively suitable for the two recombinant filamentous fungi host cells, and can effectively increase the yield. The production of OxDC, through the construction of expression cassettes, construction of vectors, construction of host cell and adjustment of final culture medium components, the yield and enzyme activity of the product was greatly improved. It effectively solves the problem that OxDC can not be produced on a large scale in the art, the enzymatic characteristics are unstable and the production cost is high.

DETAILED DESCRIPTION OF THE EMBODIMENTS

Examples

Figure 1:
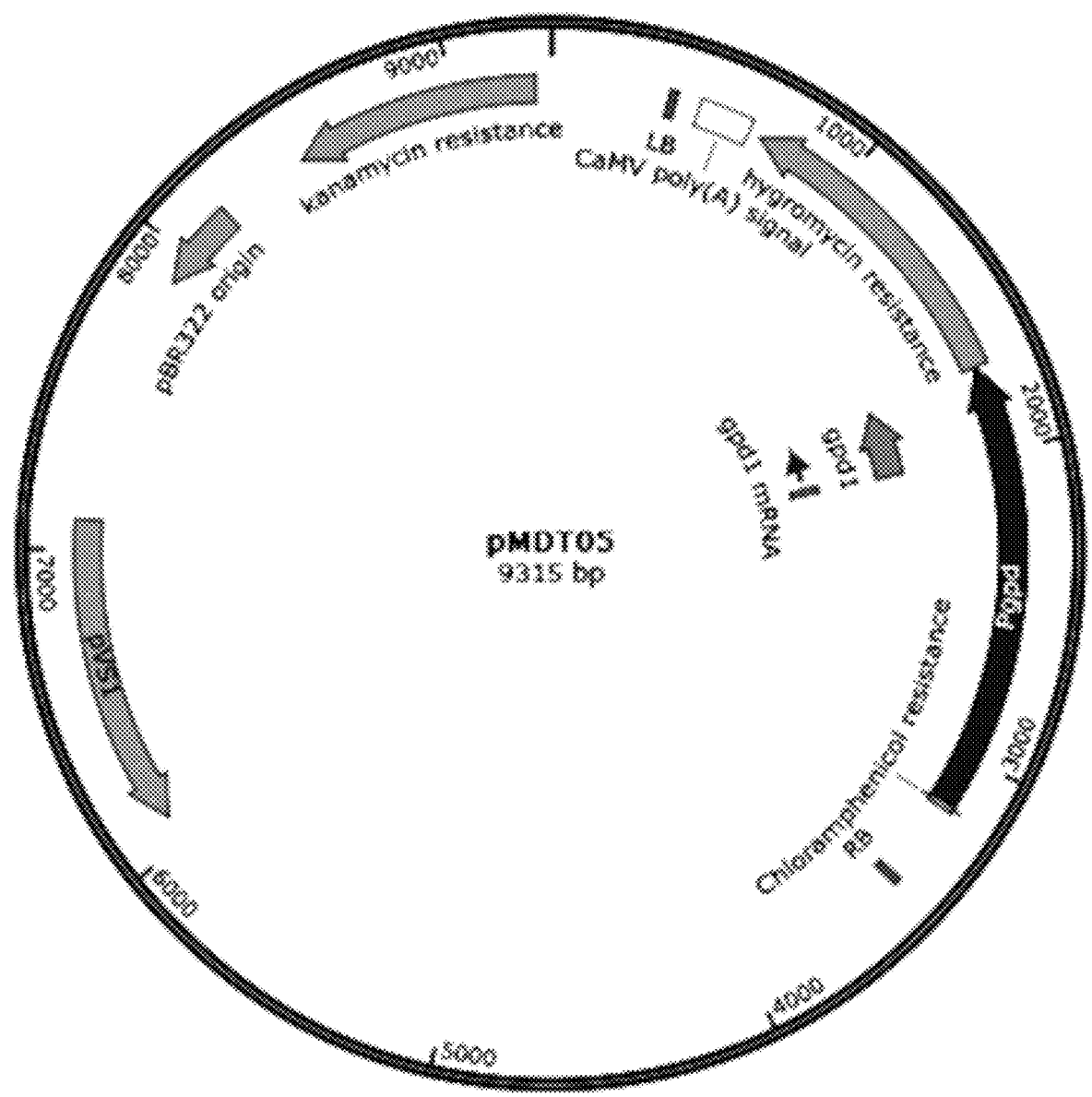
FIG. 1 shows a schematic drawing of the plasmid pMDT05.

The present invention is described by a specific embodiment of recombinant expression of OxDC derived from *Agrocybe aegerita* in *Trichoderma reesei*, so that those skilled in the art better understand the invention and be able to implement it. However, the cited embodiments do not qualify the invention.

Except as specifically indicated, the technical terms used are commonly used by those skilled in the art. The experimental methods which do not specify the specific conditions herein are routine experimental methods. The test materials and reagents used herein are all commercially available. The ingredients and preparation methods of various reagents and media are routine experimental procedures.

The *Trichoderma reesei* Rut-C30 (ATCC 56765) used in the present invention is purchased from a Guangdong Culture Collection center.

The *Aspergillus Niger* CICC2439 used in the invention is purchased from China Center of Industrial Culture Collection.

Example 1: Codon Optimization and Synthesis of OxDC Gene

After a lot of research, inventors have found that OxDC derived from eukaryotes can be expressed by filamentous fungal expression system. Preferred sources include, but are not limited to, *Agrocybe aegerita, Agrocybe Cylindracea, Flammulina velutipes, Coriolus versicolor, Postia placenta, Aspergillus luchuensis, Agaricusbisporus* or *Tricholoma Lobayensc Heim*.

The nucleotide sequence encoding OxDC can be derived from *Agrocybe aegerita*, wherein the OxDC comprises the amino acid sequence of SEQ ID NO: 1, the signal peptide comprises the amino acid sequence of amino acids 1 to 19 of SEQ ID NO: 1, the mature peptide comprises the amino acid sequence of amino acids 20 to 470 of SEQ ID NO: 1.

The OXDC gene derived from *Agrocybe aegerita* optimized according to the code usage of *Trichoderma reesei* (Codon Usage Database: *Hypocrea jecorina*). The optimized nucleotide sequence coding mature peptide of OXDC is artificially synthesized. Compared to the original nucleotide sequence, the CAI (Codon Adaptation Index) of optimized nucleotide sequence increased from 0.51 to 0.99. GC content increased from 53.09% to 69.23%. The optimized nucleotide sequence is SEQ ID NO: 17. The optimized nucleotide encoding the mature peptide of OXDC is renamed TRA2.

Example 2: Construction of Auxotrophic pyr4 Mutant of *Trichoderma reesei* Rut-C30

The filamentous fungal host cell used in recombinant expression of eukaryotic OXDC may be, including but not limited to, an *Aspergillus, Coriolus, Mucor, Phlebia, Acremonium, Cryptococcus, Fusarium, Humicola, Myceliophthora, Aureobasidium, Trametes, Pleurotus, Neurospora, Penicillium, Paecilomyces, Phanerochaete, Bjerkandera, Ceriporiopsis, Thielavia, Chrysosporium, Schizophyllum, Coprinus, Magnaporthe, Neocallimastix, Tolypocladium, Talaromyces, Thermoascus* or *Trichoderma* cell, or the sexual or synonymous type thereof.

The *Trichoderma* host cell may be a *Trichoderma harzianum, Trichoderma koningii, Trichoderma reesei, Trichoderma longibrachiatum* or *Trichoderma viride* cell. The present invention is illustrated by an example of *Trichoderma reesei*.

5. *Trichoderma reesei* Genomic DNA Extraction

*Trichoderma reesei* Rut-C30 (ATCC 56765) was inoculated on potato dextrose agar (PDA) plates and cultured at 28° C. for 7 days until the spores matured. The spores were eluted with sterile water. The appropriate amount of spore suspension was prepared and inoculated in 20 ml of liquid medium, and cultured at 28'C, 170 rpm for 36-48 hours. The hyphae were washed with ddH$_2$O, and harvested onto filter paper by vacuum filtration. Harvested hyphae, and ground into fine powder by freezing liquid nitrogen. Genomic DNA was isolated by Sangon Biotech Ezup column genomic DNA extraction kit.

PDA medium: peeled potato slice 200 g, boiled with 1000 ml water for 30 minutes and 8 layers of gauze filter, the filtrate supplemented with glucose 20 g, supplemented with water to 1 L, natural pH, 2% Agar powder, autoclave-sterilized at 115° C. for 30 min.

The liquid medium: glucose 15 g/L, yeast extract 20 g/L, $(NH_4)_2SO_4$ 2.5 g/L, $MgSO_4 \cdot 7H_2O$ 0.8 g/L, $CaCl_2$) 1.0 g/L, pH to 4.8.

6. Construction of Plasmid pMDT05

The PCR amplification reaction was performed using pCAMBIA1300 plasmid as template with primers pMDT05-F1 and pMDT05-R1 (Table 1). The PCR products were separated by 1% agarose gel electrophoresis where an approximately 6.8 kb fragment was excised from the geland extracted using an OMEGA gel extraction kit according to the protocol listed in the manual. The purified fragment was digested with restriction endonuclease XhoI and XbaI for 1 hour, and then purified and recovered using an OMEGA PCR purification kit.

The promoter Pgpd (about 1.4 kb) was amplified from the *Trichoderma reesei* strain genomic DNA using primers Hyg-Pgpd-F and pMDT05-R2 (Table 1). The hygromycin gene (about 1 kb) was amplified from the plasmid pCAMBIA1300 with primers pMDT05-F2 and Pgpd-Hyg-R (Table 1). The two fragments of the promoter Pgpd and the hygromycin gene were mixed as template at 1:1 in molar ratio, and the primers pMDT05-F2 and pMDT05-R2 were used as the forward and reverse primers for SOE-PCR amplification (The PCR reaction was carried out as follows: 94° C. for 10 minutes, then 30 cycles of amplification (98° C. for 10 seconds, 60° C. for 30 seconds, 68° C. for 1 minutes 20 seconds), then 68° C. for 10 minutes.) to obtain the fusion fragment of 2.4 kb. The PCR products were separated by 1% agarose gel electrophoresis where an approximately 2.4 kb fragment was excised from the gel and extracted using an OMEGA gel extraction kit according to the protocol listed in the manual. The purified fragment was digested with restriction endonuclease XhoI and XbaI for 1 hour, and then purified and recovered using an OMEGA PCR purification kit.

The digested 6.8 kb and 2.4 kb fragments (at 1:3 in molar ratio) were mixed with T4 DNA ligase and ligation buffer, and ligated together at 22° C. for 3 hours. The ligation product was transformed into *Escherichia coli* TOP10 competent cells. Transformants were cultured on LB plus kanamycin (50 μg/ml) plates and screened by colony PCR using pMDT05-F2 and pMDT05-R2 primers and sequencing. The correct plasmid vector was named pMDT05 (FIG. 1).

TABLE 1

Sequences of the Primers used for Construction of pMDT05 Plasmid

| Primers | Primer sequences (5'-3') |
| --- | --- |
| pMDT05-F1 | SEQ ID NO: 18 |
| pMDT05-R1 | SEQ ID NO: 19 |
| Hyg-Pgpd-F | SEQ ID NO: 20 |
| pMDT05-R2 | SEQ ID NO: 21 |
| pMDT05-F2 | SEQ ID NO: 22 |
| Pgpd-Hyg-R | SEQ ID NO: 23 |

7. Construction of a Pyr4 Gene Deletion Plasmid pMDT05-Pyr4 KO

According to the pyr4 gene information provided in the public literature (Jeffrey L. Smith, Curr Genet, 1991. 19:27-33), the BLASTN program was used to search the locus sequence information of pyr4 gene in the database of *Trichoderma reesei* genome. 1.3 kb upstream and 1.3 kb downstream flanking sequences of the pyr4 gene were amplified with primer combinations pyr4-3F/pyr4-3R and pyr4-5F/pyr4-5R (Table 2), respectively. Genomic DNA of *Trichoderma reesei* was used as template. The two PCR products were mixed at 1:1 in molar ratio and used as template, and the primers pyr4-3F and pyr4-5R were used as the forward and reverse primers for SOE-PCR amplification to obtain the 2.6 kb pyr4 gene deletion cassette.

Figure 2:
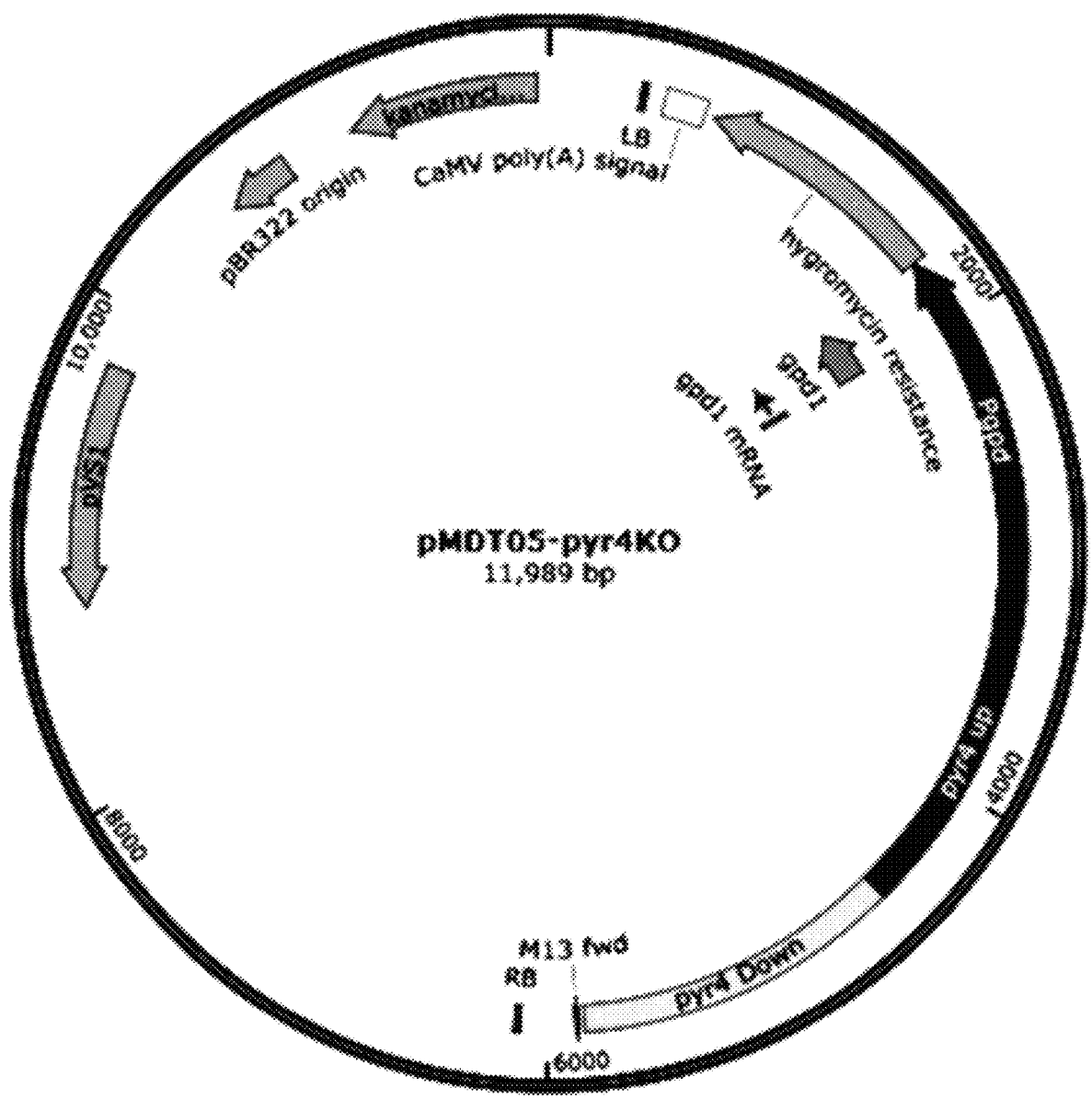
FIG. 2 shows a schematic drawing of the plasmid pMDT05-pyr4 KO.

The pMDT05 vector and the 2.6 kb pyr4 gene deletion cassette were digested with XbaI and BglII for 1 hour, and the digested fragments were recovered using an OMEGA gel extraction kit, separately, and then mixed with T4 DNA ligase and ligation buffer, and ligated together at 22° C. for 3 hours. The ligation product was transformed into *Escherichia coli* TOP10 competent cells. The recombinant vector that verified by sequencing correctly was named pMDT05-pyr4 KO (FIG. 2).

8. Construction of Pyr4 Gene Deletion Mutant of *Trichoderma reesei* by *Agrobacterium tumefaciens*

The recombinant pMDT05-pyr4 KO was transformed into *Agrobacterium tumefaciens* AGL-1 competent cells by freeze-thaw method. After incubated with shaking at 28° C. for 3 to 4 hours, appropriate amount of cells were spread onto the LB agar plate containing 50 μg/mL kanamycin and 50 μg/mL gentamicin. After cultured at 28° C. for 48 to 72 hours, the transformants were selected and inoculated in LB liquid medium containing 50 μg/mL kanamycin and 50 μg/mL gentamicin, and cultured with 220 rpm at 28° C. for 24 hours. Positive transformants were screened by colony PCR Preparation of *Agrobacterium tumefaciens* for transformation: The identified positive transformant was inoculated into LB liquid medium containing 50 μg/mL kanamycin and 50 μg/mL gentamicin, and incubated with 220 rpm at 28° C. for 20-24 hours. The bacteria cells were collected and washed twice with liquid induction medium (IM), see Example 4 for recipe, and diluted to OD600=0.15-0.20 in IM media with the presence of 200 μM acetosyringone (AS). The cells were grown for 6-10 hours at 28° C., with shaking at 200 rpm, to the OD600=0.6-0.8.

Preparation of *Trichoderma reesei* recipient Spores: the spores of *Trichoderma reesei* were washed with 4-5 ml of sterile water from the PDA plates cultured for 6-7 days. A spore suspension was prepared by cotton filtration. Then the spores were collected by centrifugation, and washed with IM medium twice. The spore concentration was adjusted to $10^7$/ml in IM medium, and germinated at 28° C. for 3-4 hours.

Co-incubation of *Agrobacterium tumefaciens* and *Trichoderma reesei*: 100 μL of the *Trichoderma reesei* germinated spores were mixed with an equal volume of *A. tumefaciens* cells, spreaded on the surface of a cellophane, and placed horizontally on solid IM plates, co-cultivated at 24° C. for 36 hours in the dark. The cellophanes were transferred to the solid MM medium plates containing 5 mg/ml 5-FOA, 300 μg/mL cefotaxime and 10 mM uridine, and then incubated at 28° C. for 4-6 days until the putative transformants appeared.

Transformants screening: A single transformant was simultaneously picked and transferred to the PDA solid plate containing 100 μg/mL hygromycin and the solid MM medium plate containing 5 mg/ml 5-FOA and 10 mM uridine, separately. Cultured at 28'C for 2 to 3 days, the transformants which could not grow on the solid PDA plate containing 100 μg/mL hygromycin but could grow normally on the solid MM medium plate containing 5 mg/ml 5-FOA and 10 mM uridine were selected. Genomic DNA of the transformant was extracted. PCR validation was performed with specific primer pyr4-CX-F and pyr4-CX-R (Table 2) annealing to the region on either side of the homologous arm. If the pyr4 gene is knocked out, the amplified fragment should be about 2.8 kb, and if not, the amplified fragment should be about 4.2 kb.

In this embodiment, 23 transformants (#1-#23) were screened by PCR amplification, and all the transformants could be amplified to obtain an approximately 2.8 kb PCR product. One of the transformants could grow normally on the PDA solid plate containing 100 μg/mL hygromycin and on the solid MM medium plate containing 5 mg/ml 5-FOA and 10 mM uridine. This indicated that the transformant contained the homologous recombination replacement and also the random integration insertion at the same time. Therefore, the effective knockout rate of pyr4 gene was 95.6%.

Isolation of single spore: the transformant 8# was picked and transferred to a PDA plate containing 10 mM uridine and incubated at 28° C. for 7 days until the spores matured. The mature spores were washed with 4-5 ml of sterile water, diluted with sterile water gradient, then spread on the PDA plate containing 10 mM uridine and 0.1% Triton-100, and cultured at 28° C. for 3 days. The spore isolates were picked up and cultured at 28° C. in PDA medium plate containing 10 mM uridine. The isolated single spore colony and PCR positive strain was named as Rut-C30 (pyr4-).

TABLE 2

Sequence of the Primers used for pyr4 Gene Deletion

| Primers | Primer sequences (5'-3') |
|---|---|
| pyr4-3F | SEQ ID NO: 24 |
| pyr4-3R | SEQ ID NO: 25 |
| pyr4-5F | SEQ ID NO: 26 |
| pyr4-5R | SEQ ID NO: 27 |
| pyr4-CX-F | SEQ ID NO: 28 |
| pyr4-CX-R | SEQ ID NO: 29 |

Example 3: Construction of a Randomly Integrated Recombinant Expression Vector for OxDC 3. Construction of Randomly Integrated Inducible Expression Vector pMGU-cbh1-TRA2 Construction of Vector pMGU:

The backbone of plasmid pMDT05, approximately 6.6 kb, was amplified using the forward and reverse primers F1 and R1. The PCR products were separated by 1% agarose gel electrophoresis. The target fragment was recovered and digested with DpnI for 3 hours. The digested fragment was recovered and reserved.

The genomic DNA was extracted from *Aspergillus Niger* stain CICC2439 according to the procedure described in Example 2. An approximately 2.9 kb of pyrG gene expression cassette was amplified from the *Aspergillus Niger* genome using primers pyrG-F and pyrG-R. The target fragment was recovered by the gel purification and reserved. A partial 0.4 kb fragment of CBHI gene promoter Pcbh1 was amplified from the *Trichoderma reesei* genome using primers Pcbh-DR-F and Pcbh-DR-R, recovered by the gel purification and reserved. The two gel-purified fragments were mixed at 1:1 in molar ratio and used as template, and the primers Pcbh-DR-F and pyrG-R were used as the forward and reverse primers for SOE-PCR amplification to obtain the 3.3 kb fusion fragment. The SOE-PCR protocols were as following: 94° C. for 10 minutes, then 30 cycles of amplification (98° C. for 10 seconds, 60° C. for 30 seconds, 68° C. for 1 minutes 50 seconds), then 68° C. for 10 minutes. The fusion fragment was recovered by the gel purification and reserved.

The 3.3 kb fusion fragment was cloned into digested pMDT05 backbone fragment using a ClonExpress II one-step cloning kit. The reaction was transformed into *E. coli* TOP10 competent cells, and spread onto the LB agar plate containing 50 μg/mL kanamycin. The recombinant vector that verified by sequencing was named pMGU.

Construction of inducible expression cassette pUC19-Pcbh1-sig-TRA2-Tcbh1: The fragment Pcbh1-sig containing the CBH1 gene promoter and the signal peptide coding sequence was amplified from the *Trichoderma reesei* genome using primers Pcbh1-F and Pcbh1-R. The terminator Tcbh1 was amplified from the *Trichoderma reesei* genome using primers Tcbh1-F and Tcbh1-R. The two fragments were combined by SOE-PCR reaction using primers Pcbh1-F and Tcbh1-R The approximately 3.3 kb fusion fragment Pcbh1-sig-Tcbh1 was digested with EcoRI and PstI, and then recovered by the gel purification. The plasmid pUC19 was digested with EcoRI and PstI for 3 hours, and then recovered by the gel purification. The digested fragment Pcbh1-sig-Tcbh1 was ligated into the digested pUC19 using T4 DNA ligase. The ligation products were transformed into *E. coli* TOP10 competent cells. The recombinant plasmid that verified by sequencing was named pUC19-Pcbh1-sig-Tcbh1.

An approximately 5.8 kb was amplified from plasmid pUC-Pcbh1-sig-Tcbh1 using primers WF-CBH-R and WF-CBH-F (Table 3). The PCR products were digested with DpnI for 3 hours, and then recovered by the gel purification. The mature peptide coding sequence of TRA2 gene was amplified from plasmid pUC57-TRA2 (provided by Gene Synthesis Company) using primers WF-TRA2-F and WF-TRA2-R (Table 3). The TRA2 gene fragment and the digested 5.8 kb fragment were ligated together using a ClonExpress II one-step cloning kit, and then transformed into *E. coli* TOP10 competent cells. The recombinant plasmid that verified by sequencing was named pUC19-Pcbh1-sig-TRA2-Tcbh1.

Figure 3:
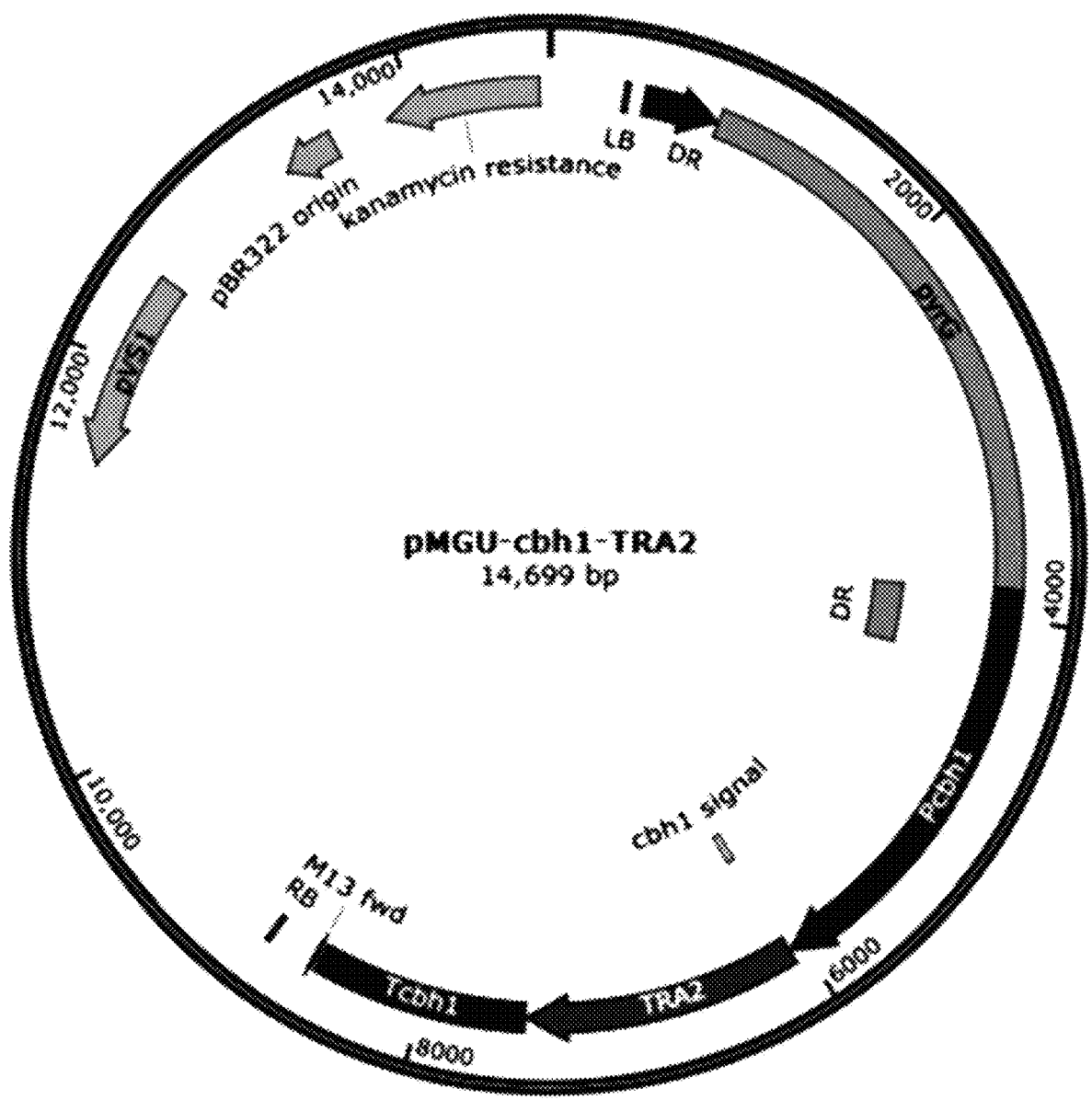
FIG. 3 shows a schematic drawing of the plasmid pMGU-cbh1-TRA2.
Figure 4:
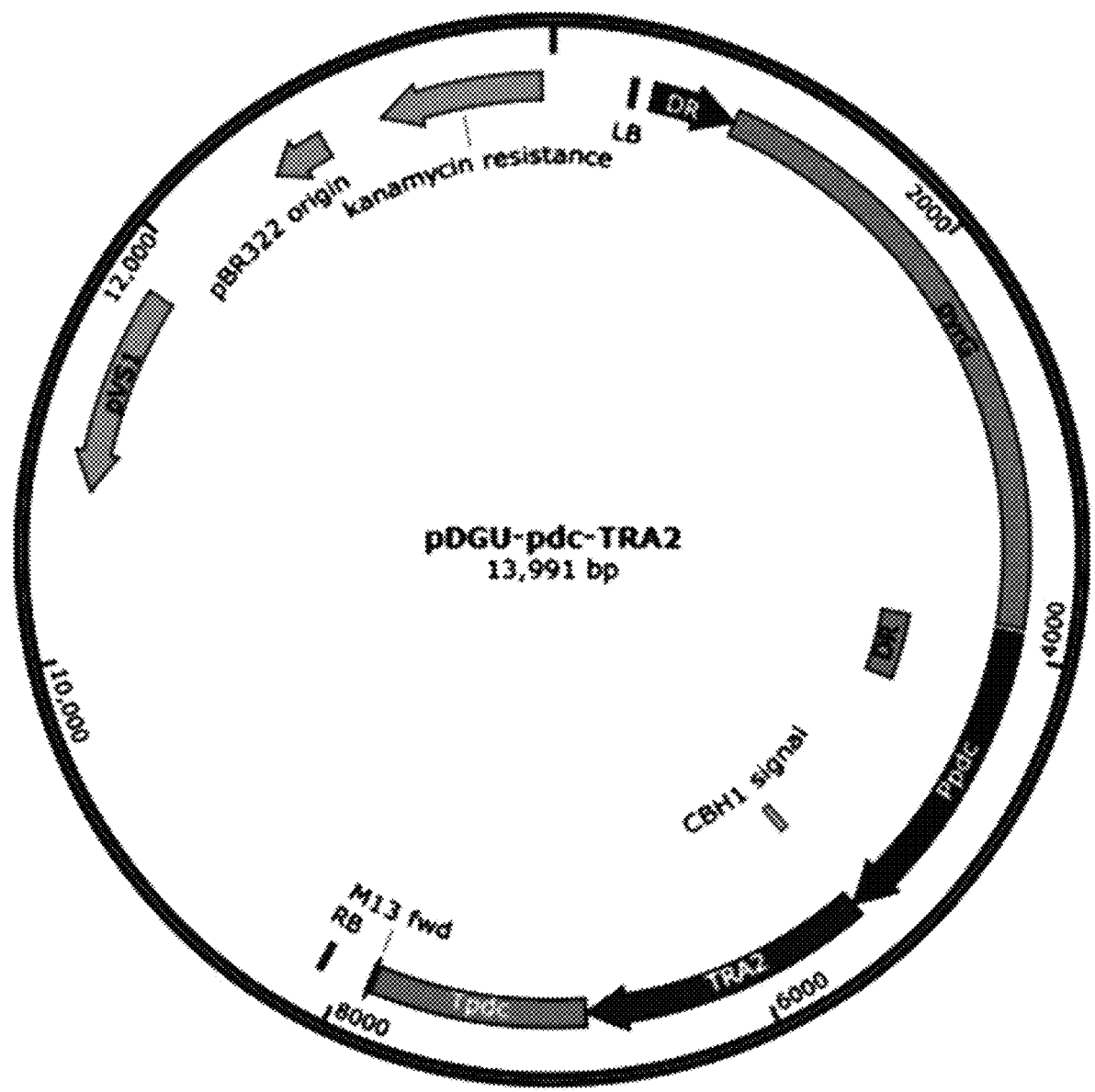
FIG. 4 shows a schematic drawing of the plasmid pDGU-pdc-TRA2.
Figure 5:
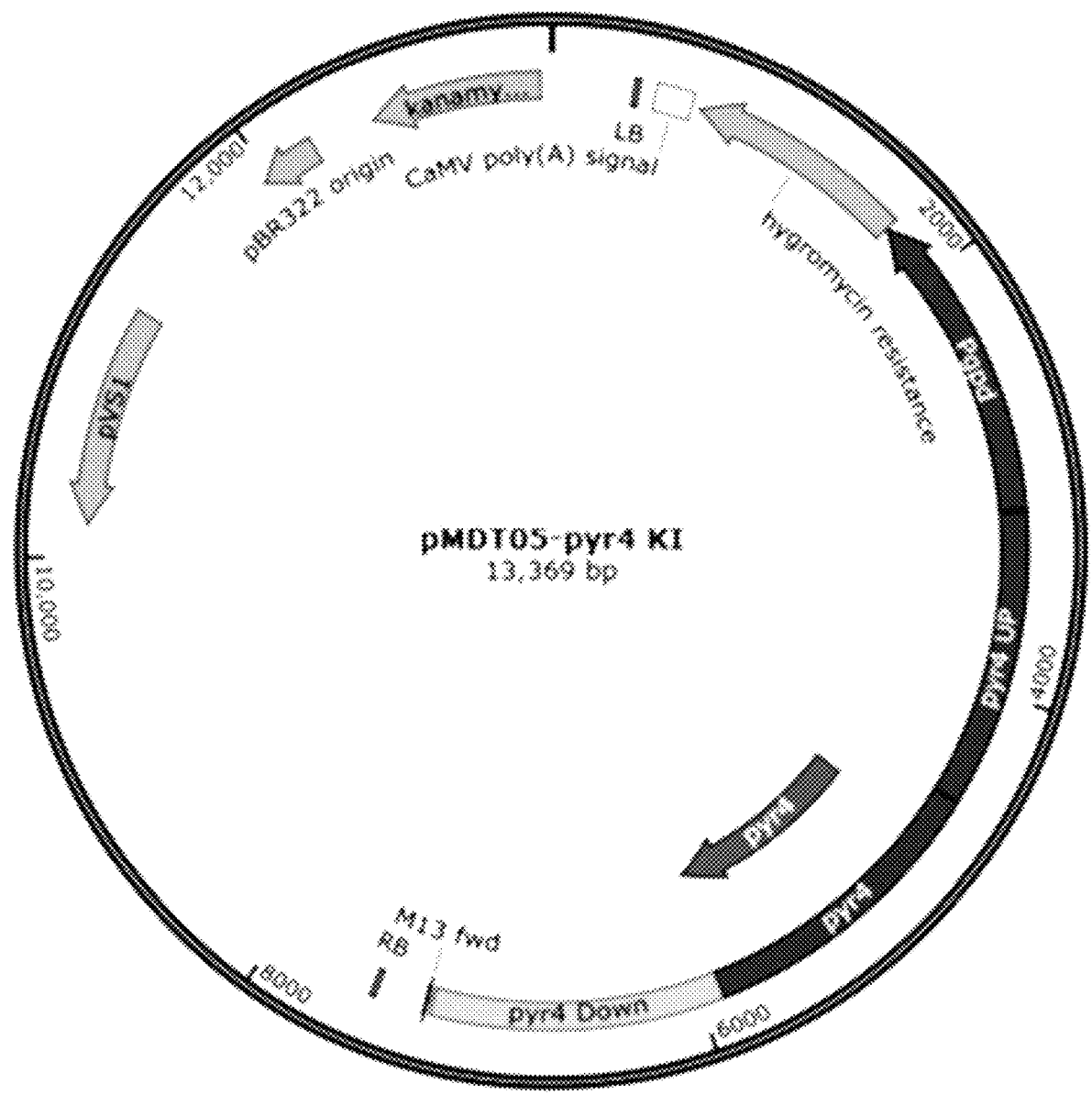
FIG. 5 shows a schematic drawing of the plasmid pMDT05-pyr4 KI.

Construction of randomly integrated inducible expression vector pMGU-cbh1-TRA2: The plasmid pMGU was digested with EcoRI and XbaI for 3 hours, and then recovered by the gel purification. The fragment Pcbh1-sig-TRA2-Tcbh1 was amplified from plasmid pUC19-Pcbh1-sig-TRA2-Tcbh1 using primers F2 and R2 (Table 3), and then recovered by the gel purification. The purified fragment Pcbh1-sig-TRA2-Tcbh1 was cloned into the digested pMGU above using a ClonExpress II one-step cloning kit, and then transformed into *E. coli* TOP10 competent cells. The recombinant plasmid that verified by sequencing was named pMGU-cbh1-TRA2 (FIG. 3).

4. Construction of Randomly Integrated Constitutive Expression Vector pDGU-Pdc-TRA2.

Construction of plasmid pDGU: An approximately 6.6 kb backbone fragment was amplified from plasmid pDGU using primers F1 and R1, and then digested with DpnI for 3 hours, recovered by the gel purification.

The 2.9 kb pyrG expression cassette was amplified from the *Aspergillus Niger* CICC2439 genomic DNA using primers pdcDR-pyrG-F and pyrG-R (Table 3), and then recovered by the gel purification. The 0.4 kb 5' end fragment of the promoter Ppdc of pdc gene was amplified from *Trichoderma reesei* genomic DNA using primers Ppdc-DR-F and pyrG-pdcDR-R (Table 3), and then recovered by the gel purification. The 2.9 kb pyrG expression cassette and the 0.4 kb fragment were combined by SOE-PCR reaction using primers Ppdc-DR-F and pyrG-R The 3.3 kb fusion fragment was recovered by the gel purification.

The 3.3 kb fusion fragment was cloned into the digested backbone of pDGU using a ClonExpress II one-step cloning kit, and then transformed into *E. coli* TOP10 competent cells. The recombinant plasmid that verified by sequencing was named pDGU.

Construction of constitutive expression cassette pUC19-Pcbh1-sig-TRA2-Tcbh1: The promoter Ppdc, approximately 1.4 kb, was amplified from *Trichoderma reesei* genomic DNA using primers NdeI-Pdc-F and Ppdc-R (Table 3). The terminator Tpdc, approximately 1.0 kb, was amplified from *Trichoderma reesei* genomic DNA using primers. The two fragments were combined by SOE-PCR reaction using primers NdeI-Pdc-F and PstI-Tpdc-R. The 2.5 kb fusion fragment Ppdc-Tpdc was digested with NdeI and PstI, and then recovered by the gel purification. The digested fragment Ppdc-Tpdc was cloned into the NdeI and PstI sites of the plasmid pUC19, yielding recombinant plasmid pUC19-Ppdc-Tpdc.

An approximately 5.0 kb backbone fragment was amplified from plasmid pUC19-Ppdc-Tpdc using primers WF-pdc-R and WF-pdc-F, and digested with DpnI, recovered by the gel purification. An approximately 1.4 kb fragment sig-TRA2 was amplified from plasmid pUC19-Pcbh1-sig-TRA2-Tcbh1 using primers WF-TRA2-F2 and WF-TRA2-R2 (Table 3). The two fragments were ligated together using a ClonExpress II one-step cloning kit, and then transformed into *E. coli* TOP10 competent cells. The recombinant plasmid that verified by sequencing was named pUC19-Ppdc-sig-TRA2-Tpdc.

Construction of randomly integrated constitutive expression vector pDGU-pdc-TRA2: Plasmid pDGU was digested by XbaI for 3 hours, and then partially digested by EcoRI for 5 minutes. The larger backbone of pDGU was recovered by the gel purification. The fragment Ppdc-sig-TRA2-Tpdc was amplified from plasmid pUC19-Ppdc-sig-TRA2-Tpdc using primers F3 and R3, and then recovered by the gel purification. The fragment Ppdc-sig-TRA2-Tpdc was cloned into and the purified backbone of pDGU using a ClonExpress II one-step cloning kit, and then transformed into *E. coli* TOP10 competent cells. The recombinant plasmid that verified by sequencing was named pDGU-pdc-TRA2 (Table 3).

TABLE 3

Sequence of the Primers used for the expression vectors construction

| Primers | Primer sequences (5'-3') |
| --- | --- |
| F1 | SEQ ID NO: 30 |
| R1 | SEQ ID NO: 31 |
| pyrG-F | SEQ ID NO: 32 |
| pyrG-R | SEQ ID NO: 33 |
| Pcbh-DR-F | SEQ ID NO: 34 |
| Pcbh-DR-R | SEQ ID NO: 35 |
| Pcbh1-F | SEQ ID NO: 36 |
| Pcbh1-R | SEQ ID NO: 37 |
| Tcbh1-F | SEQ ID NO: 38 |
| Tcbh1-R | SEQ ID NO: 39 |
| WF-CBH-R | SEQ ID NO: 40 |
| WF-CBH-F | SEQ ID NO: 41 |
| WF-TRA2-F | SEQ ID NO: 42 |
| WT-TRA2-R | SEQ ID NO: 43 |
| F2 | SEQ ID NO: 44 |
| R2 | SEQ ID NO: 45 |
| Ppdc-DR-F | SEQ ID NO: 46 |
| pdcDR-pyrG-F | SEQ ID NO: 47 |

TABLE 3-continued

Sequence of the Primers used for the expression vectors construction

| Primers | Primer sequences (5'-3') |
| --- | --- |
| pyrG-pdcDR-R | SEQ ID NO: 48 |
| NdeI-Pdc-F | SEQ ID NO: 49 |
| Ppdc-R | SEQ ID NO: 50 |
| Tpdc-F | SEQ ID NO: 51 |
| PstI-Tpdc-R | SEQ ID NO: 52 |
| WF-TRA2-F2 | SEQ ID NO: 53 |
| WF-TRA2-R2 | SEQ ID NO: 54 |
| WF-pdc-R | SEQ ID NO: 55 |
| WF-pdc-F | SEQ ID NO: 56 |
| F3 | SEQ ID NO: 57 |
| R3 | SEQ ID NO: 58 |

Example 4: Construction of a Recombinant *Trichoderma reesei* Expressing OxDC by Random Integration The two randomly integrated recombinant expression vectors pMGU-cbh1-TRA2 and pDGU-pdc-TRA2 in Example 3 above were transferred into *Agrobacterium tumefaciens* AGL-1 competent cells by freeze-thaw method separately. The positive clones verified by PCR were used to prepare *Agrobacterium tumefaciens* cells for transformation according to the procedure described in Example 2.

Preparation of *Trichoderma reesei* recipient Spores: the spores of *Trichoderma reesei* Rut-C30 (pyr4⁻) were washed with 4-5 ml of sterile water from the PDA plates (containing 10 mM uridine) cultured for 6-7 days. A spore suspension was prepared by cotton filtration. Then the spores were collected by centrifugation and washed with IM medium twice. The spore concentration was adjusted to $10^7$/ml in IM medium, and germinated at 28° C. for 3-4 hours.

Co-incubation of *Agrobacterium tumefaciens* and *Trichoderma reesei*: 100 μL of the *Trichoderma reesei* germinated spores were mixed with an equal volume of *A. tumefaciens* cells, spread on the surface of a cellophane, and placed horizontally on solid IM plates, co-cultivated at 24° C. for 36 hours in the dark. The cellophanes were transferred to the solid MM medium plates containing 300 μg/mL cefotaxime, and then incubated at 28° C. for 4-6 days until the putative transformants appeared. In this embodiment, the recombinant expression vector pMGU-cbh1-TRA2 was transformed into *Trichoderma reesei* Rut-C30 (pyr4⁻) strain genome in 3 copies and 230 transformants were obtained. The recombinant expression vector pDGU-pdc-TRA2 was transformed into *Trichoderma reesei* Rut-C30 (pyr4⁻) strain genome in a single copy and 73 transformants were obtained.

Transformants screening: All the transformants were picked and transferred to MM plates, see media recipe below, containing 300 μg/mL cefotaxime and incubated at 28° C. for 2-3 days. The transformants with normal growth rate and morphology were transferred to PDA plates and cultured at 28° C. for 7 days. After the spores matured, the spore suspension was prepared by washing the spores with sterile water, and then the spores were diluted in gradient. Spread on the PDA plates containing 0.1% Triton-100, and cultured at 28° C. for 3 days until single spore isolates appeared on the plates. Three single spore isolates were selected and cultured on PDA medium at 28° C. for 3 days, and then a small amount of mycelium was picked out and heated at 98° C. for 10 minutes in 1.5 ml Eppendorf tube containing 20 μL of sterile water. The supernatant of centrifugation was identified by PCR with primers TRA2-F and TRA2-R. The single spore isolates identified as positive by PCR were cultured until the spores matured for 7 days.

The sequences of primers identified by PCR were as follows (5'-3'):

```
TRA2-F:
ATGTATCGGAAGTTGGCCCGTCATC (amino acids 16-39 of SEQ ID NO: 53)

TRA2-R:
TTAGGCAGGGCCGACGACAATAGG (amino acids 16-39 of SEQ ID NO: 54)
```

The IM media: $K_2HPO_4$ 10 mmol/L, $KH_2PO_4$ 10 mmol/L, NaCl 2.5 mmol/L, $MgSO_4 \cdot 7H_2O$ 2 mmol/L, $CaCl_2$ 0.7 mmol/L, $(NH_4)_2SO_4$ 4 mmol/L, Glucose 10 mmol/L, Glycerol 0.5%, AS 200 μmol/L, Mandels trace element (1000×) 1 ml/L, pH 5.3.

The MM media: glucose 20 g/L, peptone 2 g/L, $(NH_4)_2SO_4$ 5 g/L, $MgSO_4 \cdot 7H_2O$ 0.6 g/L, $CaCl_2$ 0.6 g/L, $KH_2PO_4$ 15 g/L, Mandels trace element (1000×) 1 ml/L, pH 4.5-5.5.

Example 5: Expression Screening of Randomly Integrated Transformants in Shake Flask Fermentation The mature spores of the isolates in Example 4 above were washed with 4-5 ml of sterile water and inoculated at 1% (v/v) into the liquid seed culture medium. After cultured at 28'C for 24 hours, the seed culture was inoculated at 10% (v/v) into expression medium suitable for different promoters. The activity of OxDC in supernatant of fermentation broth was analyzed after 168 hours incubation at 28'C, 170 rpm.

Liquid seed culture medium: glucose 15 g/L, peptone 2 g/L, $(NH_4)_2SO_4$ 2.5 g/L, $MgSO_4 \cdot 7H_2O$ 0.8 g/L, $CaCl_2$ 1.0 g/L, 50 mM citrate buffer solution (pH 4.5), urea 0.3 g/L, $KH_2PO_4$ 2 g/L, Mandels trace element (1000×) 1 ml/L, 1-2 g/L Tween-80, pH 4.5.

The expression media for inducible promoter: lactose 18 g/L, microcrystalline cellulose 10 g/L, corn steep powder 12 g/L, $(NH_4)_2SO_4$ 0.5 g/L, $MgSO_4 \cdot 7H_2O$ 1 g/L, $CaCl_2$ 1.0 g/L, $KH_2PO_4$ 6 g/L, wheat bran powder 2 g/L, Mandels trace element (1000×) 1 ml/L, $MnCl_2$ 5 mM, pH 4.5.

Mandels trace element (1000×): $FeSO_4 \cdot 7H_2O$ 5 g/L, $MnSO_4$ 1.6 g/L, $ZnSO_4 \cdot 7H_2O$ 1.7 g/L, $CoCl \cdot 6H_2O$ 3.7 g/L.

The expression media for constitutive promoter: glucose 50 g/L, peptone 4.5 g/L, $(NH_4)_2SO_4$ 1.4 g/L, $MgSO_4 \cdot 7H_2O$ 0.3 g/L, $CaCl_2$ 0.4 g/L, 50 mM citrate buffer solution (pH 4.5), urea 0.3 g/L, $KH_2PO_4$ 2 g/L, Mandels trace element (1000×) 1 ml/L, Tween-80 1-2 g/L, pH 4.5.

One unit of enzyme activity (IU) was defined as the amount of enzyme required to degrade 1 μmol oxalic acid per minute or to produce 1 μmol formic acid per minute at 37° C. and pH 3.0. All the transformants were screened for enzyme production by shake flask fermentation. The highest activity of OxDC expressed by inducible promoter reached 17940 IU/L after 168 hours of fermentation. The highest enzyme activity of OxDC expressed by constitutive promoter reached 8800 IU/L after 168 hours of fermentation.

Example 6: Optimization of Fermentation Conditions in Shake Flasks

The present embodiment optimized the effects of different carbon and nitrogen sources in the initial culture medium and their concentrations on the expression of OxDC in the inducible recombinant strain. The results showed that the OxDC activity in supernatant of fermentation broth was about 3000 IU/L with unoptimized fermentation medium (composition: lactose 18 g/L, microcrystalline cellulose 10 g/L, corn steep powder 12 g/L, $(NH_4)_2SO_4$ 0.5 g/L, $MgSO_4 \cdot 7H_2O$ 1.56 g/L, $CaCl_2$) 0.5 g/L, $KH_2PO_4$ 6 g/L, wheat bran powder 2 g/L, Mandels trace element (1000×) 1 ml/L, $MnCl_2$ 5 mM, pH 4.0). The optimal medium with initial glucose concentration of 8 g/L and microcrystalline cellulose 23 g/L was the best. The activity of OxDC in supernatant could reach 50876 IU/L after 168 hours of fermentation in shake flask. The optimal medium composition was: glucose 3-8 g/L, microcrystalline cellulose 10-25 g/L, corn steep powder 5-15 g/L, $(NH_4)_2SO_4$ 0.5-5 g/L, $MgSO_4 \cdot 7H_2O$ 1.56 g/L, $CaCl_2$ 0.5 g/L, $KH_2PO_4$ 2-8 g/L, wheat bran powder 0.2-2 g/L, Mandels trace element (1000×) ml/L, $MnCl_2$ 0.5-5 mM, pH 3.0-4.5.

Example 7: Analysis of Flanking Sequences of Insertion Sites of Random Integrative Transformants Genomic DNAs of *Trichoderma reesei* transformants were extracted according to the method in Example 2. The flanking sequences of T-DNA insertion sites in transformants were analyzed by TD-TAIL PCR (Touchdown TAIL-PCR) (Song Gao et al. Analytical Biochemistry, 59 (2016) 9-81). Random primers LAD1-LAD5 and specific primers AC1, RB-1, RB-2 and Tail-CX-F were used in present embodiment (see Table 4). Among these degenerate primers, V stands for A/G/C, N stands for A/G/C, B stands for G/C/T, D stands for A/G/T, H stands for A/C/T.

TABLE 4

| Sequence of the Primers used in TD-TAIL-PCR | |
|---|---|
| Primers | Primer sequences (5'-3') |
| LAD1 | SEQ ID NO: 59 |
| LAD2 | SEQ ID NO: 60 |
| LAD3 | SEQ ID NO: 61 |
| LAD4 | SEQ ID NO: 62 |
| LAD5 | SEQ ID NO: 63 |
| AC1 | SEQ ID NO: 64 |
| RB-1 | SEQ ID NO: 65 |
| RB-2 | SEQ ID NO: 66 |
| Tail-CX-F | SEQ ID NO: 66 |

The Pre-amplification reaction was composed of 20-30 ng of genomic DNA, 1.0 μM anyone of primer LADs, 0.3 μM RB-1, 200 μM dNTPs, 2 μl 10× buffer, 0.5 U Taq DNA polymerasein a final volume of 20 μl.

Pre-amplification cycling conditions were as follows:

(g) 93° C., 120 s (h) 95° C., 60 s (i) 94° C., 30 s; 60° C., 60 s; 72° C., 180 s; 10 cycles (j) 94° C., 30 s; 25° C., 120 s; Ramping to 72° C., 150 s; 72° C., 180 s (k) 94° C., 20 s; 58° C., 60 s; 72° C., 120 s; 25 cycles (l) 72° C., 300 s Touch-down PCRreaction was composed of 2 μl of 50-fold diluted PCR fragment from the pre-amplification, 0.3 μM AC1, 0.3 μM RB-1, 200 μM dNTPs, 5 μl 10× buffer, 1 U Taq DNA polymerase in a final volume of 50 μl.

The amplification parameters in Touch-down PCR were as follows:
(e) 94° C., 120 s
(f) 94° C., 20 s; 68° C. (−1° C./cycle), 60 s; 72° C., 180 s; 15 cycles
(g) 94° C., 20 s; 53° C., 60 s; 72° C., 180 s; 15 cycles
(h) 72° C., 300 s In this embodiment, thirty-five transformants with activity of 25000-65000 IU/L were selected for flanking sequence analysis of T-DNA insertion sites. Among all the obtained flanking sequences of T-DNA, and six of them contained about 0.5 kb vector sequences outside RB boundary, the insertion sites on the genome were not identified. Forty-two T-DNA flanking sequences were identified on the genome. Among the forty-two T-DNA flanking sequences, eight had complete RB boundary sequences and thirty-four T-DNA right boundary sequences had partial deletion.

Thirty-five transformants were further analyzed by PCR. Twenty-five of the thirty-five transformants were deduced to be single copy T-DNA insert, five transformants were deduced to have two copies at the same site and existed as direct repeat, and three transformants were deduced to have two copies at the same site and existed as inverted repeat, two transformants were deduced to have a single copy at the two different sites.

In the thirty-five transformants, the enzyme activity of the transformants comprising two copied was 60%-100% higher than that comprising a single copy, which showed a good dose-response. In the subsequent isolation of single spores and in parallel fermentation experiments, it was found that the transformants comprising two direct repeat copies were unstable, and the activities of the enzyme in shake flask fermentation among the single spore colonies isolated from the same transformant were quite different. Under the same fermentation conditions, the enzyme activity of most of them was lower than that of the parent. The single spores isolated from the transformant comprising two inverted repeat copies at the same site showed good parallelism in fermentation, equivalent to the parent, under the same fermentation conditions. One single spore isolation of the transformants with high enzyme activity (≥50000 IU/L), comprising two inverted repeat copies at the same site, was named B4-6. TD-TAIL-PCR and sequencing analysis showed that the insertion site of strain B4-6 was between Trire2 scaffold_12:102924-105333.

Example 8: Deletion of Selective Marker Gene pyrG from *Trichoderma reesei* Transformants Strain B4-6 was inoculated on PDA medium (containing 10 mM uridine) and cultured at 28° C. for 7 days until the spores matured. Spores suspension was prepared by washing spores with 4-5 ml of sterile water. A suitable amount of spore suspension was spread on PDA medium containing 0.1% Trinton-100, 5 mg/ml 5-FOA and 10 mM uridine, and cultured at 28° C. for 4-5 days until the single colonies appear. About 100 colonies resistant to 5-FOA were obtained. Five 5-FOA resistant colonies were transferred to PDA medium containing 10 mM uridine and cultured at 28° C. for 7 days until the spores matured. Then, the purified candidate single spore isolations were identified through PCR with primers pyrG-F2 and pyrG-R2 to ensure the pyrG gene excision by spontaneous homologous recombination. The results showed that the pyrG expression cassette had been removed from all the five spore isolates.

```
Primer pyrG-F2 (SEQ ID NO: 67):
5'-TTATAGTATTAGTTTTCCGCCGAC-3'

Primer pyrG-R2 (SEQ ID NO: 68):
5'-ATCTCCTCCAAGTCGCGATTGAC-3'
```

One of the five isolations with the excision of the pyrG marker was B4-6(pyr4⁻).

Example 9: Construction of Transformants Comprising Multiple Copies by Transformation of Strain B4-6(Pyr4⁻) with Random Integrated Expression Vector pMGU-cbh1-TRA2

The expression vector pMGU-cbh1-TRA2 was transformed into strain B4-6 (pyr4⁻) by *Agrobacterium*-mediated transformation method described in Example 4. About forty-two transformants were obtained and transferred to solid MM medium plates containing 300 μg/mL cefotaxime, and cultured at 28° C. for 3 days. Thirty-nine of them grown normally were selected and transferred to PDA plate and cultured at 28° C. for 7 days.

All thirty-nine transformants were screened by PCR with primers pyrG-F3 and WF-CBH-R to confirm the addition of new copies.

A small amount of mycelium was picked out from the PDA plate cultured for 3 days and heated at 98° C. for 10 minutes in 20 μl of sterile water. The supernatant was identified by PCR with primers pyrG-F3 and WF-CBH-R. The positive transformants could amplify an approximately 2.3 kb fragments.

```
Primer pyrG-F3 (SEQ ID NO: 69):
5'-TTACTTGGGTGTTCTCAGCTTG-3'
```

The sequence of primer WF-CBH-R is shown in Table 2.

Figure 6:
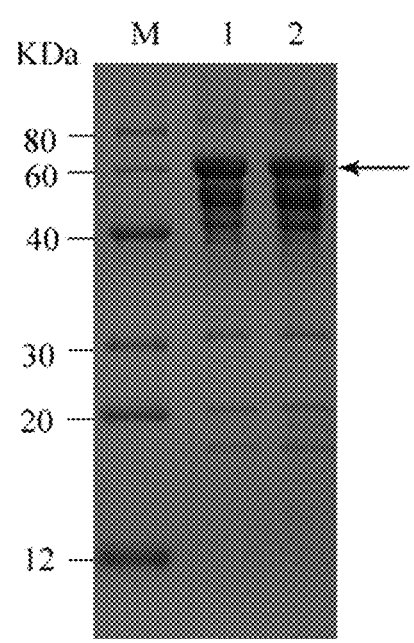
FIG. 6 shows a picture of SDS-PAGE analysis of the culture supernatants; Lane 1 is Protein Maker; Lane 2 is supernatant collected after 144 h of fermentation; Lane 3 is supernatant collected after 168 h of fermentation. The arrow head indicates a recombinant OxDC band.

All the transformants were screened by shake flask fermentation using the optimized medium in Example 6. The enzyme activity was measured every 24 hours from 72 hours until the end of fermentation at 168 hours. The results showed that the highest activity of #26 transformant could reach to 103951 IU/L after 168 hours of fermentation. The supernatants of fermentation broth of 144 hours and 168 hours were diluted 5 times, separately, and detected by SDS-PAGE. The result was as shown in FIG. 6. Lane 1 and 2 stands for 144 h and 168 h supernatant of fermentation broth, respectively. The loading amount was 10 μl per well. The new copy insertion site of the highest transformants was analyzed using the method described in Example 7. Sequencing analysis showed that there was a new copy insertion at two different sites, respectively. The insertion sites were Trire2 scaffold_7:1288320-1288321 and Trire2 scaffold_1:1129134-1129157. The selective marker gene pyrG was removed by the method described in Example 8 and the resulting stain was named HH03-26-8(pyr4⁻).

Example 10: Repair of the Pyr4 Gene in Strain HH03-26-8(Pyr4⁻)

An approximately 4.0 kb fragment comprising the pyr4 expression cassette and the flanking sequences was amplified from Rut-C30 genomic DNA using primers pyr4-F1 and pyr4-R1. The PCR products were separated by 1% agarose gel electrophoresis where the target fragment was excised from the gel and extracted by the gel purification. The purified fragment was digested with BglII and XbaI for 1 hour, and then recovered using a PCR product purification kit. The plasmid pMDT05 was digested with BglII and XbaI for 3 hours, and then recovered by the gel purification. The purified 4.0 kb fragment was ligated into the digested pMDT05 using T4 DNA ligase. The ligation products were transformed into E. coli TOP10 competent cells. The positive clones were screened by PCR and verified by sequencing. The vector verified by sequencing was named pMDT05-pyr4 KI.

```
Primer pyr4-F1 (SEQ ID NO: 70):
5'-TCAGATCTAGTGTTTGATGCTCACGCTCGGAT-3'

Primer pyr4-R1 (SEQ ID NO: 71):
5'-TTTCTAGATGAACAGTAAGGTGTCAGCA-3'
```

The expression vector pMDT05-pyr4 KI was transformed into strain HH03-26-8(pyr4$^-$) according to the procedure described in Example 8. About 153 transformants were obtained and transferred to MM solid plates, and then cultured at 28° C. for 48 hours. The mycelium would grow outward to a diameter of about 1 cm. All the transformants on the MM plates were numbered and picked and transferred to the PDA solid plates containing 100 μg/mL hygromycin, and cultured at 28° C. for 48 hours. About 35 transformants could not grow on the PDA solid plates containing 100 μg/mL hygromycin. These transformants were picked from MM solid plates and transferred to PDA plates, then cultured at 28° C. At the third day of culture, a small amount of mycelium was heated at 98° C. for 10 minutes in 20 μl of sterile water. The supernatants were obtained by centrifugation, and used for PCR verification using primers pyr4-F2 and pyr4-R2.

```
Primer pyr4-F2 (SEQ ID NO: 72):
5'-CAAACGAACACATCACTTTCAAAG-3'

Primer pyr4-R2 (SEQ ID NO: 73):
5'-GTGGGCTTCCTTGTTTCTCGACC-3'
```

When homologous recombination occurred at the pyr4 locus to repair the pyr4 expression cassette, the amplified band was about 4.2 kb. When no homologous recombination occurred, the amplified band was about 2.7 kb. The results of PCR analysis showed that 28 of the 35 transformants amplified about 4.2 kb fragments, and 7 of the 35 transformants amplified about 2.7 kb fragments. It was speculated that the repair plasmid pMDT05-pyr4 KI was randomly inserted outside the pyr4 locus and lost their hygromycin resistance at the same time in these seven transformants.

Example 11: Mus53 Gene Knockout in Strain Rut-C30 (Pyr4$^-$)

According to the published literature (Matthias G. Steiger, APPLIED AND ENVIRONMENTAL MICROBIOLOGY, January 2011, p. 114-121), mus53 gene (homologous to human Lig4 gene) is required for the non-homologous end joining (NHEJ) DNA repair pathway. Disrupting the NHEJ pathway improves locus specific integration of DNA. In the present embodiment, the mus53 gene of strain Rut-C30 (pyr4−) was knocked out to lay a foundation for subsequent site-specific integration.

3. Construction of Mus53 Gene Knockout Vector pMDT05-mus53KO

According to the mus53 gene (Protein Id: 58509) information provided in the public literature (Matthias G. Steiger, APPLIED AND ENVIRONMENTAL MICROBIOLOGY, January 2011, p. 114-121), the search program was used to get the locus sequence information of mus53 gene in the database of *Trichoderma reesei* genome.

Approximately 1.4 kb 3' flanking sequence and 1.3 kb 5' flanking sequence of mus53 gene were amplified from strain Rut-C30 genomic DNA using primer pairs mus53-3F/mus53-3R and mus53-5F/mus53-5R, separately. An approximately 1.3 kb middle fragment of mus53 gene was amplified using primers mus53-mid-F and mus53-mid-R.

An approximately 1.5 kb pyr4 gene coding region plus terminator sequence was amplified from strain Rut-C30 genomic DNA using primers pyr4-TprC-F and pyr4-R A 386 bp promoter PtrpC was amplified from plasmid pBARGPE1 using primer pyr4-F and pyr4-TrpC-R.

The five PCR fragments above were recovered using an OMEGA PCR purification kit, separately, and then mixed as PCR template. An approximately 6.1 kb fusion fragment was amplified using primers mus53-3R and mus53-mid-F, and then recovered using an OMEGA PCR purification kit.

Figure 7:
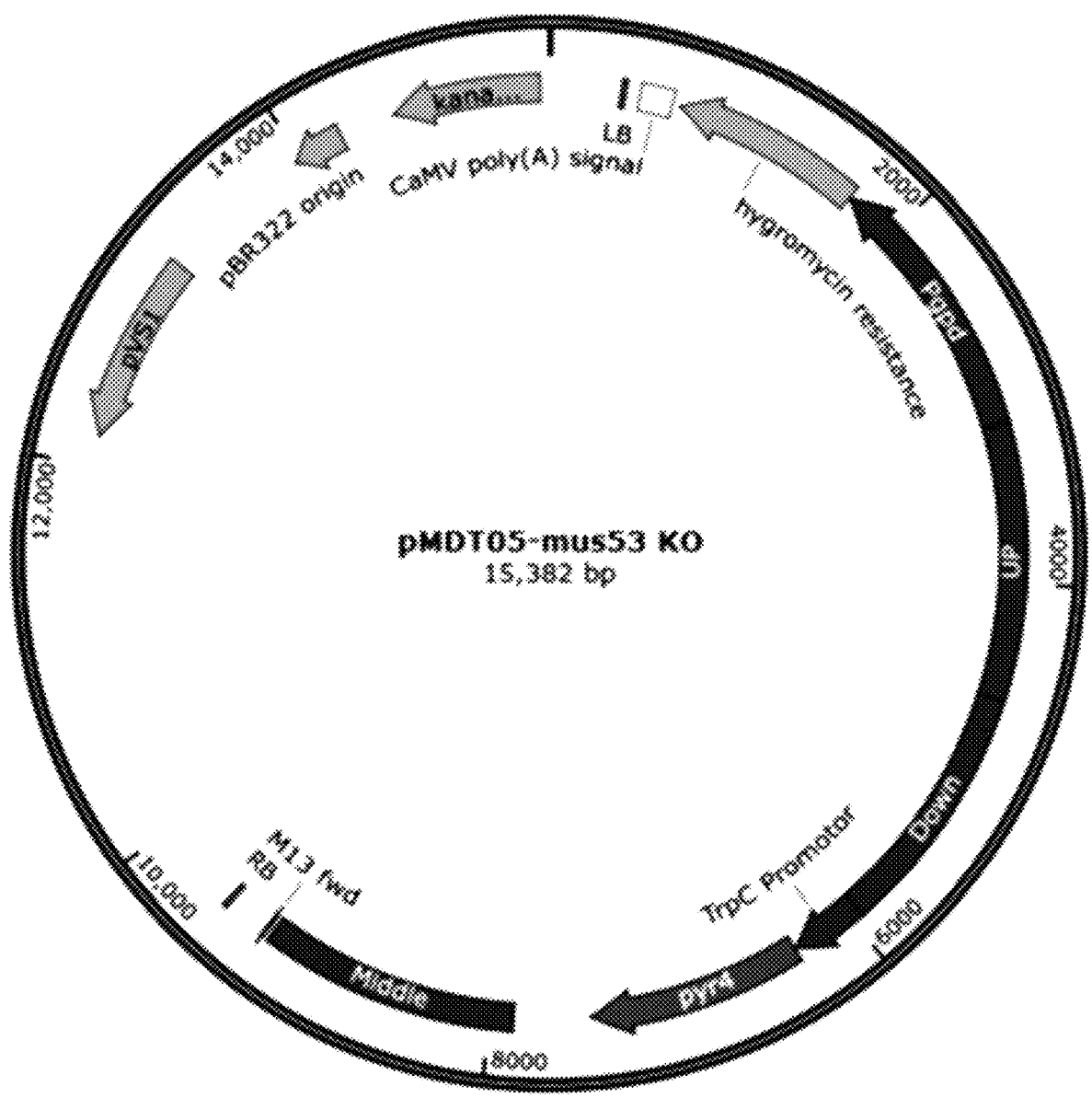
FIG. 7 shows a schematic drawing of the plasmid pMDT05-mus53KO.

The plasmid pMDT05 was digested with EcoRI and XbaI for 3 hours, and then recovered by gel purification. The 6.1 kb fusion fragment was cloned into EcoRI/XbaI digested pMDT05 using a ClonExpress II one-step cloning kit, and then transformed into E. coli TOP10 competent cells. The recombinant plasmid that verified by sequencing was named pMDT05-mus53KO (FIG. 7).

4. Mus53 Gene Knockout in *Trichoderma reesei* Rut-C30 (Pyr4$^-$)

The knockout vector pMDT05-mus53KO was transformed into strain Rut-C30 (pyr4$^-$) by *Agrobacterium*-mediated transformation described in Example 4. About 294 transformants were obtained, and each one was picked and transferred simultaneously to solid MM plates (containing 300 μg/mL cefotaxime and 200 μg/mL hygromycin) and solid MM plates (300 μg/mL cefotaxime), and then cultured at 28° C. for 3 days. Forty-four non-hygromycin resistant transformants were obtained, and thirty-one of them were transferred to PDA plates and cultured at 28° C. for 7 days.

All thirty-one transformants were screened by PCR with primers pairs MUS-F/TrpC-CX-F and pyr4-LB-R/MUS-R to determine whether homologous recombination occurred between the UP region and the Middle region at the mus53 gene locus. Primers RB-YZ-F and RB-YZ-R were used to amplify and screen the transformants to determine whether random integration occurred outside the locus of mus53 gene.

In the present embodiment, for each of the transformants, a small amount of mycelium cultured for 3 days on a PDA plates was picked and heated at 98° C. for 10 minutes in 20 μl of sterile water, the supernatant was centrifuged to serve as a template. The primer pairs MUS-F/TrpC-CX-F and pyr4-LB-R/MUS-R could amplify about 3.1 kb and 1.6 kb fragments respectively, indicating that correct homologous recombination took place in the corresponding regions, and 425 bp fragment could not be amplified using primers RB-YZ-F and RB-YZ-R, which indicated that no random integration had taken place. Fifteen positive transformants satisfying these conditions were screened in this embodiment. One of the positive transformants was inoculated on PDA medium (containing 10 mM uridine) and cultured at 28° C. for 7 days until the spores matured. The spore suspension was prepared by washing the spores with 4-5 ml of sterile water. A suitable amount of spore suspension was spread on PDA plate containing 5 mg/ml 5-FOA, 0.1% Trinton-100 and 10 mM uridine and cultured at 28° C. for 4-5 days until the single colonies appeared. Three of the colonies were transferred to PDA plates containing 10 mM uridine and cultured at 28° C. for 7 days until the spores matured. The colonies with excision of pyr4 expression cassette were identified by PCR with primers MUS-F and MUS-R. The colony with excision of pyr4 gene could be amplified an approximately 2.9 kb fragment. The results showed that the pyr4 expression cassette had been removed in all the three colonies. The positive strain was named Rut-C30(pyr4−, mus53−).

TABLE 5

Sequence of the Primers used in mus53 Gene Deletion

| Primers | Primer sequences (5'-3') |
| --- | --- |
| mus53-3R | SEQ ID NO: 74 |
| mus53-3F | SEQ ID NO: 75 |
| mus53-5R | SEQ ID NO: 76 |
| mus53-5F | SEQ ID NO: 77 |
| mus53-mid-R | SEQ ID NO: 78 |
| mus53-mid-F | SEQ ID NO: 79 |
| pyr4-R | SEQ ID NO: 80 |
| pyr4-F | SEQ ID NO: 81 |
| pyr4-TprC-F | SEQ ID NO: 82 |
| pyr4-TrpC-R | SEQ ID NO: 83 |
| MUS-F | SEQ ID NO: 84 |
| TrpC-CX-F | SEQ ID NO: 85 |
| Pyr4-LB-R | SEQ ID NO: 86 |
| MUS-R | SEQ ID NO: 87 |
| RB-YZ-F | SEQ ID NO: 88 |
| RB-YZ-R | SEQ ID NO: 89 |

Example 12: Construction of Site-Specific Integration Expression Vectors

5. Construction of CBHI Site-Specific Integration Expression Vector pMDT05-CBHI-TRA2 (KI)

A Search program was performed to obtain the locus sequence information of CBH1 (Cel7A) gene in the database of *Trichoderma reesei* genome.

A fragment Pcbh1-TRA2-Tcbh1 containing partial Pcbh1 sequence was amplified from plasmid pMGU-cbh1-TRA2 using primers CBH-F1 and CBH1-R1, in which the 1115 bp part of Pcbh1 was used as 5' flanking homologous region. A 500 bp fragment of 3' end of Tcbh1 Terminator amplified from *Trichoderma reesei* genomic DNA using primers CBHI-F2 and CBH1-R2 was used as the repeat sequence. The pyr4 expression cassette was amplified from plasmid pMDT05-mus53KO using primers CBHI-F3 and CBH-R3. A 1041 bp fragment adjacent to the Tcbh1 terminator amplified from *Trichoderma reesei* genomic DNA using primers CBH1-F4 and CBH1-R4 was used as 3' flanking homologous region.

Figure 8:
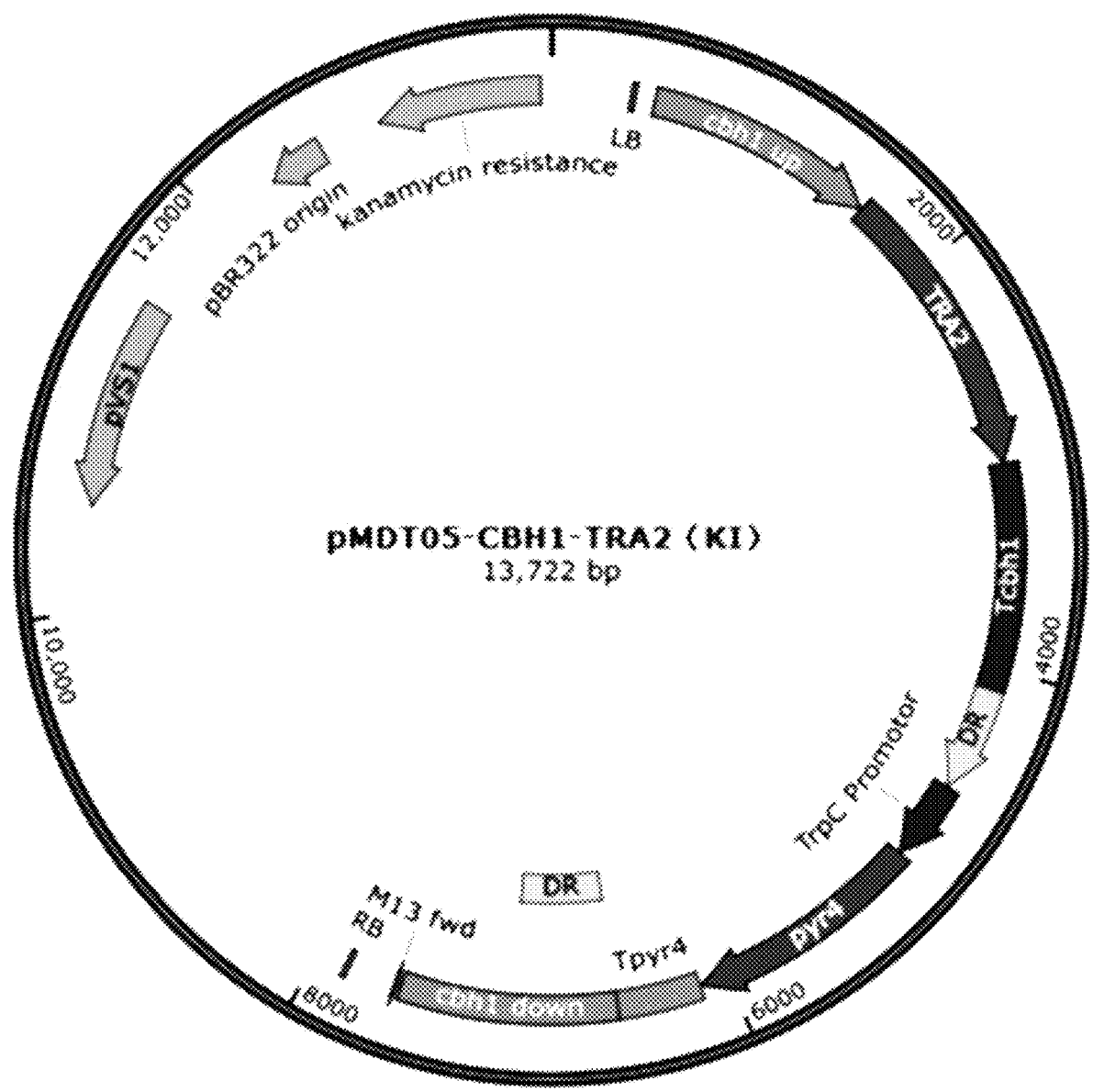
FIG. 8 shows a schematic drawing of the plasmid pMDT05-CBHI-TRA2 (KI).

All the PCR products above were recovered using an OMEGA gel extraction kit. The recovered fragments were mixed in equal molar ratio as templates, and an approximately 7 kb fusion fragment was amplified by SOE-PCR with primers CBH1-F1 and CBHI-R4 as forward and reverse primers. The linearized pMDT-05 was amplified using primers pMDT-SpeI-R and pMDT-XbaI-F, and then digested with DpnI for 3 hours. The two fragments were recovered using an OMEGA gel extraction kit and ligated together using a ClonExpress II one-step cloning kit, and then transformed into *E. coli* TOP10 competent cells. The recombinant plasmid that verified by sequencing was named as pMDT05-CBHI-TRA2 (KI) (FIG. 8). The primer sequences are shown in Table 6.

6. Construction of CBH2 Site-Specific Integration Expression Vector pMDT05-CBH2-TRA2 (KI)

A Search program was performed to obtain the locus sequence information of CBH2 (Cel6A) gene in the database of *Trichoderma reesei* genome.

A 1087 bp fragment used as 5' flanking homologous region was amplified from *Trichoderma reesei* genomic DNA using primers CBH2-F1 and EcoRI-CBH2-UR. The pyr4 expression cassette was amplified from plasmid pMDT05-mus53KO using primers EcoRI-CBH2-TrpC-F and CBH2-D-TU-R. An 1187 bp fragment used as 3' flanking homologous region was amplified from *Trichoderma reesei* genomic DNA using primers Tpyr4-CBH2-D-F and CBH2-R3.

All the PCR products above were recovered using an OMEGA gel extraction kit. The recovered fragments were mixed in equal molar ratio as templates, and an approximately 4.2 kb fusion fragment was amplified by SOE-PCR with primers CBH2-F1 and CBH2-R3. The linearized pMDT-05 was amplified using primers pMDT-SpeI-R and pMDT-XbaI-F, and then digested with DpnI for 3 hours. The two fragments were recovered using an OMEGA gel extraction kit, and ligated together using a ClonExpress II one-step cloning kit, and then transformed into *E. coli* TOP10 competent cells. The recombinant plasmid that verified by sequencing was named as pMDT05-CBH2-pyr4.

An approximately 4.7 kb expression cassette Pcbh1-TRA2-Tcbh1 was amplified from plasmid pMGU-cbh1-TRA2 using primers E-CBH2-PCBH-F and CBH2-DR-R2. A 437 bp fragment used as repeat sequence was amplified from *Trichoderma reesei* genomic DNA using primers CBH-DR-F and E-CBH2-DR-R.

Figure 9:
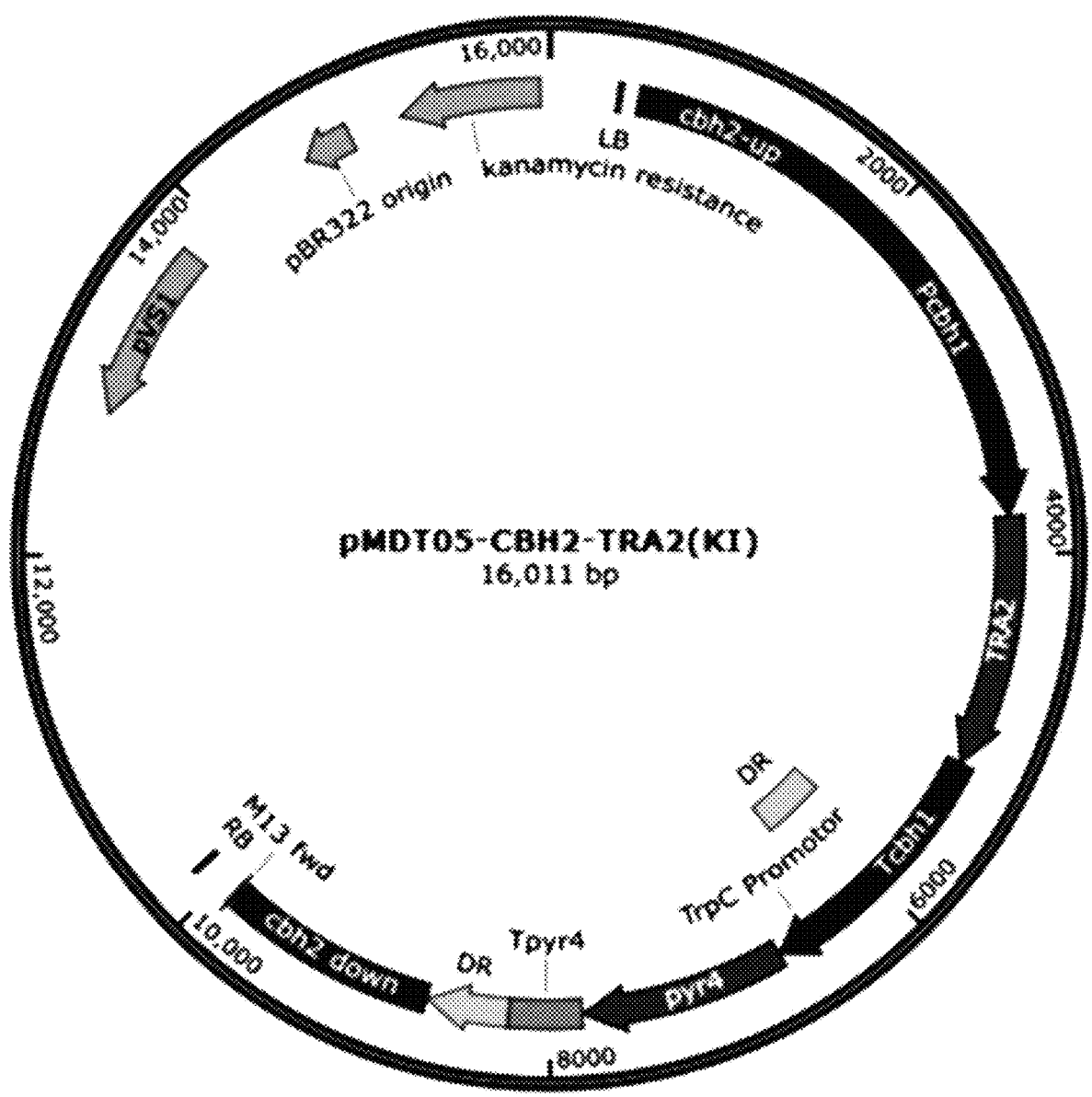
FIG. 9 shows a schematic drawing of the plasmid pMDT05-CBHII-TRA2 (KI).

The two fragments were recovered using an OMEGA gel extraction kit. The recovered fragments were mixed in equal molar ratio as templates, and an approximately 5.1 kb fusion fragment was amplified by SOE-PCR with primers E-CBH2-PCBH-F and E-CBH2-DR-R, and then recovered using an OMEGA gel extraction kit. The purified fusion fragment was cloned into EcoRI-digested pMDT05-CBH2-pyr4 using a ClonExpress II one-step cloning kit, and then transformed into *E. coli* TOP10 competent cells. The recombinant plasmid that verified by sequencing was named as pMDT05-CBH2-TRA2 (KI) (FIG. 9). The primer sequences are shown in Table 6.

7. Construction of EG1 Site-Specific Integration Expression Vectors pMDT05-EG1-TRA2 (KI)

A Search program was performed to obtain the locus sequence information of EG1 (Cel7B) gene in the database of *Trichoderma reesei* genome.

An 1149 bp fragment used as 5' flanking homologous region was amplified from *Trichoderma reesei* genomic DNA using primers WF-EG1-UF1 and P-EG1-R The pyr4 expression cassette was amplified from plasmid pMDT05-mus53KO using primers EG1-pyr4-F and CBH2-R6. A 501 bp fragment used as repeat sequence and a 1211 bp fragment used as 3' flanking homologous region were amplified from *Trichoderma reesei* genomic DNA using primer pairs CBH2-F5/EG1-TRA2-R and EG1-DW-F/EG1-DW-R, separately.

All the PCR products were recovered using an OMEGA gel extraction kit. The recovered fragments were mixed in equal molar ratio as templates, and an approximately 4.8 kb fusion fragment was amplified by SOE-PCR with primers WF-EG1-UF1 and EG1-DW-R. The linearized pMDT-05 was amplified using primers pMDT-SpeI-R and pMDT-XbaI-F, and then digested with DpnI for 3 hours. The two fragments were recovered using an OMEGA gel extraction kit and ligated together using a ClonExpress II one-step cloning kit, and then transformed into *E. coli* TOP10 competent cells. The recombinant plasmid that verified by sequencing was named as pMDT05-EG1-pyr4.

Figure 10:
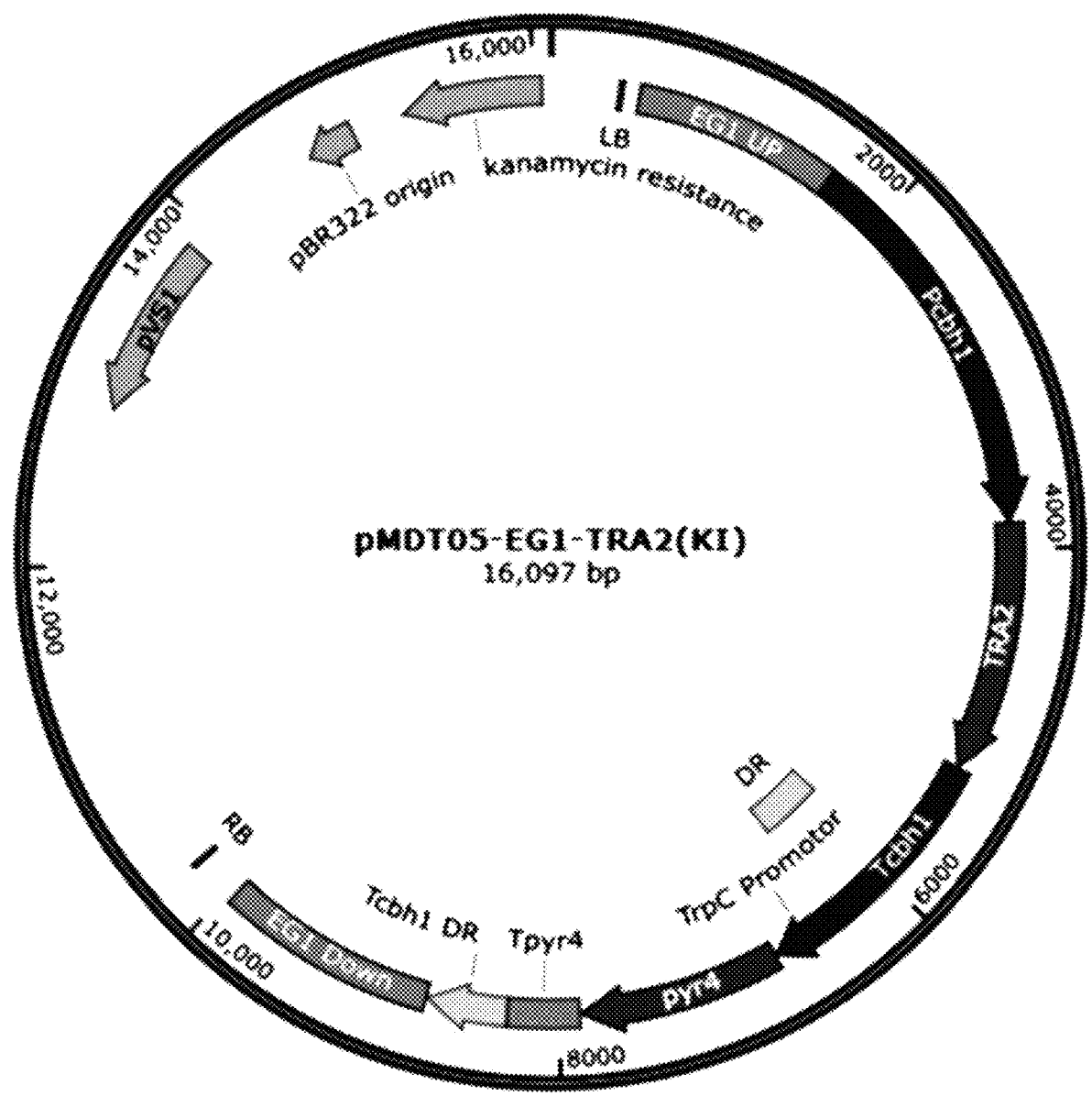
FIG. 10 shows a schematic drawing of the plasmid pMDT05-EG1-TRA2 (KI).

An approximately 4.7 kb expression cassette Pcbh1-TRA2-Tcbh1 was amplified from plasmid pMGU-cbh1-TRA2 using primers EG1-TRA2-F and CBH2-R22. The linearized pMDT05-EG-pyr4 was amplified using primers CBH2-F66 and P-EG1-R, and then digested with DpnI for 3 hours. The two fragments were recovered using an OMEGA gel extraction kit and ligated together using a ClonExpress II one-step cloning kit, and then transformed into *E. coli* TOP10 competent cells. The recombinant plasmid that verified by sequencing was named as pMDT05-EG1-TRA2 (KI) (FIG. 10). The primer sequences are shown in Table 6.

8. Construction of EG2 Site-Specific Integration Expression Vectors pMDT05-EG2-TRA2 (KI)

A Search program was performed to obtain the locus sequence information of EG2 (Cel5B) gene in the database of *Trichoderma reesei* genome.

An 1100 bp fragment used as 5' flanking homologous region was amplified from *Trichoderma reesei* genomic DNA using primers WF-EG2-UF1 and P-EG2-R. The pyr4 expression cassette was amplified from plasmid pMDT05-mus53KO using primers EG2-pyr4-F and CBH2-R6. A 501 bp fragment used as repeat sequence and a 1098 bp fragment used as 3' flanking homologous region were amplified from *Trichoderma reesei* genomic DNA using primer pairs CBH2-F5/EG2-TRA2-R and EG2-DW-F/EG2-DW-R, separately.

All the PCR products were recovered using an OMEGA gel extraction kit. The recovered fragments were mixed in equal molar ratio as templates, and an approximately 4.6 kb fusion fragment was amplified by SOE-PCR with primers WF-EG2-UF1 and EG2-DW-R The linearized pMDT-05 was amplified using primers pMDT-SpeI-R and pMDT-XbaI-F, and then digested with DpnI for 3 hours. The two fragments were recovered using an OMEGA gel extraction kit and ligated together using a ConExpress II Hone-step cloning kit, and then transformed into *E. coli* TOP10 competent cells. The recombinant plasmid that verified by sequencing was named as pMDT05-EG2-pyr4.

Figure 11:
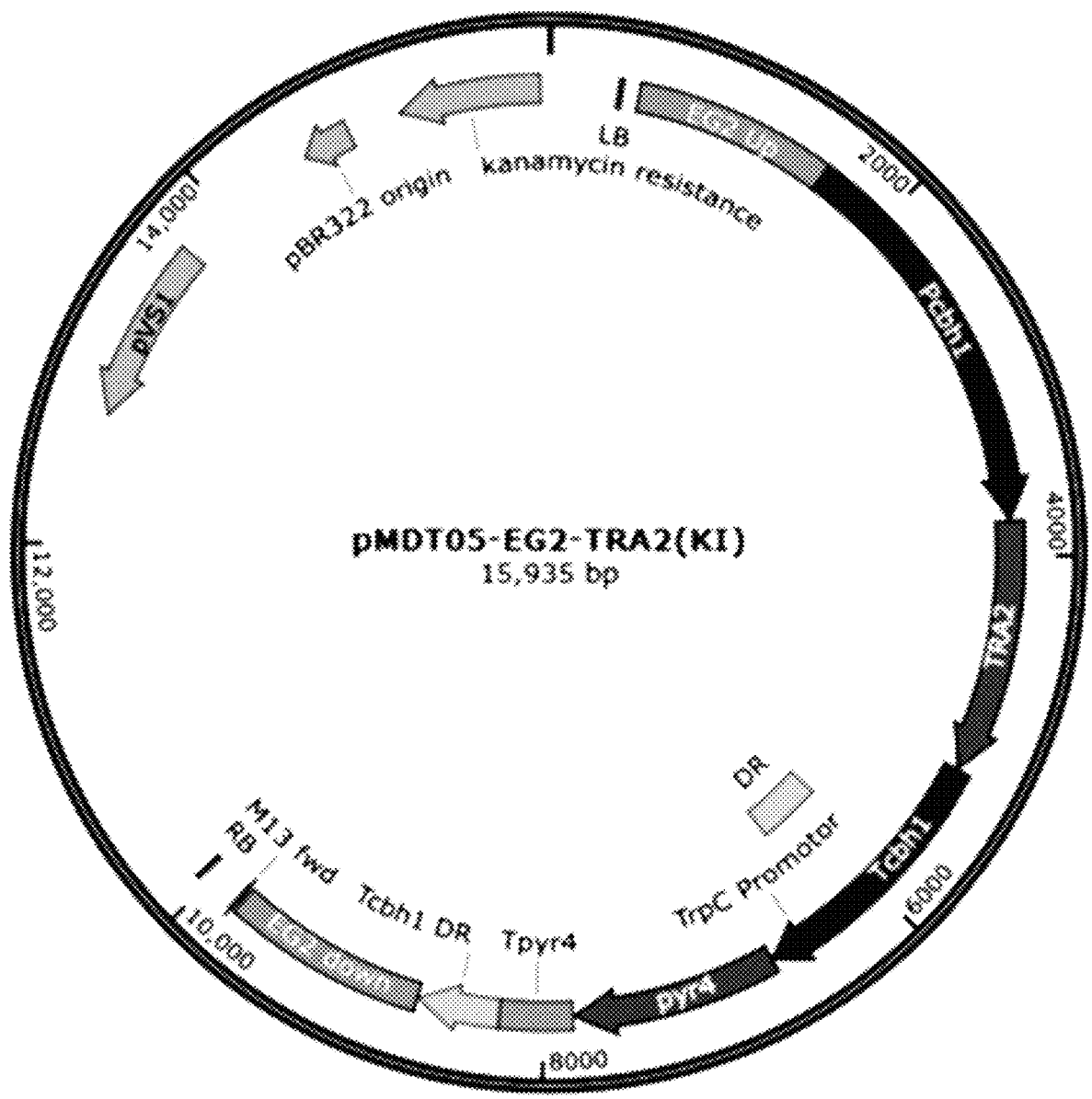
FIG. 11 shows a schematic drawing of the plasmid pMDT05-EGII-TRA2 (KI).

An approximately 4.7 kb expression cassette Pcbh1-TRA2-Tcbh1 was amplified from plasmid pMGU-cbh1-TRA2 using primers EG1-TRA2-F and CBH2-R22. The linearized pMDT5-EG2-pyr4 was amplified using primers CBH2-F66 and P-EG2-R, and then digested with DpnI for 3 hours. The two fragments were recovered using an OMEGA gel extraction kit and ligated together using a ConExpress H one-step cloning kit, and then transformed into *E. coli* TOP10 competent cells. The recombinant plasmid that verified by sequencing was named as pMDT05-EG2-TRA2 (KI) (FIG. 11). The primer sequences are shown in Table 6.

TABLE 6

Sequence of the Primers used in site-specific integration vectors

| Primers | Primer sequences (5'-3') |
|---|---|
| CBH1-F1 | SEQ ID NO: 90 |
| CBH1-R1 | SEQ ID NO: 91 |
| CBH1-F2 | SEQ ID NO: 92 |
| CBH1-R2 | SEQ ID NO: 93 |
| CBH1-F3 | SEQ ID NO: 94 |
| CBH1-R3 | SEQ ID NO: 95 |

TABLE 6-continued

Sequence of the Primers used in site-specific integration vectors

| Primers | Primer sequences (5'-3') |
|---|---|
| CBH1-F4 | SEQ ID NO: 96 |
| CBH1-R4 | SEQ ID NO: 97 |
| pMDT-SpeI-R | SEQ ID NO: 98 |
| pMDT-XbaI-F | SEQ ID NO: 99 |
| CBH2-F1 | SEQ ID NO: 100 |
| EcoRI-CBH2-UR | SEQ ID NO: 101 |
| EcoRI-CBH2-TrpC-F | SEQ ID NO: 102 |
| CBH2-D-TU-R | SEQ ID NO: 103 |
| Tpyr4-CBH2-D-F | SEQ ID NO: 104 |
| CBH2-R3 | SEQ ID NO: 105 |
| E-CBH2-PCBH-F | SEQ ID NO: 106 |
| CBH2-DR-R2 | SEQ ID NO: 107 |
| CBH-DR-F | SEQ ID NO: 108 |
| E-CBH2-DR-R | SEQ ID NO: 109 |
| WF-EG1-UF1 | SEQ ID NO: 110 |
| P-EG1-R | SEQ ID NO: 111 |
| EG1-pyr4-F | SEQ ID NO: 112 |
| CBH2-R6 | SEQ ID NO: 113 |
| CBH2-F5 | SEQ ID NO: 114 |
| EG1-TRA2-R | SEQ ID NO: 115 |
| EG1-DW-F | SEQ ID NO: 116 |
| EG1-DW-R | SEQ ID NO: 117 |
| EG1-TRA2-F | SEQ ID NO: 118 |
| CBH2-R22 | SEQ ID NO: 119 |
| CBH2-F66 | SEQ ID NO: 120 |
| P-EG1-R | SEQ ID NO: 121 |
| WF-EG2-UF1 | SEQ ID NO: 122 |
| P-EG2-R | SEQ ID NO: 123 |
| EG2-pyr4-F | SEQ ID NO: 124 |
| CBH2-R6 | SEQ ID NO: 113 |
| CBH2-F5 | SEQ ID NO: 114 |
| EG2-TRA2-R | SEQ ID NO: 125 |
| EG2-DW-F | SEQ ID NO: 126 |
| EG2-DW-R | SEQ ID NO: 127 |
| EG2-TRA2-F | SEQ ID NO: 128 |
| CBH2-R22 | SEQ ID NO: 119 |
| CBH2-F66 | SEQ ID NO: 120 |
| P-EG2-R | SEQ ID NO: 123 |

Example 13 Construction of Four Copies Site-Specific Integration Expression Strain Four major cellulases CBH1, CBH2, EG1 and EG2 account for more than 75% of the total extracellular proteins under the induction condition. Not only target gene TRA2, but also cellulase genes were induced to express under the same inducible promoter Pcbh1. This way, there will be more cellulase components in the supernatant of fermentation broth as hybrid proteins, which will not only be to a disadvantage for the downstream processes, but also consume some raw materials to synthesize these cellulases. In the present embodiment, the target gene expression cassette was separately integrated into the CBH1, CBH2, EG1 and EG2 loci of stain Rut-C30 (pyr4⁻, mus53⁻).

5. Construction of a Recombinant Strain by Site-Specific Integration at CBH1 Locus The CBH1 site-specific integration vector pMDT05-CBHI-TRA2 (KI) was transformed into strain Rut-C30 (pyr4⁻, mus53⁻) by *Agrobacterium*-mediated transformation described in Example 4. Thirty-six transformants were picked and transferred to MM solid plates with 300 μg/mL cefotaxime and cultured at 28° C. for 3 days. Twenty of them which grown normally were transferred to PDA plates, and cultured at 28° C. for 7 days.

All the twenty transformants were screened by PCR using primer pairs NdeI-Pcbh1-F2/TRA2-CX-R1 and pyr4-LB-R/CBH-down-R to confirm the homologous recombination occurred at CBH1 locus through the 5' and 3' flanking homologous regions and screened by PCR using primers RB-YZ-F and RB-YZ-R (see table 5) to confirm whether there was random integration outside the CBH1 locus. In the present embodiment, for each transformants, a small amount of mycelium was picked out from the PDA plate cultured for 3 days and heated at 98° C. for 10 minutes in 20 µl of sterile water. The supernatants were centrifuged and used as templates. An approximately 2.7 kb fragment and an approximately 1.3 kb fragment could be amplified using primer pairs NdeI-Pcbh1-F2/TRA2-CX-R1 and pyr4-LB-R/CBH-down-R if the homologous recombination occurred at correct regions, while a 425 bp fragment could not be amplified using primer RB-YZ-F and RB-YZ-R, indicating that no random integration occurred. In this embodiment, fourteen positive transformants were obtained. One of the positive transformants was selected to excise the pyr4 gene expression cassette according to the method described in Example 11. The excision was verified by PCR using primers HC2-JD-F2 and CBH1-JD-R2. A 698 bp fragment could be amplified from the one with excision of pyr4 gene expression cassette. The positive strain was named as LYH-D1 (pyr4⁻, mus53⁻). The primer sequences are shown in Table 7.

6. Construction of a Recombinant Strain by Site-Specific Integration at CBH2 Locus The CBH2 site-specific integration vector pMDT05-CBH2-TRA2 (KI) was transformed into LYH-D1 (pyr4⁻, mus53⁻) according to the method and steps of CBH1 site-specific integration described above. A recombinant strain LYH-D2 (pyr4⁻, mus53⁻) containing two copies of the target gene expression cassette was obtained.

In the present embodiment, all transformants were screened by PCR using primer pairs CBH2-F/Pcbh1-CX and pyr4-LB-R/CBH2-R to confirm the homologous recombination occurred at CBH2 locus through the 5' and 3' flanking homologous regions and screened by PCR using primers RB-YZ-F and RB-YZ-R (see table 5) to confirm whether there was random integration outside the CBH2 locus. Primers Tcbh1-CX-F and CBH2-R2 were used to verify the excision of the pyr4 gene expression cassette. The primer sequences are shown in Table 7.

7. Construction of a Recombinant Strain by Site-Specific Integration at EG1 Locus The EG1 site-specific integration vector pMDT05-EG1-TRA2 (KI) was transformed into LYH-D2 (pyr4⁻, mus53⁻) according to the method and steps of CBH1 site-specific integration described above. A recombinant strain LYH-D3 (pyr4⁻, mus53⁻) containing three copies of target gene expression cassette was obtained.

In the present embodiment, all transformants were screened by PCR using primer pairs EG1-UF1/Pcbh1-CX and pyr4-LB-R/EG1-R to confirm the homologous recombination occurred at EG1 locus through the 5' and 3' flanking homologous regions and screened by PCR using primers RB-YZ-F and RB-YZ-R (see table 5) to confirm whether there was random integration outside the CBH2 locus. Primers Tcbh1-CX-F and EG1-DR1 were used to verify the excision of the pyr4 gene expression cassette. The primer sequences are shown in Table 7.

8. Construction of a Recombinant Strain by Site-Specific Integration at EG2 Locus The EG2 site-specific integration vector pMDT05-EG2-TRA2 (KI) was transformed into LYH-D3 (pyr4⁻, mus53⁻) according to the method and steps of CBH1 site-specific integration described above. A recombinant strain LYH-D4 (pyr4⁻, mus53⁻) containing three copies of target gene expression cassette was obtained.

In the present embodiment, all transformants were screened by PCR using primer pairs EG2-UF1/Pcbh1-CX and pyr4-LB-R/EG22-R to confirm the homologous recombination occurred at EG1 locus through the 5' and 3' flanking homologous regions and screened by PCR using primers RB-YZ-F and RB-YZ-R (see table 5) to confirm whether there was random integration outside the CBH2 locus. Primers Tcbh1-CX-F and EG2-DR1 were used to verify the excision of the pyr4 gene expression cassette. The primer sequences are shown in Table 7.

TABLE 7

Sequence of the Primers used in site-specific integration and verification

| Primers | Primer sequences (5'-3') |
|---|---|
| NdeI-Pcbh1-F2 | SEQ ID NO: 129 |
| TRA2-CX-R1 | SEQ ID NO: 130 |
| pyr4-LB-R | SEQ ID NO: 131 |
| CBH-down-R | SEQ ID NO: 132 |
| HC2-JD-F2 | SEQ ID NO: 133 |
| CBH1-JD-R2 | SEQ ID NO: 134 |
| CBH2-F | SEQ ID NO: 135 |
| CBH2-R | SEQ ID NO: 136 |
| CBH2-R2 | SEQ ID NO: 137 |
| EG1-UF1 | SEQ ID NO: 138 |
| EG1-R | SEQ ID NO: 139 |
| EG1-DR1 | SEQ ID NO: 140 |
| EG2-UF1 | SEQ ID NO: 141 |
| EG2-R | SEQ ID NO: 142 |
| EG2-DR1 | SEQ ID NO: 143 |

Example 14: Construction of *Trichoderma reesei* Mus53 Gene Repair Vector pMDT05-mus53 (KI)

A 2209 bp fragment containing 5' flanking homologous region and repeat sequence was amplified from *Trichoderma reesei* genomic DNA using primers mus53-up-F and mus53-up-R. The pyr4 gene expression cassette was amplified from plasmid pMDT05-mus53KO using primers mus53-pyr4-F and mus53-pyr4-R The two PCR products were recovered using an OMEGA gel extraction kit. The recovered fragments were mixed in equal molar ratio as templates, and an approximately 4.0 kb fusion fragment was amplified by SOE-PCR with primers mus53-up-F and mus53-pyr4-R The linearized pMDT-05 was amplified using primers pMDT-SpeI-R and pMDT-XbaI-F, and then digested with DpnI for 3 hours. The fusion fragment and digested pMDT-05 were recovered using an OMEGA gel extraction kit and ligated together using a ClonExpress H one-step cloning kit, and then transformed into *E. coli* TOP10 competent cells. The recombinant plasmid that verified by sequencing was named aspMDT05-mus53-pyr4.

Figure 12:
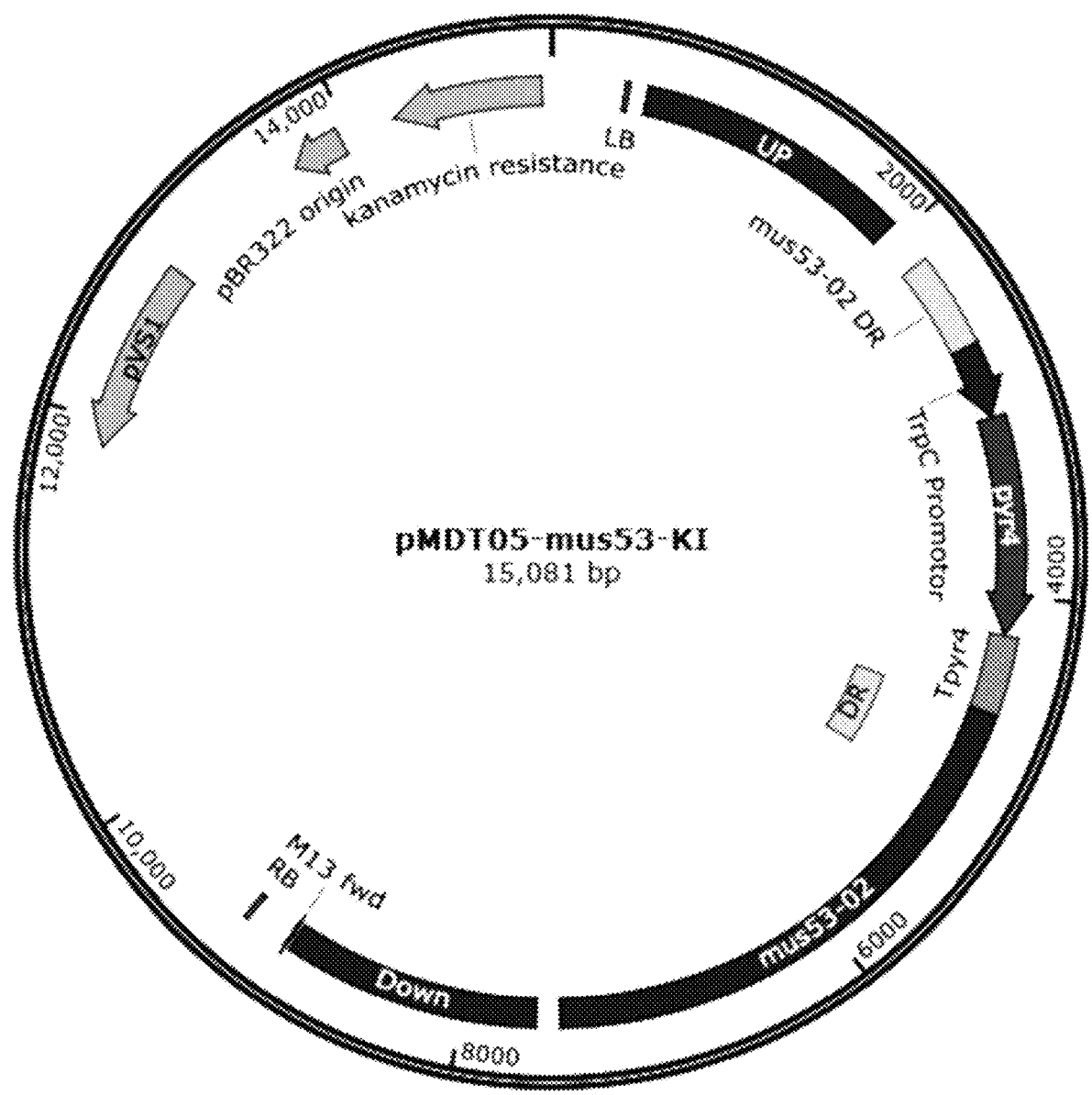
FIG. 12 shows a schematic drawing of the plasmid pMDT05-mus53 (KI).
Figure 13:
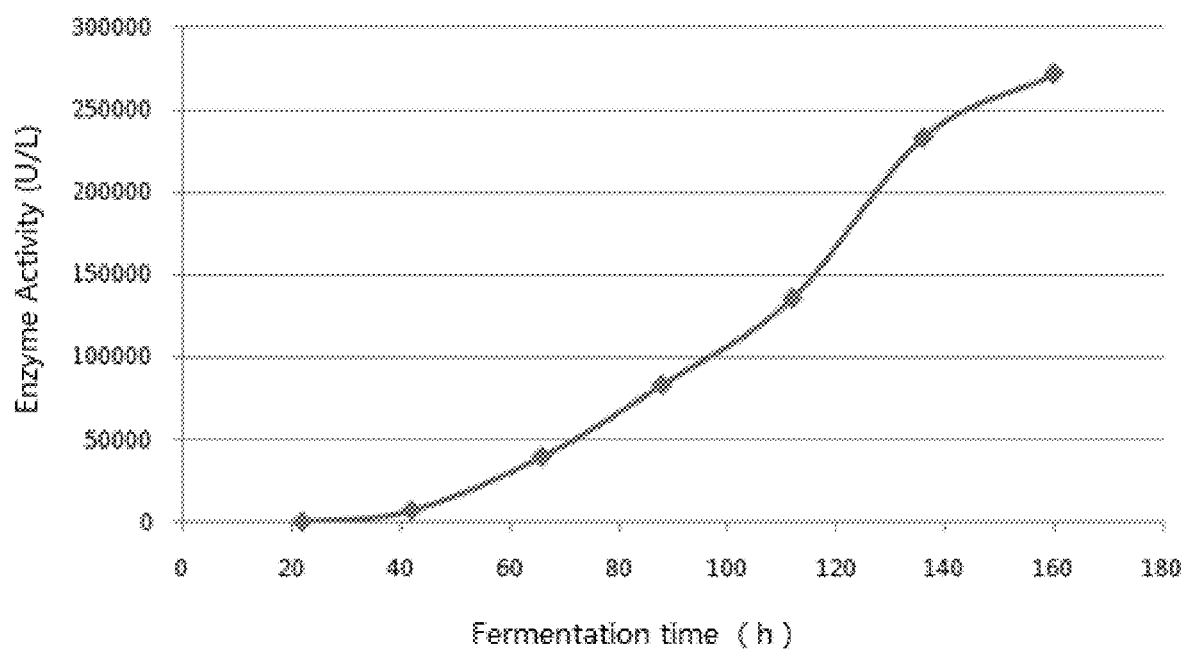
FIG. 13 shows the activity change of OxDC secreted by *Trichoderma reesei* stain LYH-D4 in 7 L fed-batch fermentation.

A 4343 bp fragment containing 3' flanking homologous region and mus53 gene repair region was amplified from *Trichoderma reesei* genomic DNA using primers mus53-down-F and mus53-down-R The plasmid pMDT05-mus53-pyr4 was digested with EcoRI for 3 hours. The PCR products and EcoRI-digested pMDT05-mus53-pyr4 were recovered using an OMEGA gel extraction kit and ligated together using a ClonExpress II one-step cloning kit, and then transformed into *E. coli* TOP10 competent cells. The recombinant plasmid that verified by sequencing was named as pMDT05-mus53 (KI) (FIG. 12).

Example 15: Repair of Mus53 and Pyr4 Genes in LYH-D4 (Pyr4⁻, Mus53⁻)

The mus53 gene was repaired in *Trichoderma reesei* LYH-D4 (pyr4⁻, mus53⁻). The mus53 gene repair vector pMDT05-mus53 (KI) was transformed into strain LYH-D4 (pyr4⁻, mus53⁻) by *Agrobacterium*-mediated transformation described in Example 4. Twenty-seven transformants were picked and transferred to MM solid plates containing 300 μg/mL cefotaxime and cultured at 28° C. for 3 days. Fifteen of them grown normally were transferred to PDA plates and cultured at 28° C. for 7 days until the spores matured.

The fifteen transformants were screened by PCR using primer pairs MUS-F/TrpC-CX-F and MUS-YZ-F2/MUS-R to confirm the homologous integration occurred at mus53 locus through the 5' flanking homologous and 3' homologous regions and screened by PCR using primers RB-YZ-F and RB-YZ-R to confirm whether there was random integration outside the mus53 locus. One of the positive transformants was selected to excise the pyr4 gene expression cassette according to the method described in Example 11. The excision was verified by PCR using primers mus3-YZ-F and MUS-YZ-R2. The positive strain with mus53 gene repaired was named as LYH-D4 (pyr4⁻). The primers used for verification seen below.

```
Primer MUS-YZ-F2 (SEQ ID NO: 144):
5'-GTGCTGGGAGACGATGTGATG-3'

Primer mus3-YZ-F (SEQ ID NO: 145):
5'-CAGCAGCGACGCGATTCCTTC-3'

Primer MUS-YZ-R2 (SEQ ID NO: 146):
5'-CTGCTTCAGAATGATGCGGATG-3'
```

After mus53 gene repaired, the pyr4 gene repair vector pMDT05-pyr4 KI was used to repair the pyr4 gene of strain LYH-D4 (pyr4⁻). The final positive strain was named as LYH-D4.

Example 16: Fermentation Optimization of Strain LYH-D4 in Shaking Flask

Because the four major cellulase genes of *Trichoderma reesei* strain LYH-D4 were knocked out, microcrystalline cellulose could not be used as inducer and carbon source, so the fermentation medium optimized for random integration strains in Example 6 was not suitable for strain LYH-D4.

The present embodiment optimized the medium components through a series of single-factor experiments of medium composition and response surface curve experiments to improve the fermentation activity of strain LYH-D4 per unit volume, and the optimized results showed that that the OxDC activity in supernatant of fermentation broth was about 6800 IU/L with unoptimized fermentation medium (composition: lactose 30 g/L, corn steep powder 12 g/L, $(NH_4)_2SO_4$ 0.5 g/L, $MgSO_4 \cdot 7H_2O$ 1.56 g/L, $CaCl_2$ 0.5 g/L, $KH_2PO_4$ 6 g/L, wheat bran powder 2 g/L, Mandelstrace element (1000×) 1 ml/L, $MnCl_2$ 5 mM, pH 4.0). The activity of OxDC in supernatant could reach 26500 IU/L after 168 hours of fermentation in shake flask. The optimal medium composition was: glucose 3-6 g/L, lactose 30-40 g/L, corn steep powder 7-10 g/L, $(NH_4)_2SO_4$ 0.5-1 g/L, $MgSO_4 \cdot 7H_2O$ 1.56 g/L, $CaCl_2$ 0.5 g/IL, $KH_2PO_4$ 2-4 g/L, wheat bran powder 10-20 g/L, Mandels trace element (1000×) 1 ml/L, $MnCl_2$ 0.5-5 mM, pH 3.0-4.5.

Example 17: Fermentation of Strain LYH-D4 Infermenter

3. Preparation of Seed

The hyphae of stain LYH-D4 were inoculated in several PDA solid plates, cultured at 28° C. for 7 days until the spores matured. The spore suspension was prepared by washing the spores with sterile water, and then the spore concentration was adjusted to $1 \times 10^8$/ml. The spore suspension was inoculated at 1% (v/v) into 500 ml MM liquid medium, and incubated at 28° C., 170 rpm in dark for 24-36 hours. It was used as seed culture for fermentation in 7 L fermentor.

4. Fermentation of *Trichoderma reesei* Strain LYH-D4 in 7 L Fermentor

Figure 14:
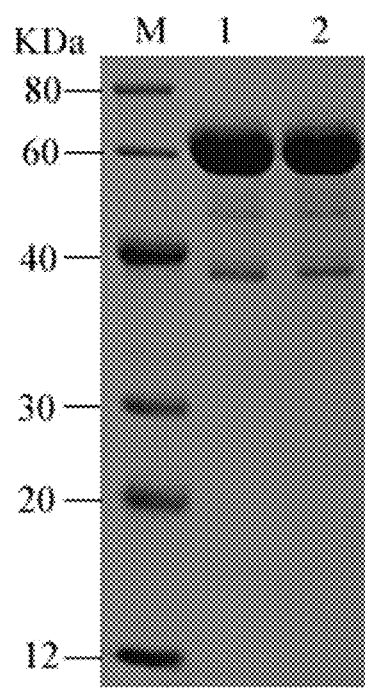
FIG. 14 shows a picture of SDS-PAGE analysis of culture supernatants in 7 L fed-batch fermentation; Lane1: culture supernatant after cultivation for 136 h; Lane2: culture supernatant after cultivation for 160 h. Both culture supernatants were diluted tenfold.
Figure 15:
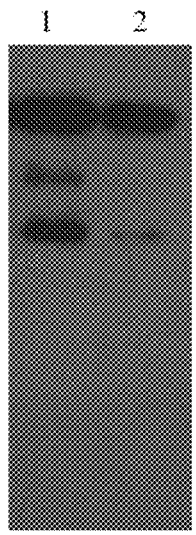
FIG. 15 shows a picture of Western blot analysis of the fermentation supernatants after cultivation for 160 h; Lane1: culture supernatant was diluted 200 times; Lane2: culture supernatant was diluted 500 times.

The whole fermentation process of *Trichoderma reesei* was divided into the following two phases: the first phase was the mycelium growth phase (0-72 hours): 4.5 L basic fermentation medium (glucose 20 g/L, corn steep powder 7 g/L, $KH_2PO_4$ 4 g/L, urea 1 g/L, $(NH_4)_2SO_4$ 2 g/L, $MgSO_4 \cdot 7H_2O$ 0.5 g/L, $CaCl_2$ 1 g/L, $MnCl_2$ 1 mM, Mandels trace element (1000×) 1 m/L, pH 4.0) was added to the 7 L fermenter (Shanghai Baoxing Biological equipment Engineering Co., Ltd.). The fermenter was seeded to 10% (v/v) with seed culture above and cultured at 28° C. with agitation for 72 hours. Dissolved oxygen level was kept above 30% with agitation at 250-500 rpm, and the agitation speed was adjusted according to the dissolved oxygen level. The culture pH was maintained at 3.5-4.0. In the mycelial growth phase, the initial glucose was close to depletion in 24-28 hours, and then 250 g/L lactose solution was injected at a rate of 12 m/h. The dry weight of the mycelium reached 15-18 g/L after 72 hours cultivation. The second phase was enzyme production phase (72-168 hours): after 72 hours, the 250 g/L lactose solution was continuously injected by peristaltic pump. The lactose concentration was not more than 2 g/L, and the dissolved oxygen level was always kept above 20%. The cultivation temperature was 28° C., and culture pH was maintained at 4.0 during the whole cultivation period. The activity of OxDC in supernatant of fermentation broth was determined every 24 hours. The activity of supernatant of fermentation broth could reach 271756 IU/L after 160 hours of fermentation. The supernatant of fermentation broth at the 136th and 160th hours was diluted 10 times and detected by SDS-PAGE. The results showed that the molecular weight of the target protein was about 60 kDa (FIG. 14). The fermentation broth samples were diluted 200 and 500 times for Western blot analysis (FIG. 15).

Example 18: Extraction and Recovery of Recombinant OxDC

The fermentation broth was centrifuged by 5000 rpm at room temperature for 15 minutes. The supernatant was filtered by inorganic ceramic membrane (Sanda membrane Environmental Technology Co., Ltd.) with pore size 100 nm, and the filtrate was collected, and mixed with 10% (w/v) aqueous solution of tannic acid to final concentration 1% with slow stirring, and allowed to stand for 1 hour at room temperature. The precipitated tannic acid-OxDC complex was separated by centrifugation with 8000 rpm at room temperature for 15 minutes, resuspended in ½ volume of sterile water, and centrifuged at 8000 rpm for 15 minutes. Collected the precipitate and repeated for one time. A 0.4 volume of 0.75-1.25% (w/v) polyethylene glycol solution was added with stirring to disperse the precipitate. OxDC would be redissolved from the tannin-protein complex by utilizing the stronger binding force between PEG and tannic acid. After stirring for 4 hours at room temperature, the resulting suspension was centrifuged to separate tannic acid-PEG complex at 8000 rpm for 15 minutes. The supernatant was retained. The supernatant was 2.5-fold concentrated enzyme solution. Finally, the light yellow OxDC solution was obtained by decolorizing with 2% activated carbon used for sugar production, and the recovery rate of OxDC was 90-95%. The decolorized OxDC solution was concentrated 10-30 times by ultrafiltration membrane with molecular weight of 10 kDa, and then spray dried to obtain OxDC powder.

Example 19: Properties and Comparative Analysis of Recombinant OxDC

Figure 16:
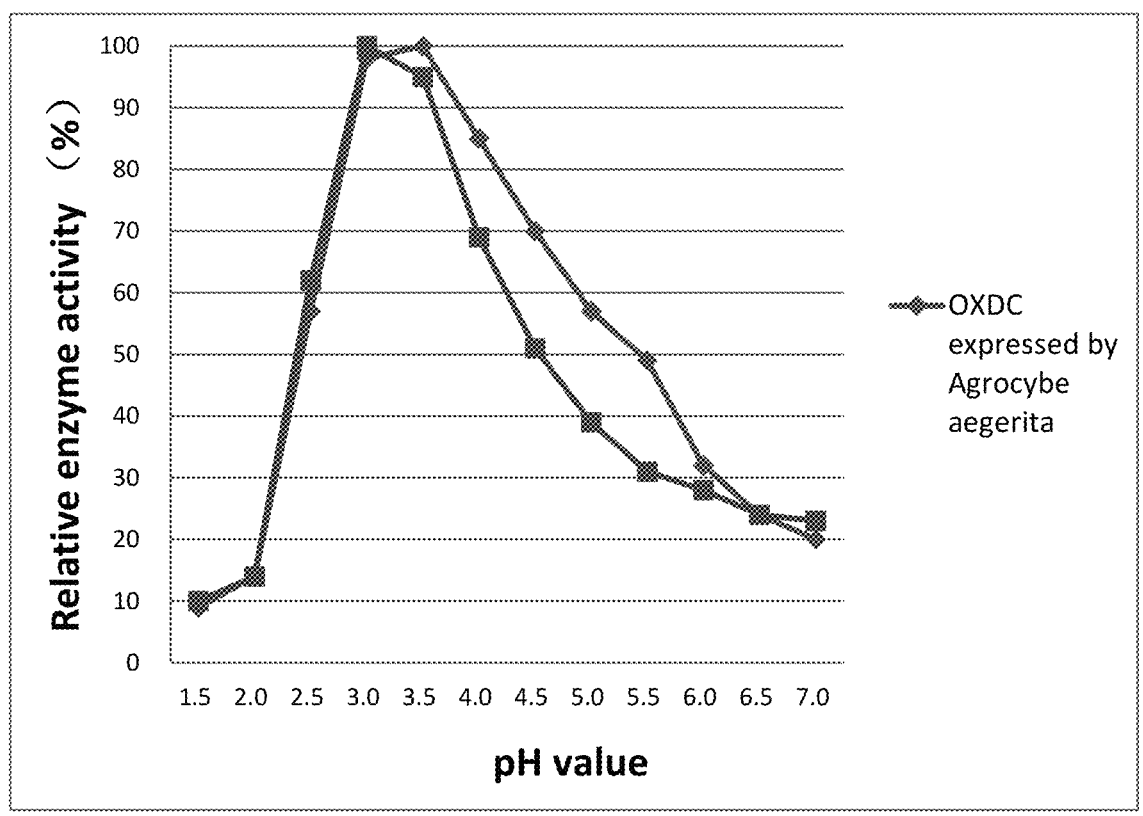
FIG. 16 shows relative activity of OxDC at pH 1.5-7.0.

The relative enzyme activities of recombinant OxDC expressed by *Trichoderma reesei* and the OxDC expressed by natural host *Agrocybe aegerita* were determined at pH 1.5-7.0. The results were as shown in FIG. 16. Under different pH conditions, the relative enzyme activity of recombinant OxDC was similar to that of natural OxDC expressed by *Agrocybe aegirit*. The recombinant OxDC maintained all or part of its activity at pH 1.5-7.0. At pH 1.5-2.5, the recombinant enzyme activity was not lower than 10% of that at the optimum pH, 50% at the pH 2.5-4.5, 25% at the pH 4.5-7.0. The optimum pH was 2.5-3.5.

Figure 17:
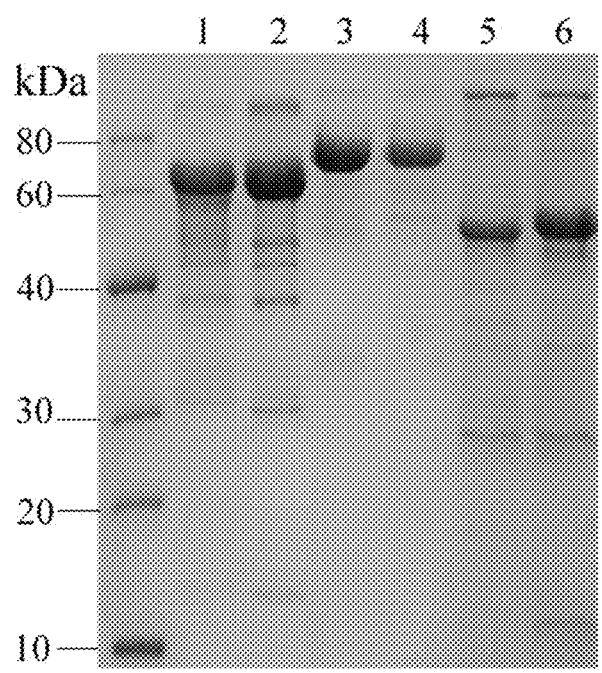
FIG. 17 shows a picture of SDS-PAGE analysis of recombinant OxDC expressed by three different expression systems: Lane 1 and 2: OxDC expressed by *Trichoderma reesei*; Lane 3 and 4: OxDC expressed by natural host, *Agrocybe aegirit*; Lane 5 and 6: OxDC expressed by *E. coli*.
Figure 18:
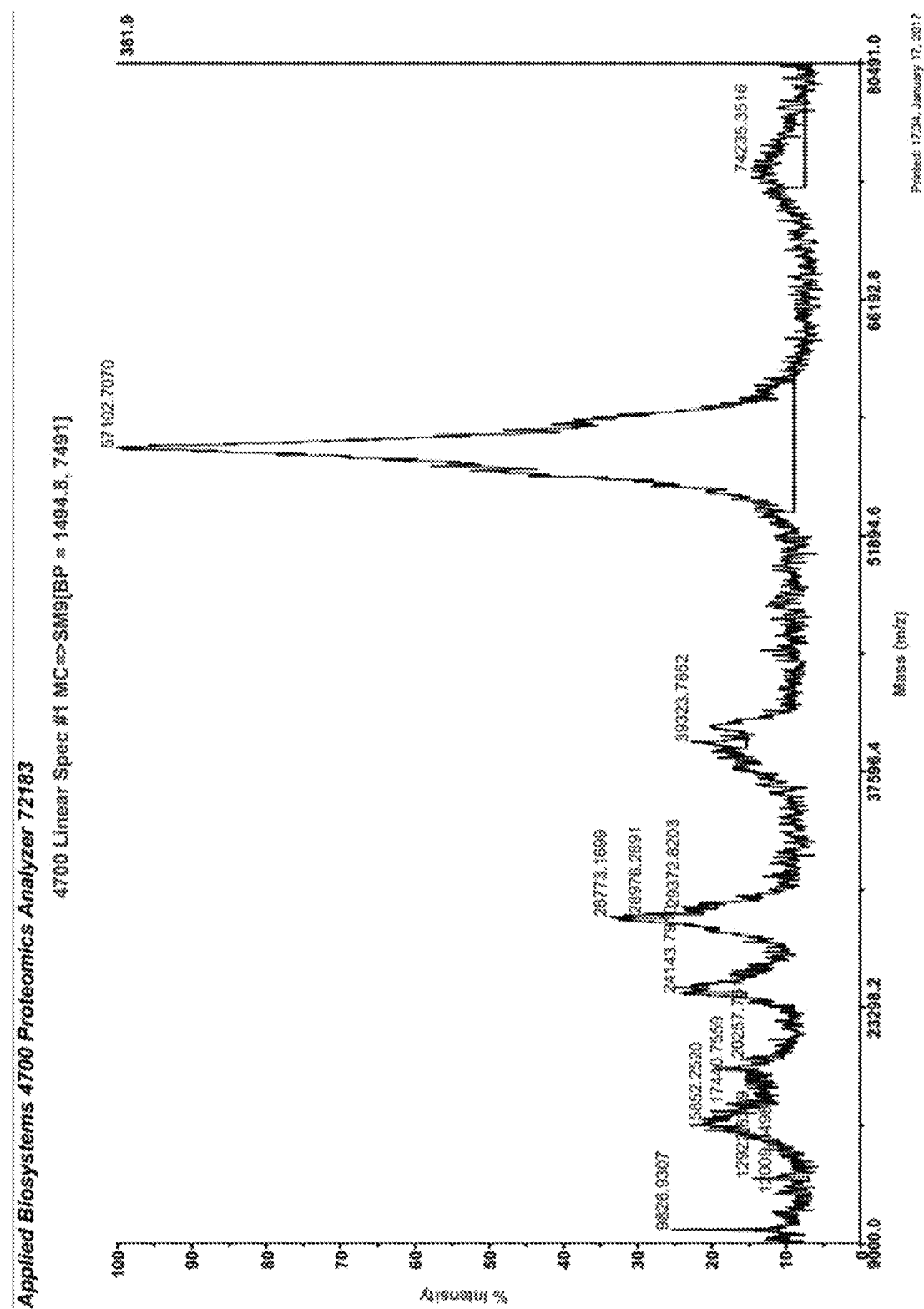
FIG. 18 shows a picture of MALDI-TOF mass spectrum of OxDC expressed by *Trichoderma reesei*.

The recombinant OxDC expressed by *Trichoderma reesei*, OxDC expressed by natural host *Agrocybe aegerita* and OxDC expressed by prokaryotic cells were analyzed by SDS-PAGE. The results are as shown in FIG. 17. Because of the different glycation modification forms and degrees, there are differences in the apparent molecular weight. The molecular weight of OxDC expressed in natural hosts was about 70 kDa, while that of recombinant OxDC expressed by *Trichoderma reesei* was about 60 kDa, but higher than that of OxDC expressed by prokaryotic cells without glycosylation modification. The molecular weight of glycosfree OxDC expressed in *E. coli* was about 50 kDa. The molecular weight of recombinant OxDC expressed by *Trichoderma reesei* was analyzed by MALDI-TOF-MS. The result showed that its real molecular weight was 57.1 kDa as shown in FIG. 18.

Figure 19:
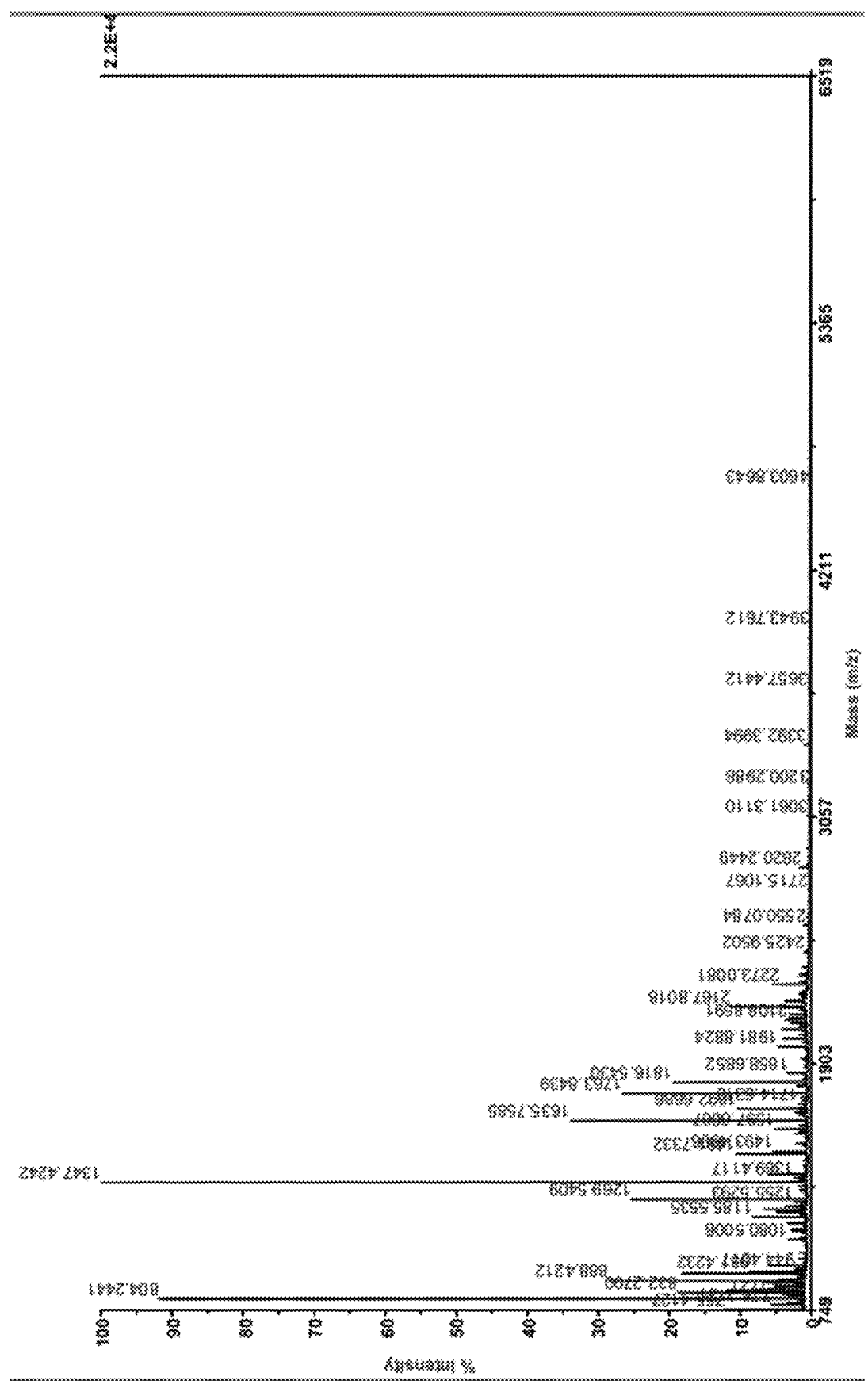
FIG. 19 shows a picture of MALDI-TOF mass spectrum of the peptides from trypsin hydrolysate of OxDC expressed by *Trichoderma reesei*.
Figure 20:
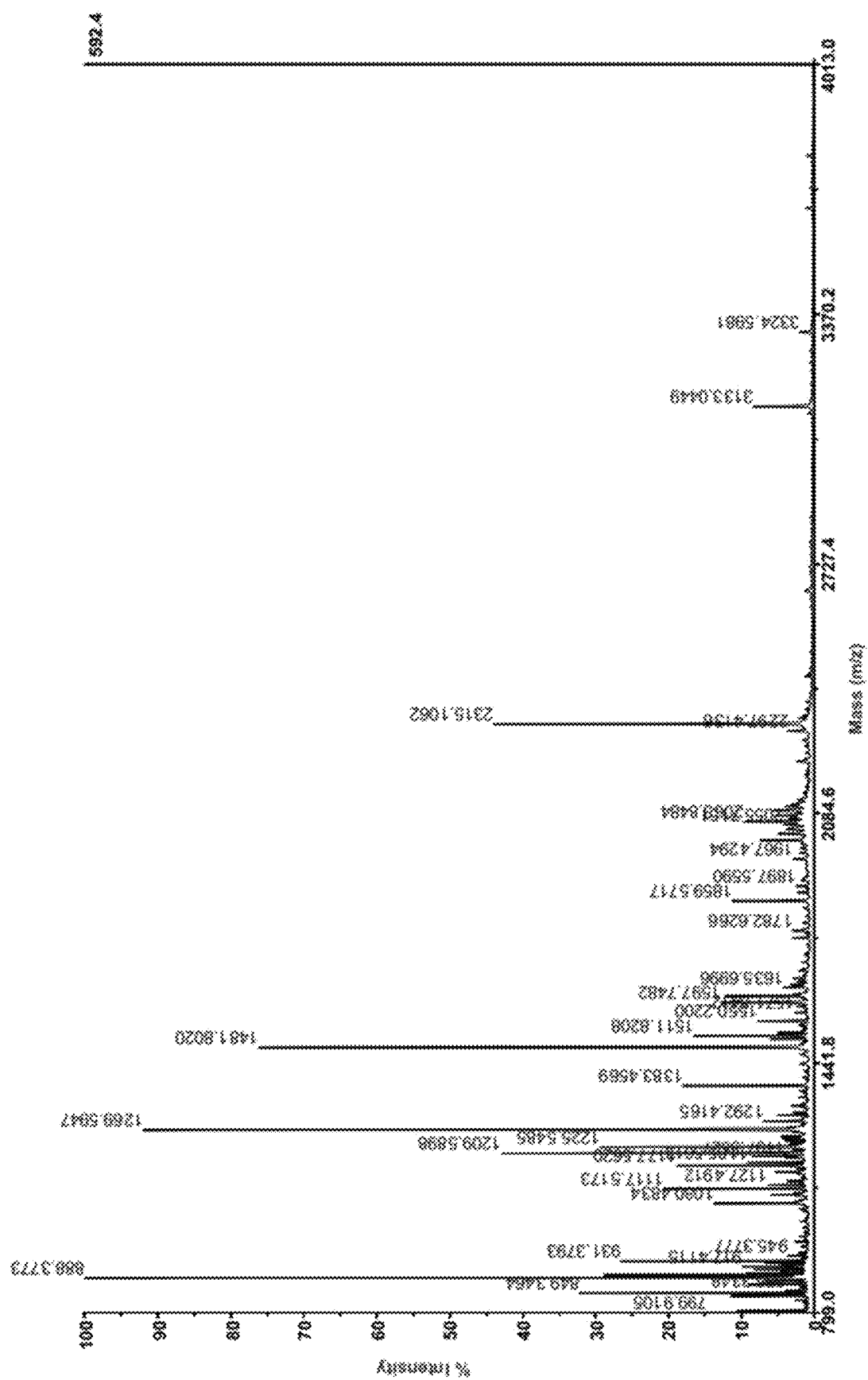
FIG. 20 shows a picture of MALDI-TOF mass spectrum of the peptides from trypsin hydrolysate of OxDC expressed by natural host, *Agrocybe aegerila*.
Figure 21:
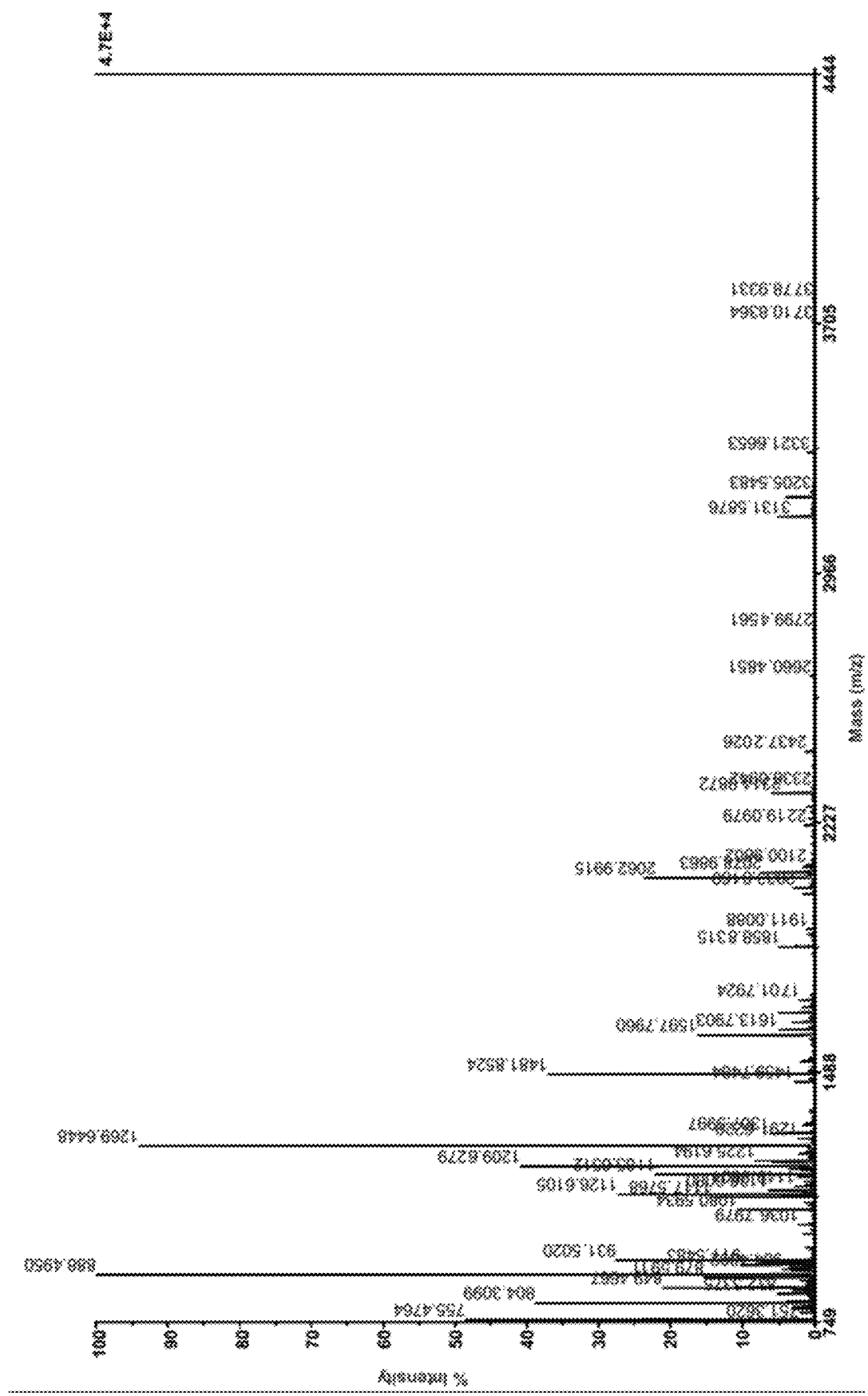
FIG. 21 shows a picture of MALDI-TOF mass spectrum of the peptides from trypsin hydrolysate of OxDC expressed by *E. coli*.

OxDCs expressed in the above three different expression systems were digested by trypsin treated with TPCK and analyzed by MALDI-TOF-MS, respectively (FIGS. 19, 20, 21). Due to the different forms and degrees of glycosylation, the mass spectra of the peptides from trypsin hydrolysate of OxDC were different, and the differences were specific to the host cells.

The other gene sequences (SEQ ID NOs: 10-16) of the present invention can also be recombinantly expressed in *Trichoderma reesei*, and the experimental results are similar to those of SEQ ID NO: 9.

The above embodiments are only better embodiments employed for fully illustrating the present invention and the scope of the invention is not limited thereto. Any equivalent changes and modifications made by skilled person in the art on the basis of the present invention are also within the scope as defined by the appended claims of the present invention.

What is claimed is:

1. A recombinant oxalate decarboxylase, wherein the recombinant oxalate decarboxylase is recombinantly expressed in a filamentous fungal host cell, resulting in a form and degree of glycosylation different from an original oxalate decarboxylase expressed in an original host cell, wherein the form and degree of glycosylation of the recombinant oxalate decarboxylase is specific to the filamentous fungal host cell, wherein the recombinant oxalate decarboxylase consists of the amino acids 20 to 470 of SEQ ID NO: 1, or the amino acids 25 to 472 of SEQ ID NO: 2, or the amino acids 20 to 455 of SEQ ID NO: 3, or the amino acids 21 to 447 of SEQ ID NO: 4, or the amino acids 20 to 470 of SEQ ID NO: 5, or the amino acids 21 to 455 of SEQ ID NO: 6, or the amino acids 25 to 440 of SEQ ID NO: 7, or the amino acids 24 to 472 of SEQ ID NO: 8, and the filamentous fungal host cell is *Trichoderma* host cell.

2. The recombinant oxalate decarboxylase according to claim 1, wherein the recombinant oxalate decarboxylase maintains all or part of an enzyme activity at pH 1.5-7.0, wherein at pH 1.5-2.5, the enzyme activity of the recombinant oxalate decarboxylase is not lower than 10% of the enzyme activity of the recombinant oxalate decarboxylase at an optimum pH, not lower than 50% of the enzyme activity of the recombinant oxalate decarboxylase at pH 2.5-4.5, and not lower than 25% of the enzyme activity of the recombinant OxD at the pH 4.5-7.0.

3. The recombinant oxalate decarboxylase according to claim 2, wherein the optimum pH of the recombinant oxalate decarboxylase is 2.5-3.5.

4. The recombinant oxalate decarboxylase according to claim 1, wherein a gene encoding the recombinant oxalate decarboxylase is derived from an eukaryote, wherein the eukaryote is selected from the group consisting of *Agrocybe aegerita, Agrocybe cylindracea, Flammulina velutipes, Coriolus versicolor, Postia placenta, Aspergillus luchuensis, Agaricus bisporus* and *Tricholoma lobayense Heim.*

5. A recombinant filamentous fungal host cell, wherein chromosome DNA of the recombinant filamentous fungal host cell contains a sequence of oxalate decarboxylase genes encoding the recombinant oxalate decarboxylase according to claim 1, and the filamentous fungal host cell is *Trichoderma* host cell.

6. The recombinant filamentous fungal host cell according to claim 5, wherein the recombinant filamentous fungal host cell is a *Trichoderma harzianum, Trichoderma koningii, Trichoderma reesei, Trichoderma longibrachiatum* or *Trichoderma viride* host cell of *Trichoderma* genus.

7. The recombinant filamentous fungal host cell according to claim 5, wherein the recombinant filamentous fungal host cell is a *Trichoderma reesei* host cell.

8. The recombinant filamentous fungal host cell according to claim 5, wherein at least 10% of the sequence encoding the recombinant oxalate decarboxylase is optimized according to a codon preference of flail the filamentous fungal host cell.

* * * * *

SEQUENCE LISTING

```
<160> NUMBER OF SEQ ID NOS: 146

<210> SEQ ID NO 1
<211> LENGTH: 470
<212> TYPE: PRT
<213> ORGANISM: Artificial Sequence
<220> FEATURE:
<223> OTHER INFORMATION: The sequence is synthetized.

<400> SEQUENCE: 1

Met Ile Ser Val Ala Ser Cys Thr Ile Ala Leu Leu Leu Ser Ser Val
1               5                   10                  15

Ala Phe Ala Ala Pro Ala Pro Ser Ser Ala Ala Ser Ser Ile Val Val
                20                  25                  30

Ser Ala Thr Ser Ser Ser Thr Val Ser Ser Ala Pro Val Ser Val Ser
            35                  40                  45

Ser Phe Leu Pro Thr Thr Ser Ile Ala Ala Ala Thr Pro Ser Ser Ile
        50                  55                  60

Ala Val Ala Leu Ser Ser Thr Ala Thr Val Pro Phe Ile Asp Leu Asn
65                  70                  75                  80

Pro Asn Gly Pro Leu Trp Asp Pro Ser Val Ser Gly Val Pro Gln Ala
                85                  90                  95

Glu Arg Gly Ser Leu Gly Ala Thr Ile Met Gly Pro Thr Asp Val Asp
                100                 105                 110

Thr Thr Lys Ala Asn Pro Asp Leu Leu Ala Pro Pro Thr Thr Asp His
            115                 120                 125

Gly Ser Val Asp Asn Ala Lys Trp Ala Phe Ser Leu Ser His Asn Arg
        130                 135                 140

Leu Gln Thr Gly Gly Trp Ala Arg Glu Gln Asn Ile Gly Ala Met Pro
145                 150                 155                 160

Ile Ala Thr Glu Met Ala Ser Val Asn Met Arg Leu Glu Pro Gly Ala
```

```
            165                 170                 175
Ile Arg Glu Leu His Trp His Lys Thr Ala Glu Trp Ala Tyr Val Leu
            180                 185                 190

Lys Gly Asn Thr Gln Val Thr Ala Val Asp Gln Asn Gly Lys Asn Phe
            195                 200                 205

Ile Gly Thr Val Gly Pro Gly Asp Leu Trp Tyr Phe Pro Pro Gly Ile
            210                 215                 220

Pro His Ser Leu Gln Ala Thr Gly Asp Asp Pro Glu Gly Ser Glu Phe
225                 230                 235                 240

Ile Leu Val Phe Asp Ser Gly Ala Phe Ser Glu Asp Ser Thr Phe Leu
            245                 250                 255

Leu Thr Asp Trp Met Ser His Val Pro Val Glu Val Leu Ala Lys Asn
            260                 265                 270

Phe Gln Thr Asp Ile Ser Ala Phe Ala Arg Ile Pro Ala Glu Glu Leu
            275                 280                 285

Tyr Ile Phe Pro Ala Ala Val Pro Pro Asp Ser Gln Gln Asp Pro Thr
            290                 295                 300

Ser Pro Glu Gly Thr Val Pro Asn Pro Phe Thr Phe Ala Leu Ser Lys
305                 310                 315                 320

Val Pro Pro Met Gln Leu Ser Gly Gly Thr Ala Lys Ile Val Asp Ser
            325                 330                 335

Thr Thr Phe Thr Val Ser Lys Ala Ile Ala Ala Gly Val Thr Ile
            340                 345                 350

Glu Pro Gly Ala Ile Arg Glu Leu His Trp His Pro Thr Gln Asp Glu
            355                 360                 365

Trp Ser Phe Phe Ile Glu Gly Arg Ala Arg Met Thr Ile Phe Ala Ala
            370                 375                 380

Gln Ser Asn Ala Arg Thr Phe Asp Tyr Gln Ala Gly Asp Ile Gly Tyr
385                 390                 395                 400

Val Pro Ala Thr Met Gly His Tyr Val Glu Asn Ile Gly Asn Thr Thr
            405                 410                 415

Val Arg Tyr Leu Glu Ile Phe Asn Thr Ala Val Phe Glu Asp Ile Ser
            420                 425                 430

Leu Ser Asn Trp Leu Ala Leu Thr Pro Pro Glu Leu Val Lys Ala His
            435                 440                 445

Leu Gly Phe Asp Asp Ala Thr Met Ala His Leu Ala Lys Val Lys Pro
            450                 455                 460

Ile Val Val Gly Pro Ala
465                 470

<210> SEQ ID NO 2
<211> LENGTH: 472
<212> TYPE: PRT
<213> ORGANISM: Artificial Sequence
<220> FEATURE:
<223> OTHER INFORMATION: The sequence is synthetized.

<400> SEQUENCE: 2

Met Lys Pro Ser Thr Leu Tyr Ser Ser Leu Pro Trp Val Ile Thr Ser
1               5                   10                  15

Leu Val Thr Val Ala Val His Gly Ala Pro Thr Gly Thr Lys Ser Asn
            20                  25                  30

Pro Pro Leu Arg Gly Ser Glu Asn Leu Leu Gly Tyr Ser Ala Ser Asn
            35                  40                  45

Thr Val Thr Asp Gln Ser Thr Asp Glu Ile Pro Tyr Val Pro Val Pro
```

```
            50                  55                  60
Gly Gln Thr Asp Ala Ala Asp Leu Gly Val Tyr Leu Asp Phe Glu Asp
 65                  70                  75                  80

Ile Glu Asn Pro Gln Pro Val Arg Gly Ser Thr Gly Gly Thr Asp Pro
                 85                  90                  95

Gly Pro Arg Asn Asp Tyr Tyr Asp Arg Ile Asn Ser Asp Lys Leu Ala
                100                 105                 110

Pro Pro Gly Thr Asp Asn Gly Gln Thr Ile Asn Ala Gln Trp Pro Met
            115                 120                 125

Gly Leu Ser His Asn Arg Leu Gly Leu Asn Glu Ser Gly Trp Ala Arg
            130                 135                 140

Gln Glu Asn Glu Val Val Met Pro Gly Ala Thr Glu Met Ala Gly Val
145                 150                 155                 160

Asp Met Arg Leu Glu Ala Gly Ala Tyr Arg Glu Leu His Trp His Val
                165                 170                 175

Ala Ser Glu Trp Ser Leu Val Leu Asn Gly Ser Cys Arg Ile Glu Ala
                180                 185                 190

Val Asn Glu Asn Gly Gln Thr Phe Val Asp Asp Val Ser Ala Gly Asp
                195                 200                 205

Val Trp Phe Phe Pro Pro Gly Val Pro His Ser Ile Gln Ala Leu Asp
210                 215                 220

Ser Gly Val Glu Phe Leu Leu Ile Phe Asp Asp Gly Ser Phe Ser Glu
225                 230                 235                 240

Asp Asn Thr Phe Leu Ala Thr Glu Val Phe Ala His Gln Pro Arg Glu
                245                 250                 255

Val Leu Ala Lys Asn Phe Asp Leu Pro Val Ala Ala Phe Asp Asp Ile
                260                 265                 270

Pro Glu Asp Glu Leu Tyr Ile Phe Pro Gly Thr Pro Ala Pro Gln Asn
            275                 280                 285

Ile Glu Glu Gln Asn Val Thr Gly Ser Ala Gly Val Leu Pro Lys Ser
            290                 295                 300

Gln Ser Tyr Ser Tyr His Phe Ser Glu Gln Pro Ala His Glu Val Gln
305                 310                 315                 320

Gly Gly Ser Val Lys Ile Val Asp Ser Leu Thr Phe Pro Ile Ser Thr
                325                 330                 335

Asn Thr Ala Ala Ala Leu Val Thr Val His Pro Gly Gly Met Arg Glu
                340                 345                 350

Ile His Trp His Pro Ser Ser Asp Glu Trp Thr Phe Phe Ile Ser Gly
            355                 360                 365

Lys Ala Arg Ala Thr Leu Phe Thr Ala Pro Ser Thr Ala Thr Thr Phe
            370                 375                 380

Asp Tyr Arg Pro Gly Asp Val Gly Tyr Phe Pro Gln Ser Asn Ser His
385                 390                 395                 400

Tyr Ile Glu Asn Thr Gly Asp Glu Asp Leu Val Phe Leu Glu Val Leu
                405                 410                 415

Gln Thr Asp Gln Phe Ser Asp Ile Ser Leu Gly Gln Trp Ile Gly Ser
                420                 425                 430

Thr Pro Lys Gln Ile Val Ser Asp Thr Leu Asn Leu Pro Gln Ser Ala
            435                 440                 445

Leu Asp Arg Leu Lys Thr Glu Lys Met Tyr Val Val Ala Gly Ser Asn
450                 455                 460

Glu Thr Asp Val Ala Ala Thr Ala
465                 470
```

<210> SEQ ID NO 3
<211> LENGTH: 455
<212> TYPE: PRT
<213> ORGANISM: Artificial Sequence
<220> FEATURE:
<223> OTHER INFORMATION: The sequence is synthetized.

<400> SEQUENCE: 3

```
Met Ile Arg Leu Ser Ser Cys Leu Cys Ala Leu Leu Ala Thr Phe
1               5                   10                  15

Ala Ala Ala Ala Pro Ala Ser Asp Ser Ala Ser Ser Val Pro Ala
            20                  25                  30

Ser Ile Ser Ser Glu His Pro Ser Ser Thr Val Lys Pro Thr Gly Thr
        35                  40                  45

Thr Thr Gly Ser Thr Val Pro Ala Ser Glu Thr Val Pro Leu Ile Pro
    50                  55                  60

Leu Asp Pro Asn Phe Pro Leu Trp Asn Glu Ser Thr Thr Val Lys Pro
65                  70                  75                  80

Asp Ala Ile Arg Gly Ser Leu Gly Ala His Val Leu Gly Pro Thr Asn
                85                  90                  95

Glu Pro Ile Asp Lys Gln Asn Pro Asp Phe Leu Ala Pro Pro Thr Thr
            100                 105                 110

Asp His Gly Ser Leu Pro Asn Ala Lys Trp Pro Phe Ser Leu Ser His
        115                 120                 125

Asn Arg Leu Gln Thr Gly Gly Trp Ala Arg Gln Glu Asn Thr Gly Val
    130                 135                 140

Met Pro Ile Ala Glu Gln Met Ser Ser Val Asn Met Arg Leu Glu Pro
145                 150                 155                 160

Gly Ala Val Arg Glu Leu His Trp His Lys Thr Ala Glu Trp Ala Tyr
                165                 170                 175

Val Leu Lys Gly Thr Thr Gln Ile Ala Ala Thr Asp Pro Asn Gly Arg
            180                 185                 190

Asn Tyr Val Ala Asn Val Glu Pro Gly Asp Leu Trp Tyr Phe Pro Ala
        195                 200                 205

Gly Thr Pro His Ser Leu Gln Ala Thr Gly Asp Asn Pro Glu Gly Ser
    210                 215                 220

Glu Phe Ile Leu Val Phe Asp Val Gly Asp Phe Ser Glu Asp Ser Thr
225                 230                 235                 240

Phe Leu Leu Thr Asp Trp Leu Ala His Val Pro Val Glu Val Leu Ala
                245                 250                 255

Lys Asn Phe Gln Val Asp Pro Glu Ala Phe Lys Thr Val Pro Ala Glu
            260                 265                 270

Glu Leu Tyr Ile Phe Pro Ala Asn Pro Pro Gln Thr Glu Asp Ala Pro
        275                 280                 285

Lys Ser Pro Gln Gly Thr Val Glu Asn Pro Phe Ser Phe Pro Phe Ser
    290                 295                 300

Lys Val Lys Glu Thr Gln Leu Glu Gly Gly Ser Val Lys Val Val Asp
305                 310                 315                 320

Ser Thr Thr Phe Lys Ile Ser Lys Thr Ile Ala Ala Glu Val Thr
                325                 330                 335

Val Glu Pro Gly Ala Met Arg Glu Leu His Trp His Pro Thr Gln Asp
            340                 345                 350

Glu Trp Ser Phe Phe Leu Ser Gly Asn Ala Arg Val Thr Ile Phe Ala
        355                 360                 365
```

```
Ala Gln Ser Asn Ala Arg Thr Phe Asp Tyr Gln Ala Gly Asp Ile Gly
        370                 375                 380

Tyr Val Pro Gly Ala Met Gly His Tyr Val Glu Asn Thr Gly Asn Thr
385                 390                 395                 400

Thr Leu Arg Phe Leu Glu Ile Phe Arg Asp Asp Val Phe Gln Asp Val
                405                 410                 415

Ser Leu Asn Gln Trp Leu Ala Leu Thr Pro Pro Glu Leu Val Lys Ala
            420                 425                 430

His Leu Gly Phe Ser Asp Glu Val Ile Ser Lys Leu Thr Lys Lys Lys
        435                 440                 445

Lys Thr Val Val Gly Pro Ala
450                 455

<210> SEQ ID NO 4
<211> LENGTH: 447
<212> TYPE: PRT
<213> ORGANISM: Artificial Sequence
<220> FEATURE:
<223> OTHER INFORMATION: The sequence is synthetized.

<400> SEQUENCE: 4

Met Phe Asn Asn Phe Gln Arg Leu Leu Thr Val Ile Leu Leu Ser Gly
1               5                   10                  15

Phe Thr Ala Gly Val Pro Leu Ala Ser Thr Thr Thr Gly Thr Gly Thr
            20                  25                  30

Ala Thr Gly Thr Ser Thr Ala Ala Glu Pro Ser Ala Thr Val Pro Phe
        35                  40                  45

Ala Ser Thr Asp Pro Asn Pro Val Leu Trp Asn Glu Thr Ser Asp Pro
50                  55                  60

Ala Leu Val Lys Pro Glu Arg Asn Gln Leu Gly Ala Thr Ile Gln Gly
65                  70                  75                  80

Pro Asp Asn Leu Pro Ile Asp Leu Gln Asn Pro Asp Leu Leu Ala Pro
                85                  90                  95

Pro Thr Thr Asp His Gly Phe Val Gly Asn Ala Lys Trp Pro Phe Ser
            100                 105                 110

Phe Ser Lys Gln Arg Leu Gln Thr Gly Gly Trp Ala Arg Gln Gln Asn
        115                 120                 125

Glu Val Val Leu Pro Leu Ala Thr Asn Leu Ala Cys Thr Asn Met Arg
    130                 135                 140

Leu Glu Ala Gly Ala Ile Arg Glu Leu His Trp His Lys Asn Ala Glu
145                 150                 155                 160

Trp Ala Tyr Val Leu Lys Gly Ser Thr Gln Ile Ser Ala Val Asp Asn
                165                 170                 175

Glu Gly Arg Asn Tyr Ile Ser Thr Val Gly Pro Gly Asp Leu Trp Tyr
            180                 185                 190

Phe Pro Pro Gly Ile Pro His Ser Leu Gln Ala Thr Ala Asp Asp Pro
        195                 200                 205

Glu Gly Ser Glu Phe Ile Leu Val Phe Asp Ser Gly Ala Phe Asn Asp
    210                 215                 220

Asp Gly Thr Phe Leu Leu Thr Asp Trp Leu Ser His Val Pro Met Glu
225                 230                 235                 240

Val Ile Leu Lys Asn Phe Arg Ala Lys Asn Pro Ala Ala Trp Ser His
                245                 250                 255

Ile Pro Ala Gln Gln Leu Tyr Ile Phe Pro Ser Glu Pro Pro Ala Asp
            260                 265                 270
```

Asn Gln Pro Asp Pro Val Ser Pro Gln Gly Thr Val Pro Leu Pro Tyr
        275                 280                 285

Ser Phe Asn Phe Ser Ser Val Glu Pro Thr Gln Tyr Ser Gly Gly Thr
    290                 295                 300

Ala Lys Ile Ala Asp Ser Thr Thr Phe Asn Ile Ser Val Ala Ile Ala
305                 310                 315                 320

Val Ala Glu Val Thr Val Glu Pro Gly Ala Leu Arg Glu Leu His Trp
                325                 330                 335

His Pro Thr Glu Asp Glu Trp Thr Phe Phe Ile Ser Gly Asn Ala Arg
                340                 345                 350

Val Thr Ile Phe Ala Ala Gln Ser Val Ala Ser Thr Phe Asp Tyr Gln
                355                 360                 365

Gly Gly Asp Ile Ala Tyr Val Pro Ala Ser Met Gly His Tyr Val Glu
        370                 375                 380

Asn Ile Gly Asn Thr Thr Leu Thr Tyr Leu Glu Val Phe Asn Thr Asp
385                 390                 395                 400

Arg Phe Ala Asp Val Ser Leu Ser Gln Trp Leu Ala Leu Thr Pro Pro
                405                 410                 415

Ser Val Val Gln Ala His Leu Asn Leu Asp Asp Glu Thr Leu Ala Glu
                420                 425                 430

Leu Lys Gln Phe Ala Thr Lys Ala Thr Val Val Gly Pro Val Asn
        435                 440                 445

<210> SEQ ID NO 5
<211> LENGTH: 470
<212> TYPE: PRT
<213> ORGANISM: Artificial Sequence
<220> FEATURE:
<223> OTHER INFORMATION: The sequence is synthetized.

<400> SEQUENCE: 5

Met Ile Ser Phe Ala Ser Cys Val Cys Ala Leu Leu Phe Ala Arg Leu
1               5                   10                  15

Ala Leu Ser Ala Pro Ala Pro Ala Ala Ser Ser Ser Ala Pro Thr Val
                20                  25                  30

Ser Thr Val Ser Ser Val Ile Ala Pro Ile Ser Pro Thr Ala Glu Ser
            35                  40                  45

Ser Val Ala Ala Ser Ser Ala Ser Asn Lys Pro Arg Pro Thr Ser Thr
        50                  55                  60

Ala Thr Ala Thr Glu Pro Thr Ala Thr Val Pro Phe Ile Asp Leu Asp
65                  70                  75                  80

Pro Asn Glu Pro Leu Trp Asn Glu Asp Thr Pro Gly Ile His Gln Pro
                85                  90                  95

Ile His Gly Ser Leu Gly Ala Lys Leu Leu Gly Pro Thr Asn Asn Ala
            100                 105                 110

Ile Val Lys Gln Asn Pro Asp Leu Leu Ala Pro Pro Thr Thr Asp His
        115                 120                 125

Gly Ser Val Pro Asn Ala Lys Trp Pro Phe Ser Leu Ser His Asn Arg
    130                 135                 140

Leu Gln Thr Gly Gly Trp Ala Arg Glu Glu Asn Ile Ala Val Met Pro
145                 150                 155                 160

Val Ala Gln Ala Met Ala Ser Val Asn Met Arg Leu Glu Ala Gly Ala
                165                 170                 175

Val Arg Glu Leu His Trp His Lys Thr Ala Glu Trp Ala Tyr Val Leu
                180                 185                 190

```
Lys Gly Ser Thr Gln Val Thr Ala Val Asp Ala Asp Gly Arg Asn Phe
            195                 200                 205
Val Ser Thr Val Gly Pro Gly Asp Leu Trp Tyr Phe Pro Pro Gly Ile
    210                 215                 220
Pro His Ser Leu Gln Ala Thr Asn Asp Pro Asp Gly Ser Glu Phe
225                 230                 235                 240
Val Leu Val Phe Asp Ser Gly Ser Phe Ser Glu Asp Ser Thr Phe Leu
                245                 250                 255
Leu Thr Asp Trp Leu Asp His Val Pro Ala Glu Val Leu Ala Lys Asn
                260                 265                 270
Phe Gln Val Asn Ile Ser Ala Phe Ala His Ile Pro Ala Glu Glu Leu
            275                 280                 285
Tyr Ile Phe Pro Ala Ala Leu Pro Glu Pro Asp Ser Ala Ala Pro Lys
        290                 295                 300
Ser Pro Gln Gly Thr Val Pro Asp Pro Phe Ser Phe Ser Met Ser Lys
305                 310                 315                 320
Val Lys Pro Thr Gln Leu Thr Gly Gly Thr Val Lys Val Val Asp Ser
                325                 330                 335
Thr Thr Phe Lys Ile Ser Lys Thr Ile Ala Ala Ala Glu Val Thr Val
                340                 345                 350
Glu Pro Gly Ala Ile Arg Glu Leu His Trp His Pro Thr Gln Asp Glu
            355                 360                 365
Trp Ser Phe Phe Ile Glu Gly Glu Gly Arg Met Thr Ile Phe Ala Ser
        370                 375                 380
Gln Ser Asn Ala Arg Thr Phe Asn Tyr Gln Ala Gly Asp Ile Gly Tyr
385                 390                 395                 400
Val Pro Ala Thr Met Gly His Tyr Leu Glu Asn Thr Gly Asn Thr Thr
                405                 410                 415
Leu Arg Phe Leu Glu Ile Phe Lys Ser Glu Lys Phe Gln Asp Ile Ser
                420                 425                 430
Leu Ala Gln Trp Leu Ala Leu Thr Pro Pro Lys Leu Val Lys Glu His
            435                 440                 445
Leu Gly Phe Ser Asp Asp Val Ile Ala Arg Leu Ser Lys Thr Lys Leu
        450                 455                 460
Thr Val Val Gly Pro Lys
465                 470

<210> SEQ ID NO 6
<211> LENGTH: 455
<212> TYPE: PRT
<213> ORGANISM: Artificial Sequence
<220> FEATURE:
<223> OTHER INFORMATION: The sequence is synthetized.

<400> SEQUENCE: 6

Met Gly Lys Phe Leu Ala Thr Val Leu Cys Ala Val Leu Tyr Gly Ser
1               5                   10                  15
Leu Ala Ala Ala Ile Pro Val Gly Asp Val Ser Ala Ser Ser Ser Ala
                20                  25                  30
Ser Ser Ser Ile Ala Glu Ala Ala Thr Ser Thr Ser Gly Gly Ala Ser
            35                  40                  45
Pro Ser Pro Thr Val Pro Leu Ala Ser Asp Asp Pro Asn Tyr Trp Leu
        50                  55                  60
Trp Asn Glu Thr Thr Thr Thr Asp Pro Gln Pro Glu Arg Gly Ser Leu
65                  70                  75                  80
```

-continued

Gly Ala Asn Ile Leu Gly Pro Gln Asn Val Ala Ile Asp Lys Gln Asn
                85                  90                  95

Pro Asp Ile Leu Ala Pro Pro Thr Thr Asp Gln Gly Thr Val Gly Asn
            100                 105                 110

Ala Lys Trp Pro Phe Ser Leu Ser Lys Gln Gln Leu Asn Thr Gly Gly
        115                 120                 125

Trp Val Arg Gln Gln Asn Val Gln Gln Met Pro Ile Ala Thr Ala Met
130                 135                 140

Ala Gly Val Asn Met Arg Leu Glu Ser Gly Ala Ile Arg Glu Leu His
145                 150                 155                 160

Trp His Gln Thr Ala Glu Trp Ala Tyr Val Leu Ser Gly Ser Thr Gln
                165                 170                 175

Ile Ser Ser Val Asp Gln Leu Gly Arg Asn Tyr Val Ala Thr Val Arg
            180                 185                 190

Gln Gly Asp Leu Trp Tyr Phe Pro Pro Gly Ile Pro His Ser Leu Gln
        195                 200                 205

Ala Thr Asn Asp Ser Ser Glu Gly Thr Glu Phe Leu Leu Ile Phe Pro
210                 215                 220

Asp Gly Asn Phe Asn Asp Asp Thr Leu Leu Leu Thr Asp Trp Leu
225                 230                 235                 240

Ala His Thr Pro Lys Glu Val Ile Ala Lys Asn Phe Gln Asp Asn Ile
                245                 250                 255

Ala Asp Trp Asp Asp Ile Pro Gly Ser Gln Leu Tyr Ile Phe Pro Gly
            260                 265                 270

Val Pro Pro Asp Asn Gln Gln Pro Thr Ser Pro Ala Gly Glu
        275                 280                 285

Ile Pro Gln Pro Phe Ser Tyr Ala Phe Ser Glu Ile Thr Pro Thr Gln
290                 295                 300

Tyr Thr Gly Gly Thr Ala Lys Ile Ala Asp Ser Thr Thr Phe Lys Val
305                 310                 315                 320

Ala Thr Lys Ile Ala Val Ala Glu Val Thr Val Glu Pro Gly Ala Met
                325                 330                 335

Arg Glu Met His Trp His Pro Thr Gln Ser Glu Trp Gly Phe Phe Leu
            340                 345                 350

Glu Gly Thr Ala Arg Val Thr Leu Phe Ala Gly Thr Ala Ile Ala Gln
        355                 360                 365

Thr Phe Asp Tyr Gln Pro Gly Asp Ile Ser Tyr Ile Pro Thr Ala Tyr
370                 375                 380

Gly His Tyr Val Glu Asn Thr Gly Asn Thr Thr Leu Lys Phe Leu Glu
385                 390                 395                 400

Ile Phe Asn Ser Asp Val Phe Gln Asp Val Ser Leu Ala Gln Trp Leu
                405                 410                 415

Ala Leu Thr Pro Pro Ala Leu Val Lys Gln His Leu Gln Leu Ser Asp
            420                 425                 430

Ala Thr Ile Ser Arg Phe Asn Arg Thr Lys Gly Val Val Gly Gly
        435                 440                 445

Pro Gly Ala Asn Val Ser Ser
    450                 455

<210> SEQ ID NO 7
<211> LENGTH: 440
<212> TYPE: PRT
<213> ORGANISM: Artificial Sequence
<220> FEATURE:

<223> OTHER INFORMATION: The sequence is synthetized.

<400> SEQUENCE: 7

```
Met Arg Arg Gln Leu Val Thr Arg Leu Gln Ser Leu Val Val Ala Ala
1               5                   10                  15

Val Cys Ala Ala Ser Val Thr Ala Ile Pro Leu Ala Pro Ser Leu Thr
            20                  25                  30

Glu Ser Ala Pro Ala Tyr Pro Ser Pro Thr Val Pro Tyr Ala Thr Asp
        35                  40                  45

Asp Pro Asn Arg Glu Leu Trp Asn Pro Leu Ser Asn Val Asp Pro Gln
    50                  55                  60

Pro Ile Arg Gly Thr Leu Gly Ala Asp Ile Ile Ala Gln Gln Asn Val
65                  70                  75                  80

Pro Leu Gln Leu Gln Asn Ser Asp Leu Leu Ala Pro Thr Thr Asp
                85                  90                  95

His Gly Ser Val Pro Asn Ile Lys Trp Pro Phe Thr Leu Ser His Asn
            100                 105                 110

Arg Leu His Thr Gly Gly Trp Ala Arg Gln Gln Asn Ile His Asp Leu
        115                 120                 125

Pro Ile Ser Thr Glu Met Ala Gly Val Asp Met Arg Leu Glu Ala Gly
    130                 135                 140

Ala Ile Arg Glu Leu His Trp His Thr Ala Ala Glu Trp Ala Tyr Val
145                 150                 155                 160

Leu Lys Gly Ser Thr Gln Val Ser Thr Val Thr Pro Asp Gly Gln Asn
                165                 170                 175

Tyr Val Ala Thr Ala Asn Gln Gly Asp Leu Trp Tyr Phe Pro Pro Gly
            180                 185                 190

Gln Pro His Ser Leu Gln Ala Thr Ala Gln Asp Pro Asp Gly Thr Glu
        195                 200                 205

Phe Leu Leu Val Phe Asp Asn Gly Glu Phe Ser Glu Asp Ser Thr Phe
    210                 215                 220

Leu Leu Thr Asp Trp Leu Ala His Val Pro Lys Glu Val Leu Val Arg
225                 230                 235                 240

Asn Phe Gln Ala Thr Lys Ser Ala Phe Asp His Ile Pro Asp Arg Glu
                245                 250                 255

Leu Tyr Ile Phe Pro Gly Val Pro Pro Asp Pro Asn Ala Gln Pro Pro
            260                 265                 270

Ser Ser Pro Gln Gly Gln Thr Pro Leu Pro Tyr Thr Phe Pro Leu Ser
        275                 280                 285

Gln Val Glu Ala Thr Lys Phe Pro Gly Gly Thr Thr Lys Ile Val Asp
    290                 295                 300

Ser Thr Thr Phe Lys Val Ser Lys Thr Met Ala Val Ala Glu Val Thr
305                 310                 315                 320

Leu Glu Pro Gly Ala Met Arg Glu Leu His Trp His Pro Thr Gln Thr
                325                 330                 335

Glu Trp Asp Tyr Phe Met Ser Gly Tyr Ala Arg Val Thr Val Phe Ala
            340                 345                 350

Ala Asn Ala Asp Ala Arg Thr Phe Asp Phe Gln Ala Gly Asp Ile Gly
        355                 360                 365

Tyr Ile Pro Gln Ser Tyr Gly His Tyr Ile Glu Asn Thr Gly Asn Thr
    370                 375                 380

Thr Leu His Phe Leu Glu Ile Leu Lys Thr Asp Ile Asp Lys Phe Gln
385                 390                 395                 400
```

-continued

Asp Val Ser Leu Ala Gln Trp Leu Ala Leu Thr Pro Pro Ala Val Val
            405                 410                 415

Lys Ala His Leu Asp Val Ser Asp Thr Ile Ala Ala Phe Ser Lys
            420                 425                 430

Thr Lys Gln Arg Ile Val Gly Lys
            435                 440

<210> SEQ ID NO 8
<211> LENGTH: 472
<212> TYPE: PRT
<213> ORGANISM: Artificial Sequence
<220> FEATURE:
<223> OTHER INFORMATION: The sequence is synthetized.

<400> SEQUENCE: 8

Met Lys Pro Ser Thr Leu Tyr Ser Leu Pro Trp Val Ile Thr Ser
1               5                   10                  15

Leu Leu Thr Val Ala Val His Gly Ala Pro Thr Gly Thr Lys Ser Asn
                20                  25                  30

Pro Pro Leu Arg Gly Ser Glu Asn Leu Leu Gly Tyr Ser Ala Ser Asn
            35                  40                  45

Thr Val Thr Asp Gln Ser Thr Asp Glu Ile Pro Tyr Val Pro Val Pro
    50                  55                  60

Gly Gln Thr Asp Ala Ala Asp Leu Gly Val Tyr Leu Asp Phe Glu Asp
65                  70                  75                  80

Ile Glu Asn Pro Gln Pro Val Arg Gly Ser Thr Gly Gly Thr Asp Pro
                85                  90                  95

Gly Pro Arg Asn Asp Tyr Tyr Asp Arg Ile Asn Ser Asp Lys Leu Ala
            100                 105                 110

Pro Pro Gly Thr Asp Asn Gly Gln Thr Ile Asn Ala Gln Trp Pro Met
        115                 120                 125

Gly Leu Ser His Asn Arg Leu Gly Leu Asn Glu Ser Gly Trp Ala Arg
    130                 135                 140

Gln Glu Asn Glu Val Val Met Pro Gly Ala Thr Glu Met Ala Gly Val
145                 150                 155                 160

Asp Met Arg Leu Glu Ala Gly Ala Tyr Arg Glu Leu His Trp His Val
                165                 170                 175

Ala Ser Glu Trp Ser Leu Val Leu Asn Gly Ser Cys Arg Ile Glu Ala
            180                 185                 190

Val Asn Glu Asn Gly Gln Thr Phe Val Asp Asp Val Ser Ala Gly Asp
        195                 200                 205

Val Trp Phe Phe Pro Pro Gly Val Pro His Ser Ile Gln Ala Leu Asp
    210                 215                 220

Ser Gly Val Glu Phe Leu Leu Ile Phe Asp Asp Gly Ser Phe Ser Glu
225                 230                 235                 240

Asp Asn Thr Phe Leu Ala Thr Glu Val Phe Ala His Gln Pro Arg Glu
                245                 250                 255

Val Leu Ala Lys Asn Phe Asp Leu Pro Val Ala Ala Phe Asp Asp Ile
            260                 265                 270

Pro Glu Asp Glu Leu Tyr Ile Phe Pro Gly Thr Pro Ala Pro Gln Asn
        275                 280                 285

Ile Glu Glu Gln Asn Val Thr Gly Ser Ala Gly Val Leu Pro Lys Ser
    290                 295                 300

Gln Ser Tyr Ser Tyr His Phe Ser Glu Gln Pro Ala His Glu Val Gln
305                 310                 315                 320

```
Gly Gly Ser Val Lys Ile Val Asp Ser Leu Thr Phe Pro Ile Ser Thr
            325                 330                 335

Asn Thr Ala Ala Ala Leu Val Thr Val His Pro Gly Gly Met Arg Glu
        340                 345                 350

Ile His Trp His Pro Ser Ser Asp Glu Trp Thr Phe Phe Ile Ser Gly
    355                 360                 365

Lys Ala Arg Ala Thr Leu Phe Thr Ala Pro Ser Thr Ala Thr Thr Phe
370                 375                 380

Asp Tyr Arg Pro Gly Asp Val Gly Tyr Phe Pro Gln Ser Asn Ser His
385                 390                 395                 400

Tyr Ile Glu Asn Thr Gly Asp Glu Asp Leu Val Phe Leu Glu Val Leu
                405                 410                 415

Gln Thr Glu Gln Phe Ser Asp Ile Ser Leu Gly Gln Trp Ile Gly Ser
            420                 425                 430

Thr Pro Lys Gln Ile Val Ser Asp Thr Leu Asn Leu Pro Gln Ser Ala
        435                 440                 445

Leu Asp Arg Leu Lys Thr Glu Lys Met Tyr Val Val Ala Gly Ser Asn
    450                 455                 460

Glu Thr Asp Val Ala Ala Thr Ala
465                 470
```

<210> SEQ ID NO 9
<211> LENGTH: 1413
<212> TYPE: DNA
<213> ORGANISM: Artificial Sequence
<220> FEATURE:
<223> OTHER INFORMATION: The sequence is synthetized.

<400> SEQUENCE: 9

| | | | | | |
|---|---|---|---|---|---|
| atgatcagtg | tcgcgtcttg | cactattgca | ctcttgctat | cgagtgttgc | ctttgccgca | 60 |
| ccagcaccca | gttctgctgc | gtccagcatt | gttgtcagtg | caacttcgtc | gtcgactgtg | 120 |
| tcctctgcgc | ccgtctctgt | ctcttctttt | ttaccgacga | cgtcaatagc | tgcagcgact | 180 |
| ccatcctcga | ttgctgttgc | cttatcctct | accgcaaccg | tcccttcat | cgacctgaat | 240 |
| ccaaatggcc | ctttatggga | tccctccgtc | agtggggttc | ctcaggccga | aagaggttct | 300 |
| ctagggcaa | ccatcatggg | cccgacagac | gtcgacacta | ctaaggccaa | ccccgatctt | 360 |
| ctggcacctc | cgactacaga | tcatggtagc | gtggacaacg | ccaaatgggc | attcagtttg | 420 |
| agccacaacc | gccttcagac | tggaggctgg | gctcgcgagc | agaacatcgg | cgccatgccc | 480 |
| attgccacag | aaatggccag | cgttaacatg | agactcgagc | ctggcgctat | tcgcgaactt | 540 |
| cactggcaca | agactgcaga | gtgggcatat | gttctcaagg | gcaacaccca | agtcactgca | 600 |
| gtcgatcaga | atggaaagaa | cttcattggc | actgtgggcc | ctggtgatct | ttggtacttc | 660 |
| ccgcctggca | taccccactc | tcttcaagca | acaggcgacg | acccagaggg | ttctgaattc | 720 |
| attctggtct | tcgatagtgg | tgcttttcagc | gaagattcga | cctttttgct | gactgattgg | 780 |
| atgtcccacg | ttccggtcga | agtcctcgca | aagaacttcc | aaacagatat | ctctgcattt | 840 |
| gctcgtatac | cagccgaaga | actctacata | ttcccagctg | ctgttccgcc | tgacagccag | 900 |
| caagacccaa | ccagccctga | aggaactgtt | cccaatcctt | ttaccttcgc | gctatcgaag | 960 |
| gttcctccga | tgcagctaag | cggcggtact | gctaagatcg | tggactctac | cacttttaca | 1020 |
| gtatccaaag | caatcgcagc | ggcggaggtc | actatcgaac | ccggagctat | cagagaactg | 1080 |
| cattggcatc | ccacacagga | cgagtggagc | tttttcattg | aagggcgtgc | gcgaatgacg | 1140 |
| attttcgctg | cccaatccaa | tgcacggact | ttcgactatc | aggctgggga | tattggttac | 1200 |

| | |
|---|---|
| gttcctgcca cgatgggcca ttacgtcgag aacattggta acaccaccgt gcgttacctt | 1260 |
| gaaatattta acacggccgt tttcgaggat atttcgctca gcaattggct tgcttttgacc | 1320 |
| cctccagaat tagtcaaggc ccaccttggc ttcgatgatg cgaccatggc ccacctggcg | 1380 |
| aaggtcaagc caatcgttgt cggtcccgct tag | 1413 |

<210> SEQ ID NO 10
<211> LENGTH: 1419
<212> TYPE: DNA
<213> ORGANISM: Artificial Sequence
<220> FEATURE:
<223> OTHER INFORMATION: The sequence is synthetized.

<400> SEQUENCE: 10

| | |
|---|---|
| atgaaaccat ctactcttta ctcttctcta ccttgggtca tcacgtccct cgtcacggta | 60 |
| gctgttcatg gcgctcctac agggacgaag tccaatcctc ccctacgagg ctccgagaac | 120 |
| ttgctgggtt actcggcctc caacaccgta acgaccagt ccaccgacga gatcccttat | 180 |
| gtgccggtgc caggacagac cgatgccgct gacctcggcg tataccctgga ctttgaagat | 240 |
| atcgagaacc cgcaacccgt ccgcggaagc acgggaggaa ctgaccctgg acctcgcaac | 300 |
| gactactacg accggattaa tagcgataag ctggctcctc cgggtacgga caatggccag | 360 |
| acgatcaatg cccaatggcc tatgggacta agccataatc ggctgggatt gaacgagtct | 420 |
| ggatgggctc ggcaagagaa cgaggtggtg atgccgggcg cgaccgagat ggctggagtg | 480 |
| gatatgcgcc tagaagcagg tgcttatcgg gagctgcatt ggcatgtggc atcggaatgg | 540 |
| tcgttggtgt tgaacggatc gtgtcggatc gaggccgtca cgagaacgg acaaactttc | 600 |
| gtcgatgacg tgagcgctgg tgatgtctgg ttcttccctc ccgtgttcc gcattccatc | 660 |
| caagccctcg actcgggcgt cgagtttctc ctcatcttcg atgacggttc cttctctgag | 720 |
| gataatactt tcctcgccac tgaagtgttt gcccatcaac cgcgcgaggt cctcgccaaa | 780 |
| aacttcgacc tccccgttgc cgctttcgac gacattcccg aagatgaact ttatatcttc | 840 |
| cccggcactc cggcaccgca aaacatcgag agcaaaatg taactggctc tgcaggcgtc | 900 |
| ttgcccaagt cccaaagcta ctcgtaccac ttctccgagc agcccgcgca cgaagtgcaa | 960 |
| ggcggatccg tcaagatcgt cgactccctc accttcccca tctccaccaa cacggctgcc | 1020 |
| gcgctggtga cagtgcaccc aggtggcatg cgtgaaattc attggcaccc aagcagcgat | 1080 |
| gaatggacgt tcttcattag tggcaaggca cgcgcgaccc tgttcacggc gcccagcacc | 1140 |
| gccacgacgt tcgattaccg cccgggggat gtaggatact ccccacagag caacagccat | 1200 |
| tatatcgaga acacaggaga tgaggatctg gttttcttgg aggtgttgca gacggatcaa | 1260 |
| ttcagcgaca tctcattggg ccagtggatc ggctccacgc cgaagcagat tgtctcggat | 1320 |
| acgctgaacc tgccgcagag tgcgctggat cggttgaaga cggagaagat gtatgtggtg | 1380 |
| gctggatcaa atgagacgga tgttgctgct actgcgtag | 1419 |

<210> SEQ ID NO 11
<211> LENGTH: 1368
<212> TYPE: DNA
<213> ORGANISM: Artificial Sequence
<220> FEATURE:
<223> OTHER INFORMATION: The sequence is synthetized.

<400> SEQUENCE: 11

| | |
|---|---|
| atgatacgtc tctcttcatg tctctgtgct ttactcttgg ctacctttgc cgctgctgct | 60 |

```
cctgcggcat ctgactctgc atctagtgtc cccgcatcga tctcgtccga acacccatct    120
tcgactgtga aacccactgg tacaacaacg ggcagcacag tccctgcaag tgagaccgtc    180
ccactcatcc cattggaccc aaattttccg ttgtggaacg agtcgaccac ggtcaaacca    240
gatgcaatcc gtggttctct cggcgctcac gttttaggcc cacaaacga gcccatcgat     300 aaacagaacc cagacttcct ggctccacct acgacagatc atggaagcct cccgaacgca    360
aagtggccct tctctttgag tcacaacagg ttgcaaactg gtggatgggc tcgtcaagag    420
aatactggtg tcatgccgat tgctgaacaa atgtcaagtg tgaacatgag gttagaacct    480
ggagcggtga gagaattgca ttggcacaag acggctgagt gggcgtatgt actcaaggga    540
accacccaaa ttgcggccac agaccctaat ggacggaact atgttgccaa tgttgaaccc    600
ggtgaccttt ggtatttccc cgcaggcact ccccattccc tccaggctac cggagataat    660
ccagagggct ctgaatttat tttggtcttc gacgttggcg acttcagcga agattcgacc    720
ttccttctca ctgattggct cgcccacgtt ccagtagaag tgctcgcgaa gaacttccaa    780
gtcgaccccg aggcgttcaa aacggtccca gcagaagaac tatatatctt ccctgccaac    840
cctccccaga ctgaggatgc tcccaaatcc ccgcagggta ccgtggagaa cccattctct    900 ttccctttt cgaaagtaaa ggaaactcag ctcgagggtg gcagcgttaa ggtagtcgat      960
tccaccacct tcaagatctc aaagaccatt gcggcggctg aagtaaccgt cgaacctgga    1020
gcaatgcgcg aactccattg gcacccaaca caagacgagt ggagcttctt cctatcgggt    1080
aatgctcgag tgactatctt cgcggcacag tccaacgcac gtacatttga ttatcaggct    1140
ggtgatatcg gttacgttcc tggggcaatg ggtcattacg ttgaaaacac tgggaacaca    1200
accctgaggt tccttgagat tttcagagac gacgttttcc aggatgtcag tttgaaccag    1260
tggttggctc ttactccgcc cgagttggtc aaggcgcatc ttggattctc agatgaggtt    1320
atttcgaaac tgactaagaa gaagaaaact gttgtcggac ccgcttaa                 1368
```

<210> SEQ ID NO 12
<211> LENGTH: 1344
<212> TYPE: DNA
<213> ORGANISM: Artificial Sequence
<220> FEATURE:
<223> OTHER INFORMATION: The sequence is synthetized.

<400> SEQUENCE: 12

```
atgtttaaca acttccagag attgttgact gttatcttgt tgtccggttt cactgctggt     60
gtcccattgg catccactac tactggtact ggaactgcta ctggtacttc tactgctgct    120
gaaccatctg ctactgttcc tttcgcttcc actgatccaa accctgtttt gtggaacgaa    180
acttccgatc cagctttggt taagccgagt agaaaccagt tgggagctac tattcaaggt    240
ccagacaact tgccaatcga cttgcaaaac ccagatttgt tggctccacc aactactgat    300 cacggttttcg ttggtaacgc taagtggcca ttctcattct ccaagcagag attgcaaact    360
ggtggatggg ctagacaaca gaacgaagtt gttttgccat ggctacaaa cttggcttgt    420 acaaacatga gattggaggc tgtgctatt agagaattgc actggcacaa gaacgctgaa    480
tgggcttacg ttttgaaggg ttccactcag atttctgctg ttgacaacga gggtagaaac    540
tacatctcca ctgttggtcc tggtgatttg tggtacttcc caccaggtat ccacattcc     600 ttgcaggcta ctgctgatga tccagaaggt tccgagttca tcttggtttt cgactccggt    660
gctttcaacg atgacggtac tttccttgttg actgattggt tgtcccacgt tccaatggaa    720
gttatcttga agaacttcag agctaagaac cctgctgctt ggtcacatat tccagctcaa    780
```

```
cagttgtaca tcttcccatc tgaacctcca gctgataacc aaccagaccc agtttctcca      840
caaggtactg ttccattgcc atactcattc aacttctcat ccgttgagcc aactcaatac      900
tctggtggta ctgctaagat tgctgactcc actactttca acatctccgt tgctattgct      960
gttgctgagg ttacagttga acctggtgct ttgagagagt tgcattggca tccaactgaa     1020
gatgagtgga ctttcttcat ctccggtaac gctagagtta ctatcttcgc tgctcaatcc     1080
gttgcttcca ctttcgatta ccagggtggt gacattgctt acgttccagc ttctatggga     1140
cactacgttg agaacatcgg taacactact ttgacttact ggaggtttt caacactgac      1200 agattcgctg acgtttcttt gtctcagtgg cttgctttga ctccaccatc tgttgttcag     1260
gctcacttga acttggacga cgaaactttg gctgagttga agcagtttgc tactaaggct     1320
actgttgttg gtccagttaa ctaa                                             1344

<210> SEQ ID NO 13
<211> LENGTH: 1413
<212> TYPE: DNA
<213> ORGANISM: Artificial Sequence
<220> FEATURE:
<223> OTHER INFORMATION: The sequence is synthetized.

<400> SEQUENCE: 13
atgattagct ttgcctcttg tgtttgtgcg cttctctttg cacggttggc tctttcagca       60
cctgcacctg ctgcgtcgtc ttccgcacct actgtgagca cggtgtcttc agtcattgca      120
ccaatcagcc ccaccgccga aagttcagtt gctgcctcca gtgcctcaaa caaacctcgt      180
ccaacctcga cggcgactgc cacggaaccg actgcaacgg tgcctttcat tgacctcgac      240
cctaatgagc cgctttggaa cgaggacact cctggaatcc atcaaccaat tcatggctca      300
cttggagcca agcttctcgg accgacaaac aacgcgatcg tcaagcagaa ccccgactta      360
ctcgctcctc ccaccactga tcacggcagc gtacccaatg ccaaatggcc tttcagtctt      420
agtcataatc gactccaaac tggaggctgg gcgcgtgaag aaaatattgc tgtaatgcct      480
gtcgcccagg ctatggccag tgtcaacatg cgccttgaag ctggtgcagt aagagaactc      540
cactggcata agactgcaga gtgggcatat gttctgaagg ctccaccca agtcacagcc       600 gtggatgccg atgggcgtaa cttcgtctcc accgttggcc ctggtgacct ttggtacttc      660
ccacctggta tccctcattc acttcaagca acgaatgacg accctgatgg ttctgagttc      720
gtcttggtct tcgactcagg ctctttagt gaagattcaa cgttcttgct aactgattgg      780
ttggatcacg ttcagctga agtattggcc aaaaatttcc aagtcaacat ctctgccttc      840
gcacacattc ctgctgagga actctacatt ttccccgctg cactgccgga gctgatagc      900 gctgctccga aaagtccgca aggcactgtc cctgatccat tttcatttc aatgtcaaag      960 gtcaagccca cccagctgac gggaggcacc gtcaaggttg tggattccac taccttcaag     1020
atctccaaga ctattccgc tgcagaggtc actgttgaac caggtgcaat tagggagctc      1080
cattggcacc cgactcaaga cgaatggagt ttctttattg agggtgaagg tcgaatgacc     1140
attttcgcct cgcagtccaa tgcccgaacg ttcaactatc aggctggtga tatcggctat     1200
gttcccgcaa ccatggggca ttacctcgag aacaccggca acacgacact aaggttcctg     1260
gagattttca gtccgagaa attccaggat atcagtttgg ctcagtggct tgcattgacc      1320
cctccaaaat tggtcaaaga gcatttaggt ttctctgacg acgtcattgc tcggctttcg     1380
aagactaagc ttaccgtggt tggtccgaag tga                                   1413
```

<210> SEQ ID NO 14
<211> LENGTH: 1368
<212> TYPE: DNA
<213> ORGANISM: Artificial Sequence
<220> FEATURE:
<223> OTHER INFORMATION: The sequence is synthetized.

<400> SEQUENCE: 14

```
atgggaaagt tcttggctac tgttttgtgt gctgttttgt acggttcttt ggctgctgct      60
attccagttg gtgacgtttc tgcttcttct tctgcatcat catctattgc tgaggctgct     120
acttctactt ctggtggtgc ttctccatct ccaactgttc cattggcttc cgatgatcct     180
aactactggt tgtggaacga actactact actgacccac aaccagaaag aggatccttg      240
ggagctaaca ttttgggtcc acagaacgtt gctatcgaca agcaaaaccc agacattttg     300
gctccaccaa ctactgatca gggtactgtt ggtaacgcta gtggccatt ctctttgtcc      360
aagcagcagt tgaatactgg tggatgggtt agacaacaga acgttcagca gatgccaatt    420
gctactgcta tggctggtgt taacatgaga ttggagtccg gtgctattag agaattgcac    480
tggcaccaaa ctgctgaatg ggcttacgtt ttgtccggtt ccactcagat ttcttccgtt    540
gaccagttgg gtagaaacta cgttgctact gttagacagg gagacttgtg gtactttcca    600
ccaggtatcc cacattcctt gcaggctact aatgactctt ctgagggtac tgagttcttg    660
ttgatcttcc cagacggtaa cttcaacgac gacgacactt gttgttgac tgactggctt    720
gctcacactc caaaagaggt tatcgctaag aacttccagg acaacattgc tgattgggac    780
gacattccag gttcccagtt gtacatcttc ccaggtgttc caccaccaga taaccaacaa    840
ccaccaactt ctccagctgg tgaaattcca cagccattct cttacgcttt ctccgagatc    900
actccaactc aatacactgg tggtactgct aagattgctg actccactac tttcaaagtt    960
gctactaaga tcgctgttgc tgaggttaca gttgaaccag gtgctatgag agagatgcat   1020
tggcatccta ctcaatctga gtggggattc ttcttggaag gtactgctag agttactttg   1080
ttcgctggta ctgctattgc tcagactttc gactaccaac aggtgacat tcctacatc    1140
ccaactgctt acggtcacta cgttgagaac actggtaaca ctactttgaa gttcttggag   1200
atcttcaact ccgacgtttt ccaagacgtt tccttggctc aatggcttgc tttgactcct   1260
ccagcttttgg ttaagcagca cttgcaattg tccgacgcta ctatctccag attcaacaga   1320
actaagggtg ttgttgttgg tggtccaggt gctaacgttt catcctaa                 1368
```

<210> SEQ ID NO 15
<211> LENGTH: 1323
<212> TYPE: DNA
<213> ORGANISM: Artificial Sequence
<220> FEATURE:
<223> OTHER INFORMATION: The sequence is synthetized.

<400> SEQUENCE: 15

```
atgagaagac agttggttac tagattgcag tccttggttg ttgctgctgt ttgtgctgct      60
tccgttactg ctattccatt ggctccatcc ttgactgaat ctgctccagc ttacccatct     120
ccaactgttc catacgctac tgacgaccca aacagagaat tgtggaaccc attgtccaac    180
gttgacccac aaccaatcag aggaactttg ggtgctgaca ttatcgctca acagaacgtt    240
ccattgcagt tgcaaaactc cgatttgttg gctccaccaa ctactgatca cggttccgtt    300
ccaaacatta gtggccatt cactttgtcc cacaacagat tgcatactgg tggatgggct    360
agacaacaaa acatccacga cttgccaatt tctactgaga tggctggtgt tgacatgaga    420
```

```
ttggaggctg gtgctattag agaattgcac tggcacactg ctgctgaatg ggcttacgtt    480
ttgaagggtt ccactcaggt ttccactgtt actccagacg acagaacta cgttgctact     540 gctaaccagg gagacttgtg gtattttcca ccaggtcaac cacattcctt gcaagctact    600
gctcaagatc cagacggtac tgagttcttg ttggttttcg acaacggtga attctctgag    660
gactccactt tcttgttgac tgactggctt gctcacgttc aaaagaggt tcttgttaga     720 aacttccagg ctactaagtc tgctttcgac acattccag acagagagtt gtacatcttc     780
ccaggtgttc caccagatcc aaacgctcaa ccaccatctt ctccacaagg acagactcca    840
ttgccataca ctttcccatt gtcccaagtt gaggctacta aattcccagg tgtactact    900 aagatcgttg actccactac tttcaaggtt tcaaagacta tggctgttgc tgaggttaca   960
ttggaaccag gtgctatgag agagttgcat tggcatccaa ctcaaactga gtgggactac   1020
ttcatgtctg gttacgctag agttactgtt tcgctgcta atgctgacgc tagaactttc   1080
gacttccagg ctggtgacat tggttacatc ccacaatcct acggtcacta catcgagaac   1140
actggtaaca ctactttgca cttttttggag atcttgaaaa ctgacatcga caagttccag   1200
gacgtttctt tggctcaatg gcttgctttg actcctccag ctgttgttaa ggctcacttg   1260
gatgtttccg acgacactat tgctgctttc tccaagacta agcagagaat cgttggtaaa   1320
taa                                                                   1323

<210> SEQ ID NO 16
<211> LENGTH: 1419
<212> TYPE: DNA
<213> ORGANISM: Artificial Sequence
<220> FEATURE:
<223> OTHER INFORMATION: The sequence is synthetized.

<400> SEQUENCE: 16
atgaaaccat ctacacttta ctcttctcta ccttgggtca tcacgtccct cctcacggta     60
gctgttcatg gcgctcctac agggacgaag tcgaaccctc ccctacgagg ctccgagaac   120
ttgctgggtt actcggcctc caacaccgtg acggaccagt ccaccgatga gatcccttat   180
gtgccggtgc caggacagac cgatgccgct gacctcggcg tgtacttgga ctttgaagat   240
atcgagaacc cgcaaccggt ccgcggaagc acgggaggaa ctgaccctgg acctcgcaac   300
gactactacg atcggattaa tagcgataag ctggctcctc cgggtacgga caatggccag   360
acgatcaatg cccaatggcc tatgggacta agccataatc ggctgggatt gaacgagtct   420
ggatgggctc ggcaagagaa cgaggtggtg atgccgggcg cgaccgagat ggctggagtg   480
gatatgcgcc tagaagcagg tgcttatcgg gagctgcatt ggcatgtggc atcggaatgg   540
tcgttggtgt tgaacggatc gtgtcggatc gaggccgtca acgagaacgg acaaactttc   600
gtcgatgacg tgagcgctgg tgatgtctgg ttcttccctc ccggtgttcc gcattccatc   660
caagccctag actcgggcgt cgagtttctc ctcatctttg atgacggttc cttctctgag   720
gataatactt tcctcgccac tgaagtgttt gcccatcaac cgcgcgaagt cctcgccaaa   780
aacttcgacc tccccgttgc cgcttttcgac gacattccg aagatgaact ttatatcttc   840
cccggcactc cggcaccgca gaacatcgag gagcaaaatg taactggctc cgcaggcgtc   900
ttgcccaagt cccaaagcta ctcgtaccac ttctccgagc agcccgcgca cgaagtgcaa   960
ggcggatccg tcaagatcgt cgactcgctc accttcccca tctccaccaa cacgcgctgcc  1020 gcgctggtga cagtgcaccc aggtggcatg cgcgaaatcc attggcaccc aagcagcgat  1080
```

| | | |
|---|---|---|
| gaatggacgt tcttcatcag tggcaaggca cgcgcgaccc tattcacggc gcccagcacc | 1140 | |
| gccacgacgt tcgattaccg cccgggtgat gtaggatact tcccgcagag caacagtcat | 1200 | |
| tacattgaga acacgggaga tgaggatctg gtcttcttgg aggtgttgca gacggaacaa | 1260 | |
| ttcagcgaca tctcattggg ccagtggatc ggctccacgc cgaagcagat cgtctcggat | 1320 | |
| acgctgaacc tgccgcagag tgcgctggat cggttgaaga cggagaagat gtatgtggtg | 1380 | |
| gctggatcaa atgagacgga tgttgctgct actgcgtag | 1419 | |

<210> SEQ ID NO 17
<211> LENGTH: 1356
<212> TYPE: DNA
<213> ORGANISM: Artificial Sequence
<220> FEATURE:
<223> OTHER INFORMATION: The sequence is synthetized.

<400> SEQUENCE: 17

| | | |
|---|---|---|
| gcccccgccc ccagcagcgc cgccagcagc atcgtcgtca gcgccaccag cagcagcacc | 60 | |
| gtcagcagcg cccccgtcag cgtcagcagc ttcctcccca ccaccagcat cgccgccgcc | 120 | |
| acccccagca gcatcgccgt cgccctcagc agcaccgcca ccgtcccctt catcgacctc | 180 | |
| aaccccaacg gccccctctg gaccccagc gtcagcggcg tccccaggc cgagcgcggc | 240 | |
| agcctcggcg ccaccatcat gggccccacc gacgtcgaca ccaccaaggc caaccccgac | 300 | |
| ctcctcgccc ccctaccac cgaccacggc tctgtcgaca cgccaagtg ggccttttct | 360 | |
| ctctctcaca accgactcca gaccggcggc tgggcccgag agcagaacat tggcgccatg | 420 | |
| cctattgcca ccgagatggc ctctgtcaac atgcgactcg agcctggcgc cattcgagag | 480 | |
| ctccactggc acaagaccgc cgagtgggcc tacgtcctca agggcaacac ccaggtcacc | 540 | |
| gccgtcgacc agaacggcaa gaactttatt ggcaccgtcg gccctggcga cctctggtac | 600 | |
| tttcctcctg gcattcctca ctctctccag gccaccggcg acgaccctga gggctctgag | 660 | |
| tttattctcg tctttgactc tggcgccttt tctgaggact ctacctttct cctcaccgac | 720 | |
| tggatgtctc acgtccctgt cgaggtcctc gccaagaact tcagaccga catttctgcc | 780 | |
| tttgcccgaa ttcctgccga ggagctctac attttcctg ccgccgtccc tcctgactct | 840 | |
| cagcaggacc ctacctctcc tgagggcacc gtccctaacc ctttaccttt gccctctct | 900 | |
| aaggtccctc ctatgcagct ctctggcggc accgccaaga ttgtcgactc taccaccttt | 960 | |
| accgtctcta aggccattgc cgccgccgag gtcaccattg agcctggcgc cattcgagag | 1020 | |
| ctccactggc accctaccca ggacgagtgg tcttttttta ttgagggccg agcccgaatg | 1080 | |
| accattttg ccgcccagtc taacgcccga acctttgact accaggccgg cgacattggc | 1140 | |
| tacgtccctg ccaccatggg ccactacgtc gagaacattg gcaacaccac cgtccgatac | 1200 | |
| ctcgagattt taacaccgc cgtctttgag gacatttctc tctctaactg gctcgccctc | 1260 | |
| accctcctg agctcgtcaa ggccaccctc ggctttgacg acgccaccat ggcccacctc | 1320 | |
| gccaaggtca agcctattgt cgtcggccct gcctaa | 1356 | |

<210> SEQ ID NO 18
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 18

| | |
|---|---|
| gctctagatc tagaaagctt actagtggca ctggccgtcg ttttacaacg | 50 |

```
<210> SEQ ID NO 19
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 19
gaccggatct gtcgatcgac aagc                                          24

<210> SEQ ID NO 20
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 20
ttcaggcttt tcattttgt atctgcgaat tgagcttgc                           39

<210> SEQ ID NO 21
<211> LENGTH: 54
<212> TYPE: DNA
<213> ORGANISM: Artificial Sequence
<220> FEATURE:
<223> OTHER INFORMATION: The sequence is synthetized.

<400> SEQUENCE: 21
gctctagatc tagaggtacc agatctgaat tcgacgcaga agaaggaaat cgcc         54

<210> SEQ ID NO 22
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 22
ccgctcgagc tcgagcttgt cgatcgacag atc                                33

<210> SEQ ID NO 23
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 23
ttcgcagata caaatgaaa aagcctgaac tcaccgcgac                          40

<210> SEQ ID NO 24
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 24
gctctagatg aacagtaagg tgtcagcatg c                                  31

<210> SEQ ID NO 25
<211> LENGTH: 39
<212> TYPE: DNA
<213> ORGANISM: Artificial Sequence
<220> FEATURE:
```

<223> OTHER INFORMATION: The sequence is synthetized.

<400> SEQUENCE: 25
taaatgcctt tctttcgagg cgagggagtt gctttaatg                    39

<210> SEQ ID NO 26
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 26
ctccctcgcc tcgaaagaaa ggcatttagc aagaagg                      37

<210> SEQ ID NO 27
<211> LENGTH: 32
<212> TYPE: DNA
<213> ORGANISM: Artificial Sequence
<220> FEATURE:
<223> OTHER INFORMATION: The sequence is synthetized.

<400> SEQUENCE: 27
gaagatctag tgtttgatgc tcacgctcgg at                           32

<210> SEQ ID NO 28
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 28
cgcctcttct ttgtgctttt ctc                                     23

<210> SEQ ID NO 29
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 29
gtgggcttcc ttgtttctcg acc                                     23

<210> SEQ ID NO 30
<211> LENGTH: 32
<212> TYPE: DNA
<213> ORGANISM: Artificial Sequence
<220> FEATURE:
<223> OTHER INFORMATION: The sequence is synthetized.

<400> SEQUENCE: 30
gaattcagat ctggtacctc tagaaagctt ac                           32

<210> SEQ ID NO 31
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 31
ggatcccgaa ttaattcggc gttaattcag tac                          33

```
<210> SEQ ID NO 32
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 32
ttcccttcct ctaggccgct ggtcaatgtt atctgg                              36

<210> SEQ ID NO 33
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 33
accagatctg aattccttcc taataccgcc tagtcatagc                          40

<210> SEQ ID NO 34
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 34
attaattcgg gatcctcacg gtgaatgtag gccttttgta                          40

<210> SEQ ID NO 35
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 35
cattgaccag cggcctagag gaagggaaaa gaatggcac                           39

<210> SEQ ID NO 36
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 36
cggaattctc acggtgaatg tagg                                           24

<210> SEQ ID NO 37
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 37
ctttcgcacg gagctagcac gagctgtggc caagaag                             37

<210> SEQ ID NO 38
<211> LENGTH: 40
<212> TYPE: DNA
<213> ORGANISM: Artificial Sequence
<220> FEATURE:
<223> OTHER INFORMATION: The sequence is synthetized.
```

<400> SEQUENCE: 38
ccacagctcg tgctagctcc gtgcgaaagc ctgacgcacc                              40

<210> SEQ ID NO 39
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 39
aactgcagca tcgtaaccga gaatccagag ctg                                     33

<210> SEQ ID NO 40
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 40
agcacgagct gtggccaaga ag                                                 22

<210> SEQ ID NO 41
<211> LENGTH: 26
<212> TYPE: DNA
<213> ORGANISM: Artificial Sequence
<220> FEATURE:
<223> OTHER INFORMATION: The sequence is synthetized.

<400> SEQUENCE: 41
agctccgtgc gaaagcctga cgcacc                                             26

<210> SEQ ID NO 42
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 42
gccacagctc gtgctgcccc cgccccagc agcgccgcc                                39

<210> SEQ ID NO 43
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 43
ctttcgcacg gagctttagg cagggccgac gacaatagg                               39

<210> SEQ ID NO 44
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 44
attaggaagg aattctcacg gtgaatgtag gccttttg                                38

<210> SEQ ID NO 45
<211> LENGTH: 38

```
<212> TYPE: DNA
<213> ORGANISM: Artificial Sequence
<220> FEATURE:
<223> OTHER INFORMATION: The sequence is synthetized.

<400> SEQUENCE: 45
agtaagcttt ctagacatcg taaccgagaa tccagagc                              38

<210> SEQ ID NO 46
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 46
attaattcgg gatccaggac ttccagggct acttggcgc                             39

<210> SEQ ID NO 47
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 47
tcaatggtac gaggtgccgc tggtcaatgt tatctgg                               37

<210> SEQ ID NO 48
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 48
cattgaccag cggcacctcg taccattgac tctgtctg                              38

<210> SEQ ID NO 49
<211> LENGTH: 29
<212> TYPE: DNA
<213> ORGANISM: Artificial Sequence
<220> FEATURE:
<223> OTHER INFORMATION: The sequence is synthetized.

<400> SEQUENCE: 49
accatatgag gacttccagg gctacttgg                                        29

<210> SEQ ID NO 50
<211> LENGTH: 35
<212> TYPE: DNA
<213> ORGANISM: Artificial Sequence
<220> FEATURE:
<223> OTHER INFORMATION: The sequence is synthetized.

<400> SEQUENCE: 50
gacttcatgc cggggattgt gctgtagctg cgctg                                 35

<210> SEQ ID NO 51
<211> LENGTH: 33
<212> TYPE: DNA
<213> ORGANISM: Artificial Sequence
<220> FEATURE:
<223> OTHER INFORMATION: The sequence is synthetized.

<400> SEQUENCE: 51
```
gctacagcac aatccccggc atgaagtctg acc                                    33

<210> SEQ ID NO 52
<211> LENGTH: 30
<212> TYPE: DNA
<213> ORGANISM: Artificial Sequence
<220> FEATURE:
<223> OTHER INFORMATION: The sequence is synthetized.

<400> SEQUENCE: 52
gcctgcagtg gacgcctcga tgtcttcctc                                        30

<210> SEQ ID NO 53
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 53
agctacagca caatcatgta tcggaagttg gccgtcatc                              39

<210> SEQ ID NO 54
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 54
agacttcatg ccgggttagg cagggccgac gacaatagg                              39

<210> SEQ ID NO 55
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 55
gattgtgctg tagctgcgct g                                                 21

<210> SEQ ID NO 56
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 56
cccggcatga agtctgacc                                                    19

<210> SEQ ID NO 57
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 57
attaggaagg aattcaggac ttccagggct acttggc                                37

<210> SEQ ID NO 58
<211> LENGTH: 37
<212> TYPE: DNA
<213> ORGANISM: Artificial Sequence

```
<220> FEATURE:
<223> OTHER INFORMATION: The sequence is synthetized.

<400> SEQUENCE: 58
agtaagcttt ctagatggac gcctcgatgt cttcctc                               37

<210> SEQ ID NO 59
<211> LENGTH: 33
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t

<400> SEQUENCE: 59
acgatggact ccagagcggc cgcvnvnnng gaa                                   33

<210> SEQ ID NO 60
<211> LENGTH: 33
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t

<400> SEQUENCE: 60
acgatggact ccagagcggc cgcbnbnnng gtt                                   33

<210> SEQ ID NO 61
<211> LENGTH: 34
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 61
acgatggact ccagagcggc cgcvvnvnnn ccaa                                  34

<210> SEQ ID NO 62
<211> LENGTH: 34
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (26)..(26)
<223> OTHER INFORMATION: n is a, c, g, or t
<220> FEATURE:
```

```
<221> NAME/KEY: misc_feature
<222> LOCATION: (28)..(30)
<223> OTHER INFORMATION: n is a, c, g, or t

<400> SEQUENCE: 62
acgatggact ccagagcggc cgcbdnbnnn cggt                              34

<210> SEQ ID NO 63
<211> LENGTH: 34
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 63
acgatggact ccagagcggc cgcbhndnnn gacc                              34

<210> SEQ ID NO 64
<211> LENGTH: 16
<212> TYPE: DNA
<213> ORGANISM: Artificial Sequence
<220> FEATURE:
<223> OTHER INFORMATION: The sequence is synthetized.

<400> SEQUENCE: 64
acgatggact ccagag                                                  16

<210> SEQ ID NO 65
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 65
ggccgtcgtt ttacaacgtc gtgac                                        25

<210> SEQ ID NO 66
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 66
gcgtaatagc gaagaggccc gcacc                                        25

<210> SEQ ID NO 67
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 67
ttatagtatt agttttccgc cgac                                         24

<210> SEQ ID NO 68
<211> LENGTH: 23
```

```
<212> TYPE: DNA
<213> ORGANISM: Artificial Sequence
<220> FEATURE:
<223> OTHER INFORMATION: The sequence is synthetized.

<400> SEQUENCE: 68
atgtcctcca agtcgcgatt gac                                         23

<210> SEQ ID NO 69
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 69
ttacttgggt gttctcagct tg                                          22

<210> SEQ ID NO 70
<211> LENGTH: 32
<212> TYPE: DNA
<213> ORGANISM: Artificial Sequence
<220> FEATURE:
<223> OTHER INFORMATION: The sequence is synthetized.

<400> SEQUENCE: 70
tcagatctag tgtttgatgc tcacgctcgg at                               32

<210> SEQ ID NO 71
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 71
tttctagatg aacagtaagg tgtcagca                                    28

<210> SEQ ID NO 72
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 72
caaacgaaca catcactttc aaag                                        24

<210> SEQ ID NO 73
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 73
gtgggcttcc ttgtttctcg acc                                         23

<210> SEQ ID NO 74
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 74
```
tccttcttct gcgtcgaatt ctccgtattt cagcagtaac ccctg    46

<210> SEQ ID NO 75
<211> LENGTH: 42
<212> TYPE: DNA
<213> ORGANISM: Artificial Sequence
<220> FEATURE:
<223> OTHER INFORMATION: The sequence is synthetized.

<400> SEQUENCE: 75
acccttgcat atgctccttg aaaggacctt gacagaacgg ag    42

<210> SEQ ID NO 76
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 76
ccgttctgtc aaggtccttt caaggagcat atgcaagggt atc    43

<210> SEQ ID NO 77
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 77
tcaatatcat cttctgtcga tcattgtcat gacgctacag aagc    44

<210> SEQ ID NO 78
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 78
ggatggtttg gatgcagttg aaggtgggcg ctaccgagaa g    41

<210> SEQ ID NO 79
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 79
gccactagta agctttctag agctttgagt tccgattcta ccctc    45

<210> SEQ ID NO 80
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 80
ctgtagcgtc atgacaatga tcgacagaag atgatattga aggagc    46

<210> SEQ ID NO 81
<211> LENGTH: 46
<212> TYPE: DNA
<213> ORGANISM: Artificial Sequence

```
<220> FEATURE:
<223> OTHER INFORMATION: The sequence is synthetized.

<400> SEQUENCE: 81
gtcttctcgg tagcgcccac cttcaactgc atccaaacca tcctac           46

<210> SEQ ID NO 82
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 82
gattaggaag taaccatggc accacacccg acgctcaag                   39

<210> SEQ ID NO 83
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 83
gggtgtggtg ccatggttac ttcctaatcg aagctttgc                   39

<210> SEQ ID NO 84
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 84
gaacccggac gttgaatctg c                                      21

<210> SEQ ID NO 85
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 85
gcattcattg ttgacctcca ctagc                                  25

<210> SEQ ID NO 86
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 86
gcatttgctt ttgcgcgtgg ag                                     22

<210> SEQ ID NO 87
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 87
gtggatcaac gtcaatgggc tcag                                   24
```

<210> SEQ ID NO 88
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 88
gtggattcgg ccaaaggact ccg                                           23

<210> SEQ ID NO 89
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 89
gtttaaactg aaggcgggaa acgac                                         25

<210> SEQ ID NO 90
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 90
agagtgcaca ctagtcgtac ccgtacaagt cgtaatc                            37

<210> SEQ ID NO 91
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 91
ctcgtgctct ctcgcgatat catcgtaacc gagaatccag agc                     43

<210> SEQ ID NO 92
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 92
ctggattctc ggttacgatg atatcgcgag agagcacgag                         40

<210> SEQ ID NO 93
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 93
tatcatcttc tgtcgaaata cattaacaac acagtttcag ccc                     43

<210> SEQ ID NO 94
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 94
aactgtgttg ttaatgtatt tcgacagaag atgatattga aggagc                    46

<210> SEQ ID NO 95
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 95
ctcgtgctct ctcgcgatat caactgcatc caaaccatcc t                         41

<210> SEQ ID NO 96
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 96
gatggtttgg atgcagttga tatcgcgaga gagcacgag                            39

<210> SEQ ID NO 97
<211> LENGTH: 35
<212> TYPE: DNA
<213> ORGANISM: Artificial Sequence
<220> FEATURE:
<223> OTHER INFORMATION: The sequence is synthetized.

<400> SEQUENCE: 97
ggtcgactct agagggcccg gcttcagagc tcatg                                35

<210> SEQ ID NO 98
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 98
actagtgtgc actctcccga attaattcgg cgttaattca g                         41

<210> SEQ ID NO 99
<211> LENGTH: 35
<212> TYPE: DNA
<213> ORGANISM: Artificial Sequence
<220> FEATURE:
<223> OTHER INFORMATION: The sequence is synthetized.

<400> SEQUENCE: 99
cctctagagt cgaccggcac tggccgtcgt tttac                                35

<210> SEQ ID NO 100
<211> LENGTH: 45
<212> TYPE: DNA
<213> ORGANISM: Artificial Sequence
<220> FEATURE:
<223> OTHER INFORMATION: The sequence is synthetized.

<400> SEQUENCE: 100
agagtgcaca ctagttgtat cgaaccatta gtccgtatag tatcg                     45

<210> SEQ ID NO 101

```
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 101
tcttctgtcg acgaattcca tgtatcaatg ggttatacgt atcatatagg            50

<210> SEQ ID NO 102
<211> LENGTH: 48
<212> TYPE: DNA
<213> ORGANISM: Artificial Sequence
<220> FEATURE:
<223> OTHER INFORMATION: The sequence is synthetized.

<400> SEQUENCE: 102
acccattgat acatggaatt cgtcgacaga agatgatatt gaaggagc              48

<210> SEQ ID NO 103
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 103
gccgaatcga tctttcaact gcatccaaac catcctacc                       39

<210> SEQ ID NO 104
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 104
gtttggatgc agttgaaaga tcgattcggc agtcgag                         37

<210> SEQ ID NO 105
<211> LENGTH: 46
<212> TYPE: DNA
<213> ORGANISM: Artificial Sequence
<220> FEATURE:
<223> OTHER INFORMATION: The sequence is synthetized.

<400> SEQUENCE: 105
ggtcgactct agaggtatgt gagcaacaat aatacagtat agtaag                46

<210> SEQ ID NO 106
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 106
acccattgat acatggaatt gaattctcac ggtgaatgta ggc                   43

<210> SEQ ID NO 107
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 107
```
gccgaatcga tctttcatcg taaccgagaa tccagagc                    38

<210> SEQ ID NO 108
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 108
ttctcggtta cgatgaaaga tcgattcggc agtcgag                     37

<210> SEQ ID NO 109
<211> LENGTH: 44
<212> TYPE: DNA
<213> ORGANISM: Artificial Sequence
<220> FEATURE:
<223> OTHER INFORMATION: The sequence is synthetized.

<400> SEQUENCE: 109
tcatcttctg tcgacgaatt gaatacaatc aacagcgcta gacg             44

<210> SEQ ID NO 110
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 110
agagtgcaca ctagtcaatt gcaccaaccg ccatcctc                    38

<210> SEQ ID NO 111
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 111
ttacatcatg aaagactcaa tatgcgatcc ctctcgcg                    38

<210> SEQ ID NO 112
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 112
tctttcatga tgtaatcgac agaagatgat attgaaggag                  40

<210> SEQ ID NO 113
<211> LENGTH: 42
<212> TYPE: DNA
<213> ORGANISM: Artificial Sequence
<220> FEATURE:
<223> OTHER INFORMATION: The sequence is synthetized.

<400> SEQUENCE: 113
ctttgcgtcc cttgtgacgc aactgcatcc aaaccatcct ac               42

<210> SEQ ID NO 114
<211> LENGTH: 39
<212> TYPE: DNA

```
<213> ORGANISM: Artificial Sequence
<220> FEATURE:
<223> OTHER INFORMATION: The sequence is synthetized.

<400> SEQUENCE: 114
tggtttggat gcagttgcgt cacaagggac gcaaagttg                              39

<210> SEQ ID NO 115
<211> LENGTH: 43
<212> TYPE: DNA
<213> ORGANISM: Artificial Sequence
<220> FEATURE:
<223> OTHER INFORMATION: The sequence is synthetized.

<400> SEQUENCE: 115
atgtagatac aacatagcat catcgtaacc gagaatccag agc                         43

<210> SEQ ID NO 116
<211> LENGTH: 51
<212> TYPE: DNA
<213> ORGANISM: Artificial Sequence
<220> FEATURE:
<223> OTHER INFORMATION: The sequence is synthetized.

<400> SEQUENCE: 116
ctggattctc ggttacgatg atgctatgtt gtatctacat tagcaaatga c                51

<210> SEQ ID NO 117
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 117
ggtcgactct agaggccttg gtcatttcgg ggtgtc                                 36

<210> SEQ ID NO 118
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 118
tctttcatga tgtaagaatt ctcacggtga atgtaggc                               38

<210> SEQ ID NO 119
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 119
atcatcttct gtcgacatcg taaccgagaa tccagagc                               38

<210> SEQ ID NO 120
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 120
tcgacagaag atgatattga aggagcactt tttgggcttg                             40
```

<210> SEQ ID NO 121
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 121
ttacatcatg aaagactcaa tatgcgatcc ctctcgcg                               38

<210> SEQ ID NO 122
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 122
agagtgcaca ctagtagcgt ggctcaggag agcgaac                                37

<210> SEQ ID NO 123
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 123
gcattgtgcc aggtgatata tcctgaaacc c                                     31

<210> SEQ ID NO 124
<211> LENGTH: 40
<212> TYPE: DNA
<213> ORGANISM: Artificial Sequence
<220> FEATURE:
<223> OTHER INFORMATION: The sequence is synthetized.

<400> SEQUENCE: 124
cacctggcac aatgctcgac agaagatgat attgaaggag                            40

<210> SEQ ID NO 125
<211> LENGTH: 42
<212> TYPE: DNA
<213> ORGANISM: Artificial Sequence
<220> FEATURE:
<223> OTHER INFORMATION: The sequence is synthetized.

<400> SEQUENCE: 125
ctttcgacgg aagctcattc atcgtaaccg agaatccaga gc                         42

<210> SEQ ID NO 126
<211> LENGTH: 41
<212> TYPE: DNA
<213> ORGANISM: Artificial Sequence
<220> FEATURE:
<223> OTHER INFORMATION: The sequence is synthetized.

<400> SEQUENCE: 126
ctggattctc ggttacgatg aatgagcttc cgtcgaaaga g                          41

<210> SEQ ID NO 127
<211> LENGTH: 36
<212> TYPE: DNA
<213> ORGANISM: Artificial Sequence
<220> FEATURE:

<223> OTHER INFORMATION: The sequence is synthetized.

<400> SEQUENCE: 127
ggtcgactct agaggtcaga gccagttgtc gatgcc                               36

<210> SEQ ID NO 128
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 128
cacctggcac aatgcgaatt ctcacggtga atgtaggc                             38

<210> SEQ ID NO 129
<211> LENGTH: 25
<212> TYPE: DNA
<213> ORGANISM: Artificial Sequence
<220> FEATURE:
<223> OTHER INFORMATION: The sequence is synthetized.

<400> SEQUENCE: 129
aattctggag acggcttgtt gaatc                                           25

<210> SEQ ID NO 130
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 130
cgagtcgcat gttgacagag g                                               21

<210> SEQ ID NO 131
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 131
gcatttgctt ttgcgcgtgg ag                                              22

<210> SEQ ID NO 132
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 132
agtaagcttt ctagagatcg gtgaacagtt gtcgacc                              37

<210> SEQ ID NO 133
<211> LENGTH: 26
<212> TYPE: DNA
<213> ORGANISM: Artificial Sequence
<220> FEATURE:
<223> OTHER INFORMATION: The sequence is synthetized.

<400> SEQUENCE: 133
gaatgtgctg cctccaaaat cctgcg                                          26

```
<210> SEQ ID NO 134
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 134
caaagcggct cgtcttggcc agg                                              23

<210> SEQ ID NO 135
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 135
ggtgctgaga gctggacaat g                                                21

<210> SEQ ID NO 136
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 136
gcgaccaggt tcccacgaac tac                                              23

<210> SEQ ID NO 137
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 137
gctattggac atgccgtcga tg                                               22

<210> SEQ ID NO 138
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 138
agcctcatgt tcttctccca gac                                              23

<210> SEQ ID NO 139
<211> LENGTH: 26
<212> TYPE: DNA
<213> ORGANISM: Artificial Sequence
<220> FEATURE:
<223> OTHER INFORMATION: The sequence is synthetized.

<400> SEQUENCE: 139
gtctgctcag gcattatctt cactgc                                           26

<210> SEQ ID NO 140
<211> LENGTH: 22
<212> TYPE: DNA
<213> ORGANISM: Artificial Sequence
<220> FEATURE:
<223> OTHER INFORMATION: The sequence is synthetized.
```

```
<400> SEQUENCE: 140
ctgacgggat cttttgcctg ca                                              22

<210> SEQ ID NO 141
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 141
gtcttattgg cgctgcatgc t                                               21

<210> SEQ ID NO 142
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 142
ctgagctgat ctatgagtca taagcttc                                        28

<210> SEQ ID NO 143
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 143
gtatcagatg tgaactgcgc tg                                              22

<210> SEQ ID NO 144
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 144
gtgctgggag acgatgtgat g                                               21

<210> SEQ ID NO 145
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 145
cagcagcgac gcgattcctt c                                               21

<210> SEQ ID NO 146
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 146
ctgcttcaga atgatgcgga tg                                              22
```